(12) United States Patent
Hone et al.

(10) Patent No.: US 8,053,568 B2
(45) Date of Patent: *Nov. 8, 2011

(54) BACTERIAL PACKAGING STRAINS USEFUL FOR GENERATION AND PRODUCTION OF RECOMBINANT DOUBLE-STRANDED RNA NUCLEOCAPSIDS AND USES THEREOF

(75) Inventors: David Hone, Rockville, MD (US); John Fulkerson, Silver Spring, MD (US); Jerald C. Sadoff, Washington, DC (US); David Onyabe, Poolesville, MD (US); Michele Stone, Ellicott City, MD (US)

(73) Assignee: Aeras Global TB Vaccine Foundation, Rockville, MD (US)

( * ) Notice: Subject to any disclaimer, the term of this patent is extended or adjusted under 35 U.S.C. 154(b) by 1485 days.

This patent is subject to a terminal disclaimer.

(21) Appl. No.: 11/284,817

(22) Filed: Nov. 23, 2005

(65) Prior Publication Data

US 2006/0115493 A1    Jun. 1, 2006

Related U.S. Application Data

(60) Provisional application No. 60/713,729, filed on Sep. 6, 2005.

(51) Int. Cl.
*C12N 15/11* (2006.01)
*C07H 21/04* (2006.01)
*A61K 38/16* (2006.01)
(52) U.S. Cl. .................... 536/23.1; 536/23.72; 530/358
(58) Field of Classification Search .................. None
See application file for complete search history.

*Primary Examiner* — Michele K Joike
(74) *Attorney, Agent, or Firm* — Whitham Curtis Christofferson & Cook, PC

(57) ABSTRACT

Bacterial packaging strains useful for generating recombinant double-stranded RNA nucleocapsids (rdsRNs) are provided. The packaging strains are useful for the production of RNA encoding vaccine antigens, bioactive proteins, immunoregulatory proteins, antisense RNAs, and catalytic RNAs in eukaryotic cells or tissues. Recombinant ssRNA is introduced into the strains and packaged to form rdsRNs de novo.

25 Claims, 13 Drawing Sheets

As measured by gentamicin protection assay,
$1.0 \times 10^6 - 1.2 \times 10^6$ HeLa per well, MOI = 100

15D          AVG= $1.34 \times 10^5$ cfu
MPC51        AVG= $2.23 \times 10^4$ cfu
MPC51pYA3342 AVG= $7.40 \times 10^4$ cfu

*Figure 7*

MPC51pLM2653 carrying rdsRP LSMtb4, reverse transcription step performed with only + or – strand specific primer, respectively

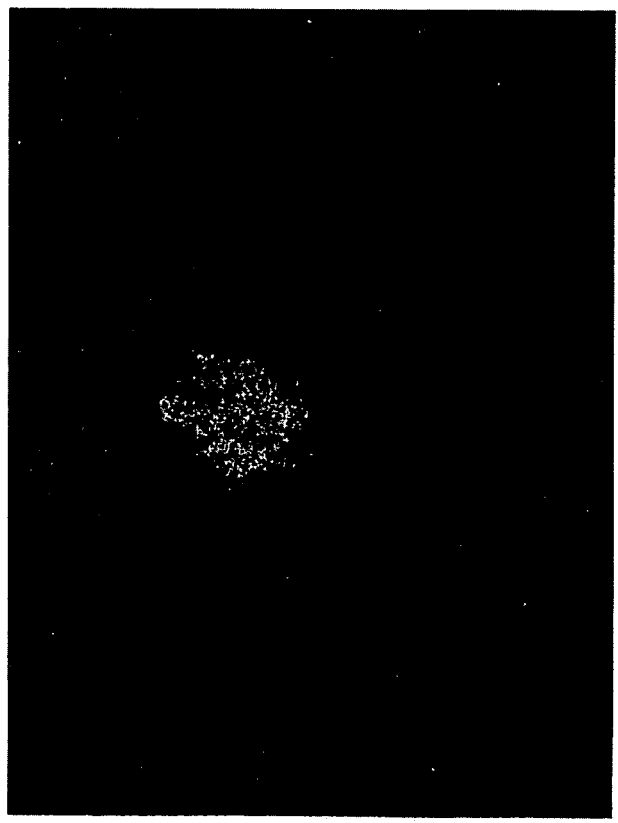
Figure 14

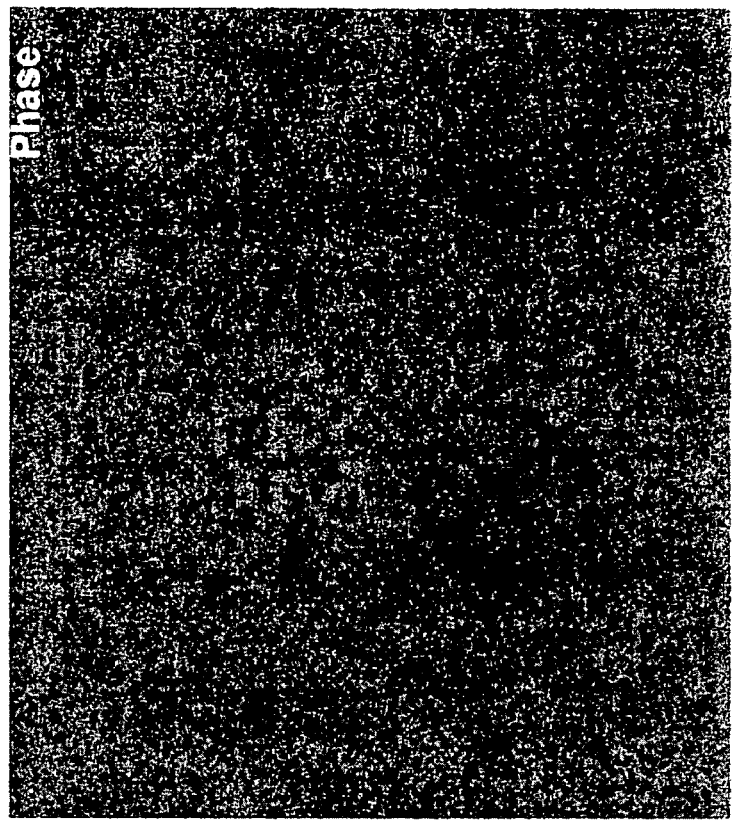
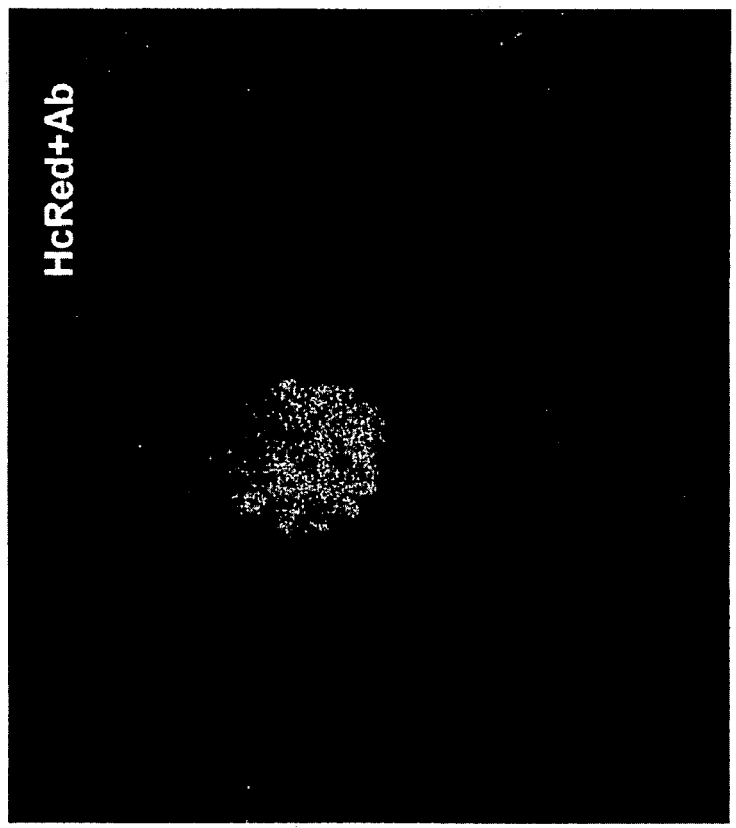
Figure 15

BACTERIAL PACKAGING STRAINS USEFUL FOR GENERATION AND PRODUCTION OF RECOMBINANT DOUBLE-STRANDED RNA NUCLEOCAPSIDS AND USES THEREOF

This application claims benefit of U.S. patent application Ser. No. 10/999,074, filed Nov. 30, 2004, and U.S. Provisional patent application 60/713,729, filed Sep. 6, 2005, the complete contents of both of which are hereby incorporated by reference.

DESCRIPTION

Field of the Invention

The present invention provides bacterial packaging strains useful for generating recombinant double-stranded RNA nucleocapsids (rdsRNs) for the production of RNA encoding vaccine antigens, bioactive proteins, immunoregulatory proteins, antisense RNAs, and catalytic RNAs in eukaryotic cells or tissues. In particular, the invention provides bacterial packaging strains into which recombinant ssRNA is introduced and packaged to form rdsRNs de novo that replicate within the packaging strains and in-turn produce RNA of interest.

Background

Viral nucleocapsids, the viral nucleoprotein core, possess numerous characteristics that may make them of value in the expression of heterologous gene sequences in biological systems. Lacking the outer membranes and adhesins of complete viruses, nucleocapsids are non-infectious particles consisting of the proteins and genetic material of the viral core that retain the capacity to encapsidate and replicate nucleic acid sequences. The risk of infection or environmental spread may thus be mitigated by the elimination of sequences encoding membranes, adhesins, proteases, and other infective or cytolytic factors of the parent virus. RNA nucleocapsids further improve the safety of such gene expression systems by the selection of viral precursors that do not exhibit a DNA stage in their replicative cycle, and hence reduce the risk of incorporation of foreign nucleotide sequence into the genome of the cell or organism into which they are introduced. The inherent instability of RNA can be negated by the utilization of double-stranded RNA (herein "dsRNA") viruses in the design of such nucleocapsid expression systems. Further, the elimination of non-nucleocapsid sequences and the typical segmentation of the genomes of dsRNA viruses make the design of artificial genomic segments replacing the deleted sequences and encoding heterologous RNA an attractive means by which to express genes of interest or deliver RNA of interest into biological systems. A recombinant nucleocapsid expression system could thus be designed such that it may contain sequences necessary to encode only the production of additional nucleocapsids, heterologous sequences of interest, and sequences necessary for their propagation and production in a cell.

The double-stranded RNA phage (herein "dsRP") of the cystoviridae family are prototypical ds RNA viruses (Sinclair et al., J. Virol. 16:685; 1975); (Mgraw et al., J. Virol. 58:142; 1986); (Gottlieb et al., Virology 163:183; 1988); (Mindich et al., J. Virol. 62:1180; 1988); (Mindich, Microbiol. Mol. Biol. Rev. 63, 149; 1999). The distinguishing attributes of cystoviridae dsRP are a genome comprised of three double-stranded RNA (herein "dsRNA") segments (Mcgraw et al., supra, 1986); (Gottlieb et al., supra, 1988); (Mindich et al., supra, 1988) designated segment-L, segment-M and segment-S, and a lipid-containing membrane coat (Sands and Lowlicht, Can J Microbiol, 22:154; 1976); (Bamford, and Palva, Biochim Biophys Acta, 601:245; 1980). The genomic segments are contained within the nucleocapsid core, which is comprised of the proteins P1, P2, P4, and P7, and is produced by genes encoded on dsRNA segment-L (e.g. GenBank Accession # AF226851). Synthesis of positive-strand RNA (herein "mRNA") occurs within the nucleocapsid and is carried out by RNA-dependent RNA polymerase encoded in part by gene-2 on segment-L (Mindich et al., supra, 1988); (Van Etten et al., J Virol, 12:464; 1973); gene-7 on segment-L also plays a role in mRNA synthesis (Mindich, et al., supra, 1999).

DsRP phi-6, the archetype of this family of dsRNA phage, normally infects Pseudomonas syringae (Mindich, et al., supra, 1999), however, more recently isolated dsRP phi-8, phi-11, phi-12 and phi-13 can infect and replicate to some extent in Escherichia coli strain JM109 (American type tissue culture collection (herein "ATCC") # 53323) and O-antigen negative mutants of Salmonella enterica serovar Typhimurium (herein designated "S. typhimurium") (Mindich et al., supra, 1999); (Mindich et al., J. Bacteriol, 181:4505; 1999); (Hoogstraten et al., Virology, 272: 218; 2000); (Qiao et al., Virology 275: 218; 2000).

The life cycle of the archetype dsRP phi-6 in bacteria has been described (Mindich, Adv Virus Res, 35:137; 1988); (Mindich, et al., supra, 1999). Phi-6 infects host cells by binding to the pilus allowing contact with the host cell membrane, thereby resulting in fusion and introduction of the nucleocapsid into the periplasm. The nucleocapsid then is transported into the cytoplasm, an event that requires the endopeptidase activity of protein P5 and the transporting property of protein P8. Interestingly, nucleocapsids that bear a complete P8 shell are capable of spontaneous entry into bacterial protoplasts, resulting in auto-transfection of the bacterial strain from which the protoplasts were prepared (Qiao et al., Virology 227:103; 1997); (Olkkonen et al., Proc. Natl. Acad. Sci. 87: 9173; 1990).

Upon entering the cytoplasm, P8 is shed and the remaining nucleocapsid, which contains the three dsRNA segments and possesses RNA-dependent RNA polymerase activity, begins to synthesize mRNA copies of the dsRNA segments L, M and S. The proteins produced by segment-L are mainly associated with procapsid production; segment-M is mainly dedicated to the synthesis of the attachment proteins and segment-S produces the procapsid shell protein (P8), the lytic endopeptidase (P5), and the proteins (P9 and P12) involved in the generation of the lipid envelope (Johnson and Mindich, J Bacteriol, 176: 4124; 1994). Packaging of the dsRNA segments occurs in sequential manner, whereby segment-S is recognized and taken up by empty procapsids; procapsids containing segment-S no longer bind this segment but now are capable of binding and taking up segment-M; procapsids that contain segments S and M no longer bind these segments but now are capable of binding and taking up segment-L, resulting in the generation of the nucleocapsid. Once the nucleocapsid contains all three single-stranded RNA (herein "ssRNA") segments synthesis of the negative RNA strands begins to produce the dsRNA segments. The nucleocapsid then associates with proteins 5 and 8 and finally is encapsulated in the lipid membrane, resulting in the completion of phage assembly. Lysis of the host cell is thought to occur through the accumulation of the membrane disrupter protein P10, a product of segment-M, and requires the endopeptidase P5 (Mindich et al., supra, 1999)

The assembly of and RNA polymerase activity in dsRP procapsids does not require host proteins, as procapsids purified from an E. coli JM109 derivative that expressed a cDNA copy of segment-L are capable of packaging purified ssRNA segments L, M, and S (Mindich et al., supra, 1999); (Qiao et al., supra, 1997). Following uptake of the ssRNA segments in the above in vitro system, addition of ribonucleotides resulted in negative strand synthesis and the generation of the mature dsRNA segments. Furthermore, after the completion of dsRNA synthesis P8 associates with nucleocapsids and, as indicated above, the resulting product is capable of entering bacterial protoplasts and producing a productive infection; (Qiao et al., supra, 1997).

Previous studies describe the generation of recombinant dsRP (herein referred to as "rdsRP") (Mindich, Adv Virus Res 53:341; 1999); (Onodera et al., J Virol 66:190; 1992). A simple rdsRP was constructed by inserting the kanamycin-resistance allele into segment-M of dsRP phi-6. RdsRP harboring the recombinant segment were isolated by infecting JM109 carrying a plasmid that expressed the recombinant segment-M with wild-type dsRP phi-6. Through this approach a carrier state was established in host cells, in which infectious rdsRP were continuously produced by the carrier strain (Onodera et al., supra, 1992); (Mindich, Adv Virus Res 53:341; 1999). The plaque-forming capacity of the phage produced by the carrier strains was maintained for three-five plate passages; however, after additional passages the nascent phage no longer formed plaques on the carrier strain, yet low-levels of infectious phage were still produced (Onodera et al., supra, 1992). In some instances, a significant number of carrier strains lost the ability to produce infectious phage all together; the dsRNA from such bacterial strains displayed deletions in one or more of the segments (Onodera et al., supra, 1992). In one instance a mutant phage lacking the segment-S was isolated from one such carrier strain that had lost the capacity to produce phage. In no instances were rdsRNs constructed with the express purpose of adapting the system to function in a eukaryotic cell or tissues. Thus, rdsRP produced by this method are inherently unstable, and are not useful for analysis of phage assembly and replication; the rdsRP provided by the prior art are not compatible with biotechnology applications and large-scale manufacturing.

It has been recently suggested that rdsRP could be developed that would be capable of expressing mRNA in eukaryotic cells, and that such rdsRP might be useful for the expression of vaccine antigens, bioactive proteins, immunoregulatory proteins, antisense RNAs, and catalytic RNAs in eukaryotic cells or tissues (U.S. patent application 20040132678 to Hone, which is herein incorporated by reference, hereafter 20040132678). 20040132678 provides extensive information on the usefulness of rdsRP, describes a model rdsRP and proposes methods for generating and using the same. However, 20040132678 provides no guidance on how to launch rdsRPs de novo, or how to generate and isolate stable carrier strains that harbor and replicate the rdsRPs. In one example in 20040132678, it is proposed that batches of rdsRP can be generated by replicating a parent dsRP in the bacterial transformants that carry plasmids, which in turn express the recombinant segment of interest. It is unclear from this description as to whether such rdsRP harbor four dsRNA segments (i.e. the three wild-type segments and the recombinant segment) or whether such rdsRP harbor three dsRNA segments, two wild-type segments and the recombinant segment. In either instance, it is unclear how dependent the rdsRP are on the wild-type helper phage for propagation; it is also unclear how the rdsRP would be separated from the wild type dsRP. Furthermore, 20040132678 does not provide specific methods to stably incorporate recombinant segments into dsRP, and only provides scant attention to the specific methods for the subsequent replication and stable production of rdsRP. Moreover, 20040132678 does not provide stable rdsRP compositions lacking both wild-type segment-M and segment-S. Finally, 20040132678 also does not provide packaging strains that express segment-L and produce procapsids, and thus are capable of launching rdsRPs de novo and stably producing rdsRPs.

Hence, 20040132678 does not provide adequate information to enable those skilled in the art to generate packaging strains and stably produce rdsRP. Furthermore, 20040132678 does not discuss or suggest novel rdsRN compositions, or packaging strains, or methods to launch and stably produce and use rdsRNs, that are the subject of this invention.

SUMMARY OF THE INVENTION

According to the invention, a recombinant double-stranded RNA nucleocapsid (rdsRN) includes at least one dsRNA segment encoding functional double-stranded RNA viral or bacteriophage nucleocapsid proteins and one or more recombinant dsRNA segments that include at least one gene encoding a functional product that complements a selectable phenotypic mutation in a host (e.g. bacterial) cell, such as an auxotropic mutation, cell wall synthesis mutation, or a mutation that prevents growth above freezing temperature. Preferably, the dsRN segments include RNA encoding a heterologous gene of interest such as an immunogen, with or without adjuvants, which would allow use of the invention in vaccines that elicit an immune response, although the function of the mRNA produced by such rdsRN's is not limited to this function. RNAs so produced could encode adjuvants, immunomodulatory proteins, therapeutic proteins, other bioactive proteins, or the RNA itself may function as siRNA or catalytic RNA. rdsRNs have advantages in terms of stability and handling and safety, etc. relative to rdsRPs. The rdsRN is harbored in a bacterial packaging strain cell that includes the selectable phenotypic mutation, thereby allowing selection and maintenance of the rdsRNs within the bacterial packaging strain.

Exemplary embodiments of the invention are depicted schematically in FIGS. 1-3. In each of FIGS. 1-3, 10 represents a bacterial cell; 20 represents the genomic DNA of the bacterial cell 10; 30 represents a nucleocapsid (comprised of proteins with packaging activity and RNA polymerase activity); and 31 (three wavy lines within nucleocapsid 30) represents dsRNA contained within nucleocapsid 30. Likewise, in each of FIGS. 1-3, 21 represents a selectable phenotypic mutation in genomic DNA 20.

As can be seen in each of FIGS. 1-3, two elements, 40 and 41, are consistently associated with dsRNA 31. 40 represents a nucleic acid sequence encoding a gene product that complements selectable phenotypic mutation 21, and 41 represents a nucleic acid sequence that encodes an RNA of interest.

A third element, 42, is found in each of FIGS. 1-3, but its location varies. 42 represents nucleic acid sequences that encode genes necessary for nucleocapsid production (e.g. genes encoding proteins with packaging activity and RNA polymerase activity). FIG. 1 illustrates an embodiment of the invention in which nucleic acid sequences 42 are located within dsRNA sequences 31 inside nucleocapsid 30. In another embodiment of the invention, illustrated in FIG. 2, nucleic acid sequences 42 are located within bacterial genomic DNA 20. In yet another embodiment of the invention, illustrated in FIG. 3, bacterial cell 10 also contains a plasmid (70), and nucleic acid sequences 42 are located on plasmid 70.

An object of the present invention is to provide bacterial packaging strains, comprising sequences encoding dsRP procapsids in said strain and a mutation to enable selection and maintenance of the rdsRNs that express a functional gene that complements the mutation in said strain. In one embodimetn, a bacterial strain for packaging, producing and/or delivering genes or RNA is provided, the strain comprising a) genomic DNA comprising at least one selectable phenotypic mutation; b) one or more nucleocapsids comprising proteins with RNA packaging and RNA polymerase activity; c) dsRNA sequences contained within said one or more nucleocapsids, said RNA sequences encoding at least: i) a gene product that complements said at least one selectable phenotypic mutation, and ii) an RNA of interest operably linked to a eukaryotic translation initiation sequence; and d) nucleic acid sequences encoding genes necessary for nucleocapsid production.

Another object of the present invention is to provide a method to generate rdsRNs, wherein recombinant RNA segments are introduced into bacterial packaging strains, packaged to form a recombinant nucleocapsid containing a eukaryotic translation expression cassette, thereby launching the rdsRNs de novo.

A further object of the present invention is to provide rdsRNs capable of stably replicating in a bacterial strain. In one embodiment, a recombinant double-strand RNA nucleocapsid (rdsRN) that comprises a) proteins with RNA packaging and RNA polymerase activity, and b) dsRNA sequences encoding at least: i) a gene product, and ii) an RNA of interest operably linked to a eukaryotic translation initiation sequence.

Yet another object of the present invention is to provide bacterial strains that stably produce rdsRNs that harbor one or more rdsRNA segments encoding a positive selection allele and functional eukaryotic translation expression cassettes.

A further object of this invention is to provide bacterial strains that stably produce rdsRNs that carry alphavirus expression cassettes, such as but not restricted to the Semliki forest virus (Berglund et al., Vaccine 17:497; 1999) or Venezuelan equine encephalitis (herein designated "VEE") virus (Davis et al., J Virol 70:3781; 1996); (Caley et al., J Virol 71:3031; 1997).

In yet another object of the current invention, methods are provided for the administration of rdsRNs to eukaryotic cells and tissues, and the use of rdsRNs to induce an immune response or to cause a biological effect in a target cell population.

Another object of the present invention is to provide live bacterial vectors that are capable of packaging rdsRNs.

Yet another object of the present invention is to provide live bacterial vectors that are capable of stably maintaining rdsRNs.

A further object of the present invention is to provide rdsRNs capable of replicating in a bacterial vector strain.

Still a further object of the current invention is to provide methods for the delivery of rdsRNs to mammalian cells and tissues.

Still a further object of the current invention is to provide methods for the use of said bacterial vectors carrying rdsRNs to induce an immune response or to cause a biological effect in a target cells or tissues.

The selectable phenotypic mutations harbored by the host bacteria of the invention are, in a preferred embodiment, non-reverting selectable phenotypic mutations.

A further object of the invention is to provide an electroporation medium comprising said bacteria and/or said dsRNs. In yet a further embodiment, various fluorinated RNAs which encode components of dsRNAs are provided.

These and other objects of the present invention will be apparent from the detailed description of the invention provided herein. As an exemplary embodiment, bacterial packaging strains, comprising sequences encoding segment-L of dsRP phi-8 that expresses procapsids in the strain and an asd mutation to enable selection and maintenance of the rdsRNs that express a functional asd gene in said strain are described. Further, a prototype rdsRN encoding vaccine antigens and reporters is described and the ability of said rdsRN to effect the expression of encoded antigens and reporters in a mammalian context is demonstrated.

DETAILED DESCRIPTION OF THE DRAWINGS

FIG. 1. Schematic representation of a bacterial cell containing a nucleocapsid, in which nucleic acid sequences that encode genes necessary for nucleocapsid production are located within dsRNA sequences inside nucleocapsid.

FIG. 2. Schematic representation of a bacterial cell containing a nucleocapsid, in which nucleic acid sequences that encode genes necessary for nucleocapsid production are located in the genomic DNA of the cell.

FIG. 3. Schematic representation of a bacterial cell containing a nucleocapsid, in which nucleic acid sequences that encode genes necessary for nucleocapsid production are located on a plasmid.

FIG. 4 shows the expression cassettes of various phi-8 recombinant segments-S and -M (rS, rS2 and rM, respectively). As configured in the Examples section below, the positive selection allele is the asd gene and the genes of interest encode candidate *Mycobacterium tuberculosis* antigens and the Hc-Red fluorescent protein. rS and rS2 were cloned into the PstI site of pT7/T3-18. rM was cloned as a KpnI/PstI fragment into the respective sites of pcDNA3.1$_{ZEO}$. All recombinant segments were placed under transcriptional control of the T7 promoter.

FIG. 7 provides the invasive characteristics of described packaging strains and parent strains.

Figure 8:
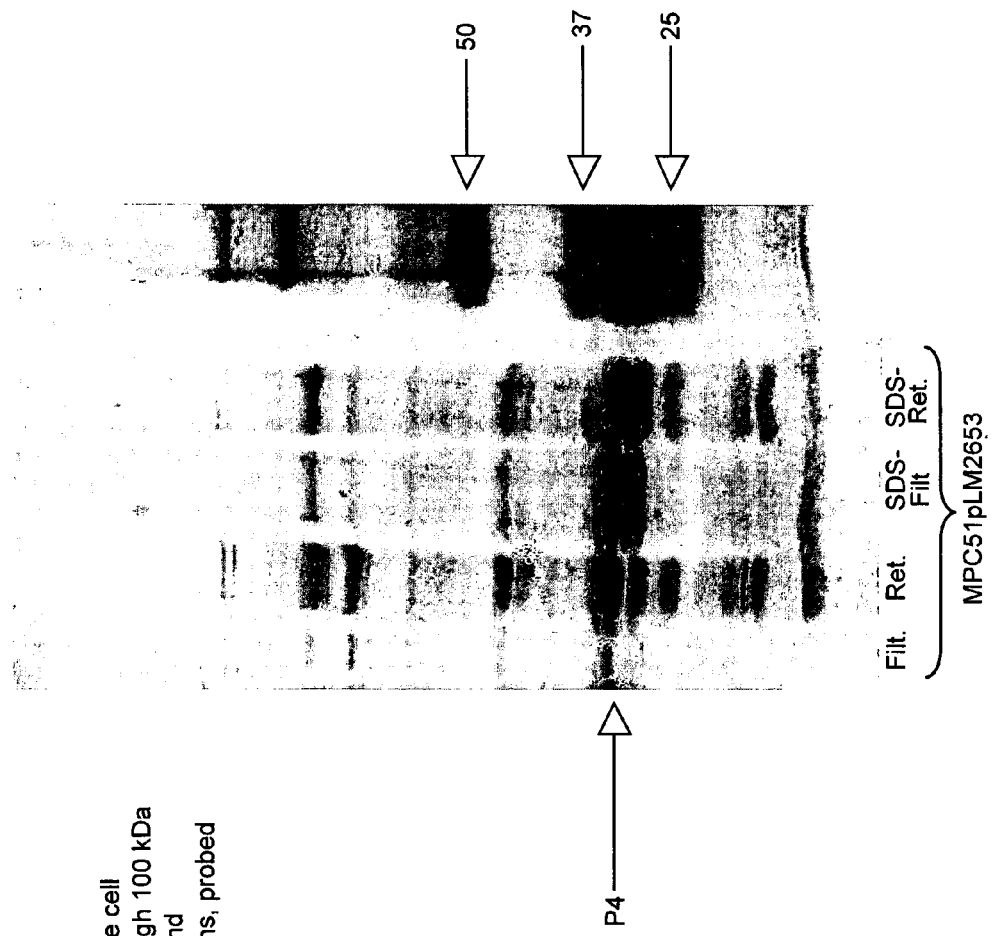

FIG. 8 is an immunoblot of whole cell lysates of *S. flexneri* MPC51pLM2653 before and after denaturation probed with procapsid-specific antisera demonstrating the in vivo assembly of procapsids.

Figure 9:
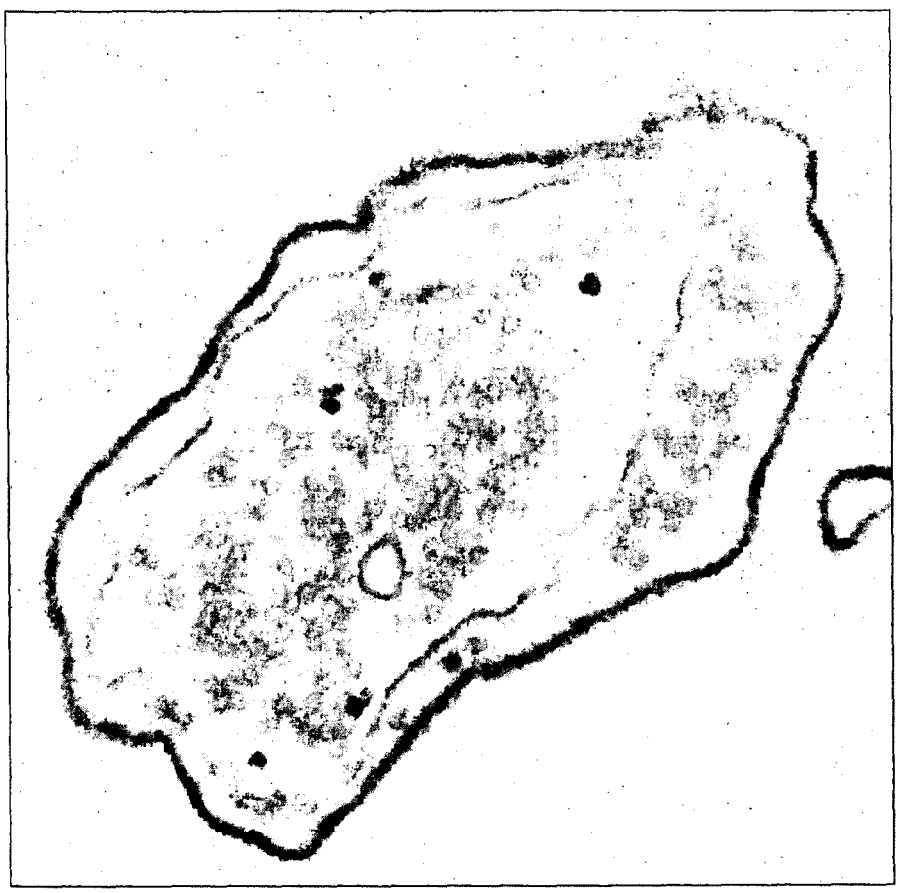
Figure 10:
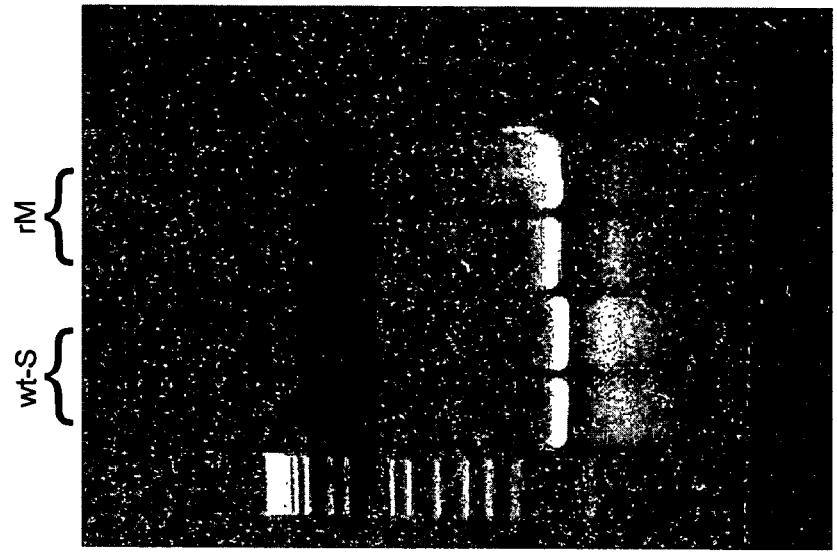

FIG. 9 is an electron micrograph of *S. flexneri* MPC51pLM2653 showing assembled procapsids FIG. 10 is an RT-PCR of packaged *S. flexneri* MPC51pLM2653 bearing the rdsRN designated LSMtb4 demonstrating the presence of (−) strand and (+) cDNA's indicative of second strand synthesis.

FIG. 11 is an electron micrograph of *S. flexneri* MPC51 bearing the self-replicating nucleocapsid LSMtb4.

FIG. 12 is an electron micrograph of *Pseudomonas syringae* bearing wild-type bacteriophage phi-8 reconstituted by electroporation of said strain with RNA encoding wild-type segments-S, -M, and -L.

FIG. 13 is a fluorescence micrograph of a HeLa cell 14 hours after invasion by *S. flexneri* MPC51 bearing rdsRN designated LSMtb4 probed with antigen85A specific antisera demonstrating the expression of antigen85A by a eukaryotic cell.

FIG. 14 is a fluorescence micrograph of a HeLa cell 12 hours after invasion by *S. flexneri* MPC51 bearing rdsRN designated LSMHc-Red demonstrating the direct fluorescence of Hc-Red protein translated from LSMHc-Red produced mRNA within the eukaryotic cell.

FIG. 15 is a fluorescence micrograph of a HeLa cell 12 hours after invasion by *S. flexneri* MPC51 bearing rdsRN designated LSMHc-Red probed with Hc-Red-specific antisera confirming the expression of the Hc-Red protein in the eukaryotic cell.

DETAILED DESCRIPTION OF THE PREFERRED EMBODIMENTS OF THE INVENTION

1. Construction of Bacterial Packaging Strains

The present invention provides bacterial packaging strains containing DNA sequences that encode and express functional double-stranded RNA phage/viral (dsRP) procapsid proteins in the strain, allowing the assembly of procapsids and packaging of dsRNA to form double-stranded RNA nucleocapsids (dsRNs) within the packaging strains. In addition, the dsRNA may be genetically engineered to contain sequences that encode and express a functional gene of interest, e.g. a transgene. The dsRNA is thus recombinant dsRNA (rdsRNA) and the nucleocapsids are recombinant dsRN (rdsRN). The packaging strains also contain a genetic mutation that creates a selectable, lethal deficiency in the strains. The rdsRNs are genetically engineered to encode and express a functional gene that complements the selectable deficiency created by the mutation, thereby enabling selection and maintenance of the rdsRNs within the bacterial packaging strains.

The following elements of the dsRNA phage are included in the rdsRN: segment-L; a segment-S pac sequence; segment-S RNA-dependent RNA polymerase recognition sequence; segment-M pac sequence; and segment-M RNA-dependent RNA polymerase recognition sequence. Positive selection alleles may be genetically engineered into the phage as follows: a positive selection allele may be linked, for example, to the ribosome binding site of gene-8 on segment-S or the ribosome binding site of gene-10 on segment-M, or both. Additional genes of interest may be genetically engineered into the S and/or M segments by substituting regions of the S and M segments that are not necessary for the production of functional dsRNs. Alternatively, the S and M segments may be eliminated entirely and substituted with sequences of interest. As used herein, "recombinant segments" refers to genetically engineered S and/or M segments, or the sequences of interest that replace the S and/or M segments.

While the system described herein would function using any double-stranded RNA phage or virus, the exemplary phi-8 rdsRN system described in the Examples section preferably utilizes the following elements of the cystoviridae genome(s) to function:

(i) segment-L and all the genes thereon,
(ii) pac sequences of segments-S and -M,
(iii) 3-prime terminal polymerase binding sequences of segments-S and -M.
(iv) gene 8 of segment-S In the phi-8 example, all coding sequences on segments-S and -M are deleted, with the exception of gene 8, and are not required for the rdsRN system to function. In addition, other exogenous sequences necessary or desirable for expression of the genes of interest may be included in the recombinant segments, such as IRES elements, Kozak and Shine-Dalgarno sequences for translation initiation in eukaryotes and prokaryotes, respectively, polyadenylation sequences, promoter sequences, enhancers, transcription terminators, leader peptide sequences, and molecular tags for protein purification, such as His tag.

According to the practice of the present invention, segment-L may be introduced into the bacterial packaging strain either in an extrachromosomal expression vector or by integration into the bacterial chromosome, and the recombinant segments are introduced into the bacterial packaging strain via electorporation, as described in detail below.

The bacterial strains from which the packaging strain is derived in the present invention is not critical thereto and include, but are not limited to: *Campylobacter* spp, *Neisseria* spp., *Haemophilus* spp, *Aeromonas* spp, *Francisella* spp, *Yersinia* spp, *Klebsiella* spp, *Bordetella* spp, *Legionella* spp, *Corynebacterium* spp, *Citrobacter* spp, *Chlamydia* spp, *Brucella* spp, *Pseudomonas* spp, *Helicobacter* spp, or *Vibrio* spp.

The particular *Campylobacter* strain employed is not critical to the present invention. Examples of *Campylobacter* strains that can be employed in the present invention include but are not limited to: *C. jejuni* (ATCC Nos. 43436, 43437, 43438), *C. hyointestinalis* (ATCC No. 35217), *C. fetus* (ATCC No. 19438) *C. fecalis* (ATCC No. 33709) *C. doylei* (ATCC No. 49349) and *C. coli* (ATCC Nos. 33559, 43133).

The particular *Yersinia* strain employed is not critical to the present invention. Examples of *Yersinia* strains which can be employed in the present invention include: *Y. enterocolitica* (ATCC No. 9610) or *Y. pestis* (ATCC No. 19428), *Y. enterocolitica* Ye03-R2 (al-Hendy et al., Infect. Immun., 60:870; 1992) or *Y. enterocolitica* aroA (O'Gaora et al., Micro. Path., 9:105; 1990).

The particular *Klebsiella* strain employed is not critical to the present invention. Examples of *Klebsiella* strains that can be employed in the present invention include *K. pneumoniae* (ATCC No. 13884).

The particular *Bordetella* strain employed is not critical to the present invention. Examples of *Bordetella* strains which can be employed in the present invention include *B. pertussis, B. bronchiseptica* (ATCC No. 19395).

The particular *Neisseria* strain employed is not critical to the present invention. Examples of *Neisseria* strains that can be employed in the present invention include *N. meningitidis* (ATCC No. 13077) and *N. gonorrhoeae* (ATCC No. 19424), *N. gonorrhoeae* MS11 aro mutant (Chamberlain et al., Micro. Path., 15:51-63; 1993).

The particular *Aeromonas* strain employed is not critical to the present invention. Examples of *Aeromonas* strains that can be employed in the present invention include *A. salminocida* (ATCC No. 33658), *A. schuberii* (ATCC No. 43700), *A. hydrophila, A. eucrenophila* (ATCC No. 23309).

The particular *Francisella* strain employed is not critical to the present invention. Examples of *Francisella* strains that can be employed in the present invention include *F. tularensis* (ATCC No. 15482).

The particular *Corynebacterium* strain employed is not critical to the present invention. Examples of *Corynebacterium* strains that can be employed in the present invention include *C. pseudotuberculosis* (ATCC No. 19410).

The particular *Citrobacter* strain employed is not critical to the present invention. Examples of *Citrobacter* strains that can be employed in the present invention include *C. freundii* (ATCC No. 8090).

The particular *Chlamydia* strain employed is not critical to the present invention. Examples of *Chlamydia* strains that can be employed in the present invention include *C. pneumoniae* (ATCC No. VR1310).

The particular *Haemophilus* strain employed is not critical to the present invention. Examples of *Haemophilus* strains that can be employed in the present invention include *H. influenzae* (Lee et al., J. Biol. Chem. 270:27151; 1995), *H. somnus* (ATCC No. 43625).

The particular *Brucella* strain employed is not critical to the present invention. Examples of *Brucella* strains that can be employed in the present invention include *B. abortus* (ATCC No. 23448).

The particular *Legionella* strain employed is not critical to the present invention. Examples of *Legionella* strains that can be employed in the present invention include *L. pneumophila* (ATCC No. 33156), or a *L. pneumophila* mip mutant (Ott, FEMS Micro. Rev., 14:161; 1994).

The particular *Pseudomonas* strain employed is not critical to the present invention. Examples of *Pseudomonas* strains that can be employed in the present invention include *P. aeruginosa* (ATCC No. 23267).

The particular *Helicobacter* strain employed is not critical to the present invention. Examples of *Helicobacter* strains that can be employed in the present invention include *H. pylori* (ATCC No. 43504), *H. mustelae* (ATCC No. 43772).

The particular *Vibrio* strain employed is not critical to the present invention. Examples of *Vibrio* strains that can be employed in the present invention include *Vibrio cholerae* (ATCC No. 14035), *Vibrio cincinnatiensis* (ATCC No. 35912), *V. cholerae* RSI virulence mutant (Taylor et al., J. Infect. Dis., 170:1518-1523; 1994) and *V. cholerae* ctxA, ace, zot, cep mutant (Waldor J et al., Infect Dis., 170:278-283; 1994).

In a preferred embodiment, the bacterial strain from which the packaging strain is developed in the present invention includes bacteria that possess the potential to serve both as packaging strain and as vaccine vectors, such as the Enterobacteriaceae, including but not limited to *Escherichia* spp, *Shigella* spp, and *Salmonella* spp. Gram-positive and acid-fast packaging and vector strains could similarly be constructed from *Listeria monocytogenes* or *Mycobacterium* spp.

The particular *Escherichia* strain employed is not critical to the present invention. Examples of *Escherichia* strains which can be employed in the present invention include *Escherichia coli* strains DH5α, HB 101, HS-4, 4608-58, 1184-68, 53638-C-17, 13-80, and 6-81 (See, e.g. Sambrook et al., supra; Grant et al., supra; Sansonetti et al., Ann. Microbiol. (Inst. Pasteur), 132A:351; 1982), enterotoxigenic *E. coli* (See, e.g. Evans et al., Infect. Immun., 12:656; 1975), enteropathogenic *E. coli* (See, e.g. Donnenberg et al., J. Infect. Dis., 169:831; 1994), enteroinvasive *E. coli* (See, e.g. Small et al., Infect Immun., 55:1674; 1987) and enterohemorrhagic *E. coli* (See, e.g. McKee and O'Brien, Infect. Immun., 63:2070; 1995).

The particular *Salmonella* strain employed is not critical to the present invention. Examples of *Salmonella* strains that can be employed in the present invention include *S. typhi* (see, e.g. ATCC No. 7251), *S. typhimurium* (see, e.g. ATCC No. 13311), *Salmonella galinarum* (ATCC No. 9184), *Salmonella enteriditis* (see, e.g. ATCC No. 4931) and *Salmonella typhimurium* (see, e.g. ATCC No. 6994). *S. typhi* aroC, aroD double mutant (see, e.g. Hone et al., Vacc., 9:810-816; 1991), *S. typhimurium* aroA mutant (see, e.g. Mastroeni et al., Micro. Pathol., 13:477-491; 1992).

The particular *Shigella* strain employed is not critical to the present invention. Examples of *Shigella* strains that can be employed in the present invention include *Shigella flexneri* (see, e.g. ATCC No. 29903), *Shigella flexneri* CVD1203 (see, e.g. Noriega et al., Infect. Immun. 62:5168; 1994), *Shigella flexneri* 15D (see, e.g. Sizemore et al., Science 270:299; 1995), *Shigella sonnei* (see, e.g. ATCC No. 29930), and *Shigella dysenteriae* (see, e.g. ATCC No. 13313).

The particular *Mycobacterium* strain employed is not critical to the present invention. Examples of *Mycobacterium* strains that can be employed in the present invention include *M. tuberculosis* CDC1551 strain (See, e.g. Griffith et al., Am. J. Respir. Crit. Care Med. August; 152(2):808; 1995), *M. tuberculosis* Beijing strain (Soolingen et al., 1995) H37Rv strain (ATCC#:25618), *M. tuberculosis* pantothenate auxotroph strain (Sambandamurthy, Nat. Med. 2002 8(10):1171; 2002), *M. tuberculosis* rpoV mutant strain (Collins et al., Proc Natl Acad Sci USA. 92(17):8036; 1995), *M. tuberculosis* leucine auxotroph strain (Hondalus et al., Infect. Immun. 68(5):2888; 2000), BCG Danish strain (ATCC # 35733), BCG Japanese strain (ATCC # 35737), BCG, Chicago strain (ATCC # 27289), BCG Copenhagen strain (ATCC #: 27290), BCG Pasteur strain (ATCC #: 35734), BCG Glaxo strain (ATCC #: 35741), BCG Connaught strain (ATCC # 35745), BCG Montreal (ATCC # 35746).

The particular *Listeria monocytogenes* strain employed is not critical to the present invention. Examples of *Listeria monocytogenes* strains which can be employed in the present invention include *L. monocytogenes* strain 10403S (e.g. Stevens et al., J Virol 78:8210-8218; 2004) or mutant *L. monocytogenes* strains such as (i) actA plcB double mutant (Peters et al., FEMS Immunology and Medical Microbiology 35: 243-253; 2003); (Angelakopoulous et al., Infect and Immunity 70: 3592-3601; 2002); (ii) dal dat double mutant for alanine racemase gene and D-amino acid aminotransferase gene (Thompson et al., Infect and Immunity 66: 3552-3561; 1998).

Having selected a strain that will serve as parent of the packaging strain, the strain is then genetically manipulated to introduce DNA sequences that express dsRP procapsids into said strain and introduce a mutation to enable selection and maintenance of the rdsRNs that express a functional gene that complements the mutation in said strain.

In general, the genes in segment-L encode the proteins necessary to generate fully functional procapsids, including the shell-encoding protein gene 8. However, for the phi-8 phage, gene 8 is located on segment S, and while the gene 8 product is not essential for assembly of a phi-8 procapsid, efficiently self-replicating phi-8 nuclsocapsids require a functional gene 8 product. Thus, when phi-8 phage is used in the practice of the invention, gene 8 of segment S is preferably included in the construct. For other phage, gene 8 activity is encoded on segment L, and thus the capacity to express segment-L mRNA is sufficient to produce functional nucleocapsids. The particular dsRP from which segment-L is obtained is not critical to the present invention and includes, but is not restricted to, one of Phi-6 Segment-L (Genbank accession no. M17461), Phi-13 Segment-L (Genbank accession no. AF261668), or Phi-8 Segment-L (Genbank accession no. AF226851), and are available from Dr. L. Mindich at Department of Microbiology, Public Health Research Institute, NY, N.Y.

Alternatively, cDNA sequences encoding segment-L can be generated synthetically using an Applied Biosystems ABI™ 3900 High-Throughput DNA Synthesizer (Foster City, Calif. 94404 U.S.A.) and procedures provided by the manufacturer. To synthesize the cDNA copies of segments-L and the recombinant segments-S and/or -M, a series of partial segments of the full-length sequence are generated by PCR and ligated together to form the full-length segment using procedures well know in the art (Ausubel et al., supra, 1990). Briefly, synthetic oligonucleotides 100-200 nucleotides in length (i.e. preferably with sequences at the 5'- and 3'ends that match at the 5' and 3' ends of the oligonucleotides that encodes the adjacent sequence) are produced using an automated DNA synthesizer (e.g. Applied Biosystems ABI™ 3900 High-Throughput DNA Synthesizer (Foster City, Calif. 94404 U.S.A.). Using the same approach, the complement oligonucleotides are synthesized and annealed with the complementary partners to form double stranded oligonucleotides. Pairs of double stranded oligonucleotides (i.e. those that encode adjacent sequences) are joined by ligation to form a larger fragment. These larger fragments are purified by agarose gel electrophoresis and isolated using a gel purification kit (E.g. The QIAEX® II Gel Extraction System, from Qiagen, Santa Cruz, Calif., Cat. No. 12385). This procedure is repeated until the full-length DNA molecule is created. After each round of ligation, the fragments can be amplified by PCR to increase the yield. Procedures for de novo synthetic gene construction are well known in the art, and are described elsewhere (Andre et al., supra, 1998); (Haas et al., supra, 1996); alternatively, synthetic genes can be purchased commercially, e.g. from the Midland Certified Reagent Co. (Midland, Tex.).

Although the present invention specifies the use of unaltered segment-L sequences, it will be apparent to those skilled in the art that modifications resulting in truncated or mutant derivatives of said sequences, but that do not prevent the formation of functional procapsids, can also be used without deviating substantively from the intent of the invention described herein.

The particular promoter used to express segment-L is not important to the present invention and can be any promoter that functions in the target strain, such as but not restricted to inducible promoters such $P_{BAD}$ (Genbank Accession No. X81838) and $P_{pagC}$ (Genbank Accession No. M55546) or constitutive promoters such a $P_{lpp}$ (Genbank Accession No. V00302) and $P_{ompA}$ (Genbank Accession No. X02006).

Segment-L can be introduced into the packaging strain in an expression vector, such as pT7/T3-18 (Ambion, Austin, Tex., Cat. No. 7201), or integrated into the chromosome by allelic exchange using methods known to those skilled in the art (E.g. PCR, DNA purification, restriction endonuclease digestion, agarose gel electrophoresis, ligation). The location of chromosomal integration is not important to the present invention, although in a preferred embodiment DNA encoding the segment-L expression cassette is integrated into the chromosome so as to inactivate a gene and generate a phenotype selectable under defined culture conditions (e.g. aroA (Genbank Accession No. X00557), aroC (Genbank Accession No. AY142231), leuD (Genbank Accession No. L06666) asd (Genbank Accession No. V00262), murI (Genbank Accession No. AY520970) kdsA (Genbank Accession No. AY174101), and htrB (Genbank Accession No. AF401529). Procedures for chromosomal integration and methods for culturing said mutants are well documented (Hamilton et al., J. Bacteriol. 171: 4617; 1989); (Blomfield et al., Mol. Microbiol. 5: 1447; 1991).

The particular mutation that is introduced into the packaging strain is not important to the present invention and can be any mutation that is capable of generating a selectable phenotype under defined culture conditions, such as but not restricted auxotrophic mutations such as aroA (Genbank Accession No. X00557), aroC (Genbank Accession No. AY142231), leuD (Genbank Accession No. L06666) or mutations in genes essential to cell wall synthesis such as asd (Genbank Accession No. V00262) or murI (Genbank Accession No. AY520970), or mutations that prevent growth at temperatures above 32° C., such as htrB (Genbank Accession No. AF401529).

Mutations can be introduced into the bacteria using any well-known genetic technique. These include but are not restricted to non-specific mutagenesis, using chemical agents such as N-methyl-N'-nitro-N-nitrosoguanidine, acridine orange, ethidium bromide, or non-lethal exposure to ultraviolet light (Miller (Ed), 1991, In: A short course in bacterial genetics, Cold Spring Harbor Press, Cold Spring Harbor, N.Y.). Alternatively, the mutations can be introduced using standard genetic techniques, such as Tn10 mutagenesis, bacteriophage-mediated transduction, lambda phage-mediated allelic exchange, or conjugational transfer (Miller (Ed), supra, 1991); (Hone, et al., J. Infect. Dis. 156:167; 1987); (Noriega, et al., Infect. Immun., 62:5168; 1994); (Hone, et al., Vaccine, 9:810; 1991); (Chatfield, et al., Vaccine 10:53; 1992); (Pickard, et al., Infect. Immun., 62:3984; 1994); (Odegaard, et al., J Biol Chem 272:19688; 1997); (Lee, et al., J. Biol. Chem., 270:27151; 1995); (Garrett, et al., J. Biol. Chem., 273:12457; 1998). The mutations can be a point mutation, a codon substitution, or, preferably, a non-reverting deletion mutation. The deletion mutations can be single base mutation up to deletion of the entire coding sequence. Deletion mutations have advantages in large scale mutations as such mutations import greater stability to the product.

The mutations can be either constitutively expressed or under the control of inducible promoters, such as the temperature sensitive heat shock family of promoters, or the anaerobically-induced nirB promoter (Harborne et al., Mol. Micro., 6:2805; 1992) or repressible promoters, such as uapA (Gorfinkiel et al., J. Biol. Chem., 268:23376; 1993) or gcv (Stauffer et al., J. Bact., 176:6159; 1994). Selection of the appropriate methodology will depend on the target strain and will be well understood to those skilled in the art.

The specific culture conditions for the growth of the bacterial vector strains that stably harbor rdsRNs are not critical to the present invention. For illustrative purposes, the mutants can be grown in a liquid medium such a TS medium (Difco, Detroit, Mich., Cat. No. 244620), Nutrient broth (Difco, Detroit, Mich., Cat. No. 233000), Tryptic Soy broth (Difco, Detroit, Mich., Cat. No. 211822), using conventional culture techniques that are appropriate for the bacterial strain being grown (Miller, supra, 1991). As an alternative, the bacteria can be cultured on solid media such as Nutrient agar (Difco, Detroit, Mich., Cat. No. 212000), Tryptic Soy agar (Difco, Detroit, Mich., Cat. No. 236920), or M9 minimal agar (Difco, Detroit, Mich., Cat. No. 248510).

*Mycobacterium* vaccine vector strains are cultured in liquid media, such as Middlebrook 7H9 (Difco, Detroit, Mich., Cat. No. 271310) or Saulton Synthetic Medium, preferably at 37° C. The strains can be maintained as static or agitated cultures. In addition, the growth rate of *Mycobacterium* can be enhanced by the addition of oleic acid (0.06% v/v; Research Diagnostics Cat. No. 01257) and detergents such as Tyloxapol (0.05% v/v; Research Diagnostics Cat. No. 70400). The purity of *Mycobacterium* cultures can be evaluated by evenly spreading 100 μl aliquots of the *Mycobacterium* culture serially diluted (E.g. 10-fold steps from Neat—$10^{-8}$) in phosphate buffered saline (herein referred to PBS) onto 3.5 inch plates containing 25-30 ml of solid media, such as Middlebrook 7H10 (BD Microbiology, Cockeyesville, Md., Cat. No. 221174).

The optical density at 600 nm at which the bacteria are harvested is not critical thereto, and can range from 0.1 to 5.0 and will be dependent on the specific strain, media and culture conditions employed.

2. Construction of rdsRNA Segments

As emphasized earlier, U.S. 20040132678 relies on helper phage (i.e. a wild type dsRP) to launch the production of rdsRPs. Under these conditions the methods provided in 20040132678 produce rdsRP that contain either wild-type segment-S or wild-type segment-M. Given that the lytic functions of dsRP are contained in segments-S and -M, it is not clear whether such configurations will be stable in large-scale production. It is also not clear how this methodology will separate the wild type dsRP from the rdsRP. Furthermore, 20040132678 provides no guidance on how to launch rdsRNs de novo, and how to generate and isolate stable carrier strains that harbor and replicate the rdsRNs. In contrast, the present invention pertains to the stable production of rdsRNs.

Typically, viral genomic size variations of up to about 10 percent are tolerated, which enables a degree of flexibility in the size of the genome in recombinant viral vectors (Domingo and Holland, *Annu. Rev. Microbiol.* 51:151; 1997). In the practice of the present invention, the size of the rdsRNA segment in the rdsRNs is equal to the sum of segments-S -M and -L plus or minus approximately 10%. To illustrate this point, phi-8 may be used as an example. The genome size of phi-8 is 14,984 bp, accordingly, to generate stable rdsRNs in packaging strains expressing segment-L of phi-8, the size of the recombinant segment(s) in such rdsRNs would be approximately 7933±1500 bp.

As will be shown below, this rule does not strictly apply, as it is possible to obtain rdsRNs derived from phi-8 that harbor only segment-L and a 4.5 kb rdsRNA segment-S (Sun et al., Virology, 308: 354; 2003). This suggests that rdsRNs are capable of a surprising degree of genomic flexibility. In the above described example, the recombinant segment-S was composed of sequences derived from both the wild-type segment-S and the wild-type segment-M. In this particular literature example, "derived from" (e.g. "derived from wild-type segment-S") describes sequences present in this recombinant rdsRNA construct that originate from the genomic sequence of the wild-type phage and are rearranged from their wild-type gene or coding feature order. Such sequences may be amplified from wild-type phage by RT-PCR and cloned, or chemically synthesized based on known sequences that occur in the wild type phage.

Figure 1:
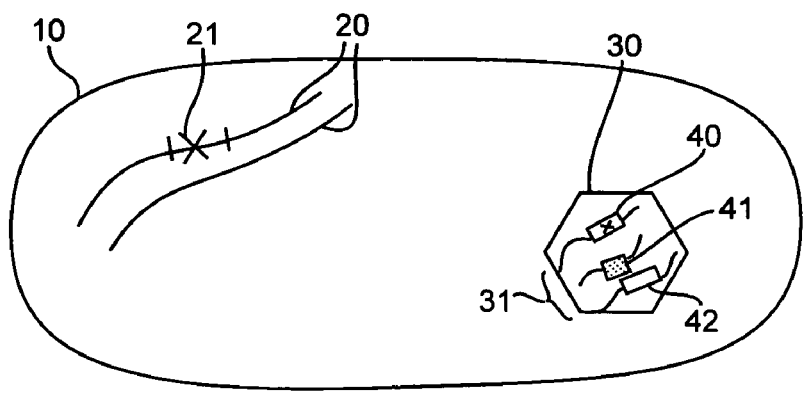
Figure 2:
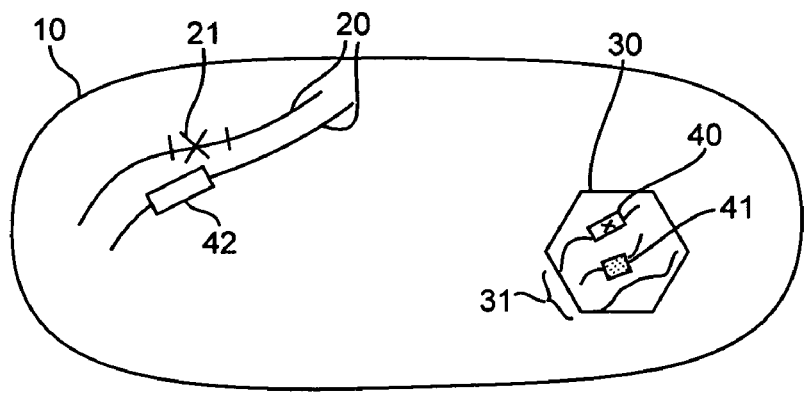
Figure 3:
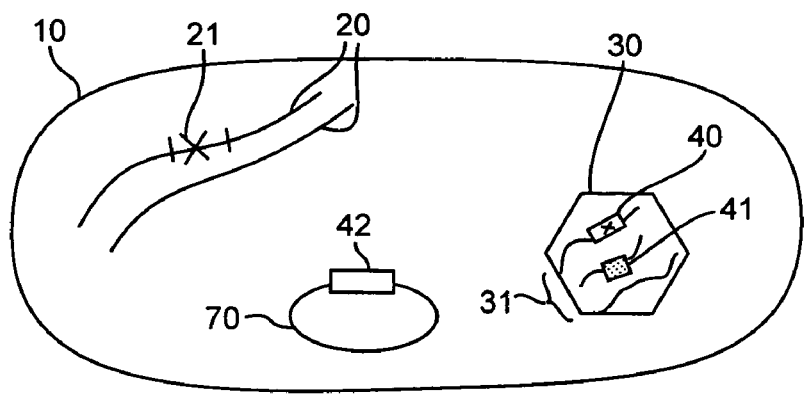
Figure 4:
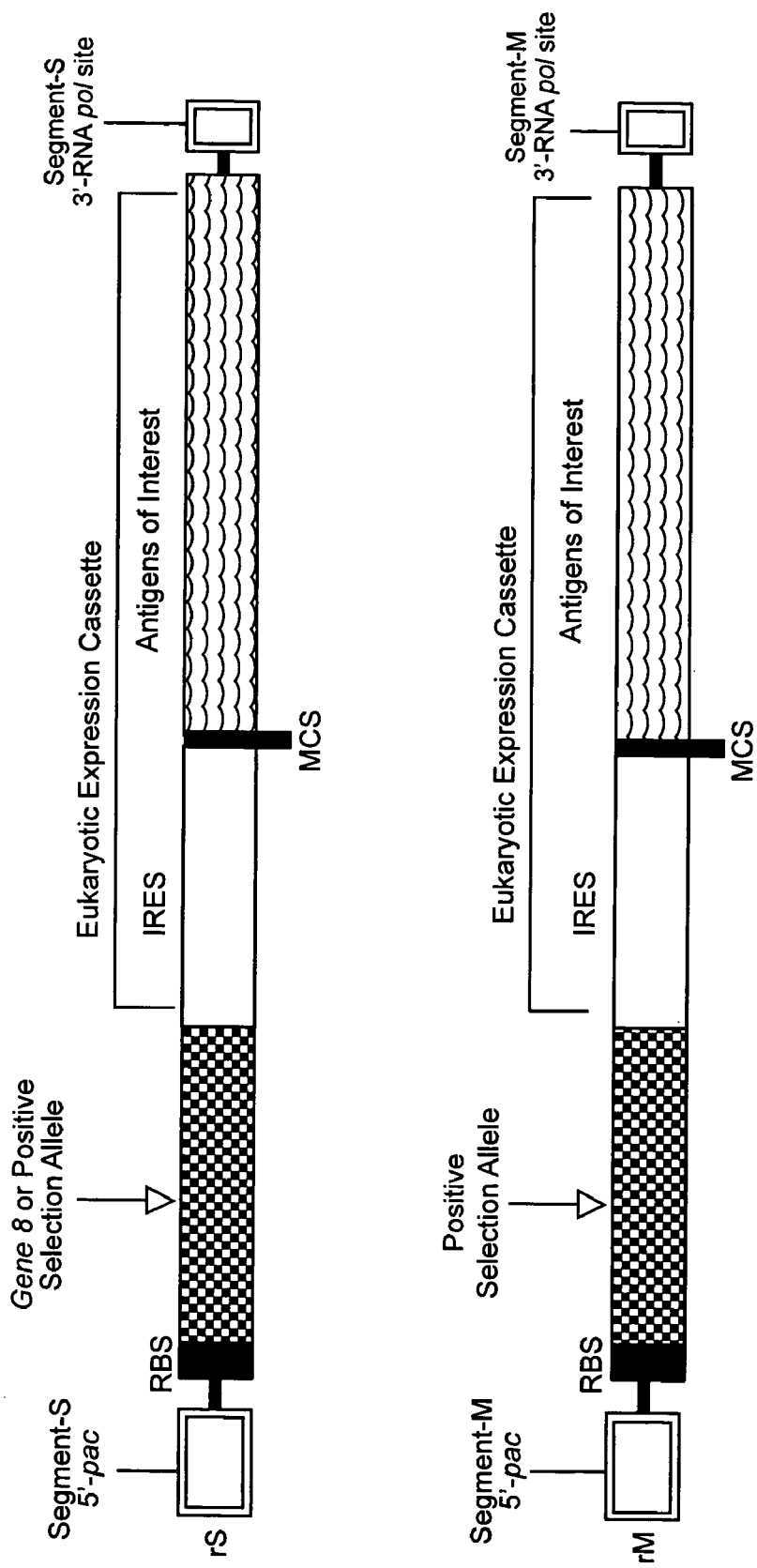

It is also possible to provide compositions that contain a genomic size that approaches the wild type genomic size. In one approach, a recombinant segment-S is generated that has a size of 7933±1500 bp. Another approach utilizes two rdsRNA segments, one containing segment-S packaging sequence and the other containing segment-M packaging sequence, wherein the total size of the recombinant segments is 7933±1500 bp (FIG. 4). In both approaches, at least one segment contains a positive selection allele and a single or both recombinant segments carry eukaryotic expression cassettes.

In a preferred embodiment, the components of rdsRNA segments can be assembled, for example, by joining the following cDNA and DNA sequences (FIG. 4):
rdsRNA Segment-S:
1. The φ-8 segment-S pac sequence and gene 8 (Hoogstraten et al., supra, 2000).
2. A positive selection allele linked to the ribosome binding site of gene 8 orf the wild-type segment-S. Gene 8 encodes a membrane protein which may remain associated with the nucleocapsid and is the first open reading froam of wild-type segment-S.
3. An IRES sequence with HpaI, EcoRI, SalI and NotI restriction endonuclease (RE) sites located 3-prime to the IRES sequence so that the HpaI (a blunt-end RE) provides an ATG start codon that is functionally linked to the IRES
4. The bovine poly-adenylation sequence (obtained from pcDNA3.1 (Invitrogen, Carlsbad, Calif., Cat. No. V860-20).
5. The ϕ-8 segment-S RNA-dependent RNA polymerase recognition sequence (Hoogstraten et al., supra, 2000).

rdsRNA Segment-M:

6. The ϕ-8 segment-M pac sequence (Hoogstraten et al., supra, 2000).
7. A positive selection allele linked to the ribosome binding site of gene-10. Gene 10 is the first open reading from of the wild-type segment-M and encodes a membrane protein of ϕ-8.
8. An IRES sequence with HpaI, EcoRI, SalI and NotI restriction endonuclease (RE) sites located 3-prime to the IRES sequence so that the HpaI (a blunt-end RE) provides an ATG start codon that is functionally linked to the IRES;
9. The bovine poly-adenylation sequence (obtained from pcDNA3.1 (Invitrogen, Carlsbad, Calif., Cat. No. V860-20).
10. The ϕ-8 segment-M RNA-dependent RNA polymerase recognition sequence (Hoogstraten et al., supra, 2000).

Although not wishing to be limited in scope by theory, it is likely that when the size of the rdsRNA segment-S is greater than 7900 $^{+}/-$1500 bp, the rdsRNA segment-M will no longer be packed, since a rdsRNA segment-S greater than 7900 $^{+}/-$1500 bp will induce a conformation change in the procapsid to enable recognition and uptake of segment-L, thereby generating a rdsRN with a genomic size $^{+}/-$10% that of the wild-type genome.

The cDNA sequences encoding the rdsRNA segments can be generated synthetically using an Applied Biosystems ABI™ 3900 High-Throughput DNA Synthesizer (Foster City, Calif.) and procedures provided by the manufacturer. To synthesize the cDNA copies of segments-L and the recombinant segments, a series of segments of the full-length sequence are generated by PCR and ligated together to form the full-length segment using procedures well know in the art (Ausubel et al., supra, 1990). Briefly, synthetic oligonucleotides 100-200 nucleotides in length (i.e. preferably with sequences at the 5'- and 3'ends that match at the 5' and 3' ends of the oligonucleotides that encodes the adjacent sequence) are produced using an automated DNA synthesizer (e.g. Applied Biosystems ABI™ 3900 High-Throughput DNA Synthesizer (Foster City, Calif.). Using the same approach, the complement oligonucleotides are synthesized and annealed with the complementary partners to form double stranded oligonucleotides. Pairs of double stranded oligonucleotides (i.e. those that encode adjacent sequences) are joined by ligation to form a larger fragment. These larger fragments are purified by agarose gel electrophoresis and isolated using a gel purification kit (E.g. The QIAEX® II Gel Extraction System, from Qiagen, Santa Cruz, Calif., Cat. No. 12385). This procedure is repeated until the full-length DNA molecule is created. After each round of ligation, the fragments can be amplified by PCR to increase the yield. Procedures for de novo synthetic gene construction are well known in the art, and are described elsewhere (Andre et al., supra, 1998); (Haas et al., supra, 1996); alternatively synthetic genes can be purchased commercially, e.g. from the Midland Certified Reagent Co. (Midland, Tex.).

Positive Selection Alleles

The particular positive selection allele that is incorporated into the rdsRNA segment is not important to the present invention, and can be any allele that is capable of restoring a dominant negative mutation in the packaging strain, such as but not restricted to genes that complement auxotrophic mutations such as aroA (Genbank Accession No. X00557), aroC (Genbank Accession No. AY142231), leuD (Genbank Accession No. L06666), or genes that complement mutations in genes essential to cell wall synthesis such as asd (Genbank Accession No. V00262), or murI (Genbank Accession No.

AY520970), or genes that complement mutations in genes essential to cell division such as ftsZ (Genbank Accession No. AF221946).

Source of IRES Sequences mRNA molecules lacking a 5' cap modifier, which is normally added in the nucleus to nuclear mRNA transcripts and enhances ribosome recognition, are poorly translated in eukaryotic cells unless an IRES sequence is present upstream of the gene of interest. The particular IRES employed in the present invention is not critical and can be selected from any of the commercially available vectors that contain IRES sequences or from any of the unencumbered sequences available. Thus, IRES sequences are widely available and can be obtained commercially from plasmid pIRES2-EGFP (Clontech, Palo Alto, Calif., Cat. No. 63206) by PCR using primers specific for the 5' and 3' ends of the IRES located at nucleotides 665-1251 in pIRES2-EGFP. The sequences in plasmid pIRES-EGFP can be obtained from the manufacturer (see the website located at clontech.com). A similar IRES can also be obtained from plasmid pCITE4a (Novagen, Madison, Wis., Cat. No. 69913; see also U.S. Pat. No. 4,937,190) by PCR using primers specific for the 5' and 3' ends of the CITE from nucleotides 16 to 518 in plasmid pCITE4a (the complete sequence of pCITE4a is available at the website located at novagen.com/docs/NDIS/69913-000.HTM); on plasmids pCITE4a-c; (U.S. Pat. No. 4,937,190); pSLIRES11 (Accession: AF171227); pPV (Accession # Y07702); pSVIRES-N (Accession #: AJ000156); (Creancier et al., J. Cell Biol., 10: 275-281; 2000); (Ramos and Martinez-Sala, RNA, 10:1374-1383; 1999); (Morgan et al., Nucleic Acids Res., 20:1293-1299; 1992); (Tsukiyama-Kohara et al., J. Virol., 66: 1476-1483; 1992); (Jang and Witmer et al., Genes Dev., 4: 1560-1572; 1990), or on the dicistronic retroviral vector (Accession Accession # D88622); or found in eukaryotic cells such as the fibroblast growth factor 2 IRES for stringent tissue-specific regulation (Creancier, et al., supra, 2000) or the Internal-ribosome-entry-site of the 3'-untranslated region of the mRNA for the beta subunit of mitochondrial H.sup.+-ATP synthase (Izquierdo and Cuezva, Biochem. J., 346:849; 2000). As there is no IP on the HCV IRES, plasmid pIRES-G (Hobbs, S. M. CRC Centre for Cancer Therapeutics, Institute of Cancer Research, Block F, 15, Cotswold Road, Belmont, Sutton, Surrey SM2 5NG, UK) may serve as the source of IRES and the sequence of this plasmid is available (Genebank accession no. Y11034).

Furthermore, an Internet search using an NCBI nucleotide database located at ncbi.nlm.nih.gov and using the search parameter "IRES not patent" yields 140 files containing IRES sequences. Finally, IRES cDNA can be made synthetically using an Applied Biosystems ABI™ 3900 High-Throughput DNA Synthesizer (Foster City, Calif.), using procedures provided by the manufacturer. To synthesize large IRES sequences such as the 502 bp IRES in pCITE4a, a series of segments are generated by PCR and ligated together to form the full-length sequence using procedures well know in the art (Ausubel et al., supra, 1990). Smaller IRES sequences such as the 53 bp IRES in hepatitis C virus (Genebank accession no. 1KH6A) can be made synthetically in a single round using an Applied Biosystems ABI™ 3900 High-Throughput DNA Synthesizer (Foster City, Calif.) and procedures provided by the manufacturer.

Examples of Heterologous Genes of Interest that can be Inserted in rdsRNs

In the present invention, the gene of interest introduced on a eukaryotic translation expression cassette into the rdsRN may encode an immunogen, and the rdsRN may thus function as a vaccine for eliciting an immune response against the immunogen. The imunogen may be either a foreign immunogen from viral, bacterial and parasitic pathogens, or an endogenous immunogen, such as but not limited to an autoimmune antigen or a tumor antigen. The immunogens may be the full-length native protein, chimeric fusions between the foreign immunogen and an endogenous protein or mimetic, a fragment or fragments thereof of an immunogen that originates from viral, bacterial and parasitic pathogens.

As used herein, "foreign immunogen" means a protein or fragment thereof, which is not normally expressed in the recipient animal cell or tissue, such as, but not limited to, viral proteins, bacterial proteins, parasite proteins, cytokines, chemokines, immunoregulatory agents, or therapeutic agents.

An "endogenous immunogen" means a protein or part thereof that is naturally present in the recipient animal cell or tissue, such as, but not limited to, an endogenous cellular protein, an immunoregulatory agent, or a therapeutic agent.

Apoptosis is programmed cell death and differs dramatically from necrotic cell death in terms of its induction and consequences. Apoptosis of cells containing foreign antigens is a powerful known stimulus of cellular immunity against such antigens. The process by which apoptosis of antigen containing cells leads to cellular immunity has sometimes been called cross-priming (Heath, W. R., et al., Immunol Rev 199:9; 2004, Gallucci, S. M et al., Nature Biotechnology. 5:1249; 1999, Albert, M. L. et al., Nature 392:86; 1988). There are several mechanisms for induction of apoptosis which lead to increased antigen specific cell mediated immunity. Caspase 8 mediated apoptosis leads to antigen specific cellular immune protection (Heath, W. R., et al., Immunol Rev 199:9; 2004). Expression of Caspase 8 by rdsRNs in the cytoplasm will be a powerful method for inducing programmed cell death in the context of foreign antigens expressed by rdsRN leading to high levels of antigen specific cellular immunity. Death receptor-5 (DR-5) also known as TRAIL-R2 (TRAIL receptor 2) or TNFR-SF-10B (Tumor Necrosis Factor-Superfamily member 10B) also mediates caspase 8 mediated apoptosis (Sheridan, J. P., et al., Science 277:818; 1997). Reovirus induced apoptosis is mediated by TRAIL-DR5 leading to subsequent clearance of the virus (Clarke, P. S. et al., J. Virol; 2000). Expression of DR-5 by rdsRNs should provide a potent adjuvant effect for induction of antigen specific cellular immunity against rdsRN expressed antigens. Antigen expressing cells can also be induced to undergo apoptosis through Fas ligation, which is a strong stimulus for induction of antigen specific cellular immune responses (Chattergoon, M. A. et al., Nat Biotechnology 18:974; 2000). rdsRNs expressing Fas or Fas cytoplasmic domain/CD4 extodomain fusion protein will induce apoptosis and antigen specific cellular immune responses against antigens expressed by rdsRNs.

The enhancement of cellular immunity by rdsRNs mediated apoptosis described above is not limited to antigens specifically coded for by the rdsRN itself but includes any antigen in the cell where the rdsRNs express specific mediators of apoptosis. As an example, if rdsRNs are delivered to tumor cells where apoptosis is induced then cellular immunity against important tumor antigens will be induced with elimination, reduction or prevention of the tumor and/or metastasis.

In a further embodiment of this invention if rdsRNs, with or without the capacity to induce apoptosis and with the ability to code for and produce foreign antigens against which strong cellular immune responses will be mounted, are delivered inside tumor or other cells strong cellular responses against those cells will be produced. These cellular responses will lead to immune mediated tumor cell destruction, further cross priming and induction of cellular immunity against tumor or other important antigens with subsequent elimination, reduction or prevention of the tumor and/or metastasis. An example of such a foreign antigen is an HLA antigen different from the host cell HLA against which a strong heterologous cellular response will be mounted.

Recombinant rdsRNs capable of inducing apoptosis and delivering specific tumor antigens will induce strong antigen specific cellular responses against these tumor antigens, including breaking of some tolerance for these antigens leading to elimination, reduction or prevention of tumors and/or metastasis without the need for direct delivery of the rdsRNs into the tumor itself.

Apoptosis following DNA damage or caspase 9 induces tolerance to certain antigens. (Hugues, S. E., et al., Immunity 16:169; 2002). Induction of tolerance is important in controlling or preventing autoimmune diseases such as but not limited to diabetes, rheumatoid arthritis, Crohns disease, imflammatory bowel disease and multiple sclerosis. Production of caspase 9 or other apoptosis mediated tolerance inducing proteins by rdsRNs in cells such as but not limited to β pancreatic cells, colorectal and nerve cells will produce limited apoptosis which will induce tolerance against the antigen targets of autoimmunity in those cells thereby treating or preventing the autoimmune disease condition. Identification of specific antigens involved in autoimmune reactions will allow induction of tolerance against these autoimmune target antigens through rdsRNs production of these antigens and Caspase 9 or other molecules capable of inducing apoptotic mediated tolerance that will lead to treatment and/or prevention of these autoimmune diseases.

Another embodiment of the present invention, therefore, provides rdsRN which encode at least one gene which expresses a protein that promotes apoptosis, such as but not limited to expression of *Salmonella* SopE (Genbank accession no. AAD54239, AAB51429 or AAC02071), *Shigella* IpaB (Genbank accession no. AAM89553 or AAM89536), caspase-8 (Genbank accession no. AAD24962 or AAH06737), etc., in the cytoplasm of host cells and imparts a powerful method for inducing programmed cell death in the context of antigens expressed by said rdsRN, thereby invoking high-level T cell-mediated immunity to the target antigens. Alternatively, rdsRN can be produced which encode at least one gene which expresses DR-5, such as human DR-5 (Genbank accession # BAA33723), herpesvirus-6 (HHV-6) DR-5 homologue (Genbank accession # CAA58423) etc., thereby providing a potent adjuvant effect for induction of antigen-specific cellular immunity against the target antigens.

Alternatively or additionally, the immunogen may be encoded by a synthetic gene and may be constructed using conventional recombinant DNA methods (See above).

The foreign immunogen can be any molecule that is expressed by any viral, bacterial, or parasitic pathogen prior to or during entry into, colonization of, or replication in their animal host; the rdsRN may express immunogens or parts thereof that originate from viral, bacterial and parasitic pathogens. These pathogens can be infectious in humans, domestic animals or wild animal hosts.

The viral pathogens, from which the viral antigens are derived, include, but are not limited to, Orthomyxoviruses, such as influenza virus (Taxonomy ID: 59771; Retroviruses, such as RSV, HTLV-1 (Taxonomy ID: 39015), and HTLV-II (Taxonomy ID: 11909), Papillomaviridae such as HPV (Taxonomy ID: 337043), Herpesviruses such as EBV Taxonomy ID: 10295); CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picornoviruses, such as Poliovirus (Taxonomy ID: 12080); Poxviruses, such as vaccinia (Taxonomy ID: 10245); Rotavirus (Taxonomy ID: 10912); and Parvoviruses, such as adeno-associated virus 1 (Taxonomy ID: 85106).

Examples of viral antigens can be found in the group including but not limited to the human immunodeficiency virus antigens Nef (National Institute of Allergy and Infectious Disease HIV Repository Cat. # 183; Genbank accession # AF238278), Gag, Env (National Institute of Allergy and Infectious Disease HIV Repository Cat. # 2433; Genbank accession # U39362), Tat (National Institute of Allergy and Infectious Disease HIV Repository Cat. # 827; Genbank accession # M113137), mutant derivatives of Tat, such as Tat-Δ31-45 (Agwale et al., Proc. Natl. Acad. Sci. USA 99:10037; 2002), Rev (National Institute of Allergy and Infectious Disease HIV Repository Cat. # 2088; Genbank accession # L14572), and Pol (National Institute of Allergy and Infectious Disease HIV Repository Cat. # 238; Genbank accession # AJ237568) and T and B cell epitopes of gp120 (Hanke and McMichael, AIDS Immunol Lett., 66:177; 1999); (Hanke, et al., Vaccine, 17:589; 1999); (Palker et al., J. Immunol., 142:3612-3619; 1989) chimeric derivatives of HIV-1 Env and gp120, such as but not restricted to fusion between gp120 and CD4 (Fouts et al., J. Virol. 2000, 74:11427-11436; 2000); truncated or modified derivatives of HIV-1 env, such as but not restricted to gp140 (Stamatos et al., J Virol, 72:9656-9667; 1998) or derivatives of HIV-1 Env and/or gp140 thereof (Binley, et al., J Virol, 76:2606-2616; 2002); (Sanders, et al., J Virol, 74:5091-5100 (2000); (Binley, et al. J Virol, 74:627-643; 2000), the hepatitis B surface antigen (Genbank accession # AF043578); (Wu et al., Proc. Natl. Acad. Sci., USA, 86:4726-4730; 1989); rotavirus antigens, such as VP4 (Genbank accession # AJ293721); (Mackow et al., Proc. Natl. Acad. Sci., USA, 87:518-522; 1990) and VP7 (GenBank accession # AY003871); (Green et al., J. Virol., 62:1819-1823; 1988), influenza virus antigens such as hemagglutinin or (GenBank accession # AJ404627); (Pertmer and Robinson, Virology, 257:406; 1999); nucleoprotein (GenBank accession # AJ289872); (Lin et al., Proc. Natl. Acad. Sci., 97: 9654-9658; 2000) herpes simplex virus antigens such as thymidine kinase (Genbank accession # AB047378; (Whitley et al., In: New Generation Vaccines, pages 825-854).

The bacterial pathogens, from which the bacterial antigens are derived, include but are not limited to: *Mycobacterium* spp., *Helicobacter pylori*, *Salmonella* spp., *Shigella* spp., *E. coli*, *Rickettsia* spp., *Listeria* spp., *Legionella pneumoniae*, *Pseudomonas* spp., *Vibrio* spp., *Bacillus anthracis* and *Borellia burgdorferi*.

Examples of protective antigens of bacterial pathogens include the somatic antigens of enterotoxigenic *E. coli*, such as the CFA/I fimbrial antigen (Yamamoto et al., Infect. Immun., 50:925-928; 1985) and the nontoxic B-subunit of the heat-labile toxin (Klipstein et al., Infect. Immun., 40:888-893; 1983); pertactin of *Bordetella pertussis* (Roberts et al., Vacc., 10:43-48; 1992), adenylate cyclase-hemolysin of *B. pertussis* (Guiso et al., Micro. Path., 11:423-431; 1991), fragment C of tetanus toxin of *Clostridium tetani* (Fairweather et al., Infect. Immun., 58:1323-1326; 1990), OspA of *Borellia burgdorferi* (Sikand et al., Pediatrics, 108:123-128; 2001); (Wallich et al., Infect Immun, 69:2130-2136; 2001), protective paracrystalline-surface-layer proteins of *Rickettsia prowazekii* and *Rickettsia typhi* (Carl et al., Proc Natl Acad Sci USA, 87:8237-8241; 1990), the listeriolysin (also known as "Llo" and "Hly") and/or the superoxide dismutase (also know as "SOD" and "p60") of *Listeria monocytogenes* (Hess, J., et al., Infect. Immun. 65:1286-92; 1997); Hess, J., et al., Proc. Natl. Acad. Sci. 93:1458-1463; 1996); (Bouwer et al., J. Exp. Med. 175:1467-71; 1992), the urease of *Helicobacter pylori* (Gomez-Duarte et al., Vaccine 16, 460-71; 1998); (Corthesy-Theulaz, et al., Infection & Immunity 66, 581-6; 1998), and the *Bacillus anthracis* protective antigen and lethal factor receptor-binding domain (Price, et al., Infect. Immun. 69, 4509-4515; 2001).

The parasitic pathogens, from which the parasitic antigens are derived, include but are not limited to: *Plasmodium* spp., such as *Plasmodium falciparum* (ATCC#: 30145); *Trypanosome* spp., such as *Trypanosoma cruzi* (ATCC#: 50797); *Giardia* spp., such as *Giardia intestinalis* (ATCC#: 30888D); *Boophilus* spp., *Babesia* spp., such as *Babesia microti* (ATCC#: 30221); *Entamoeba* spp., such as *Entamoeba histolytica* (ATCC#: 30015); *Eimeria* spp., such as *Eimeria maxima* (ATCC# 40357); *Leishmania* spp. (Taxonomy ID: 38568); *Schistosome* spp., *Brugia* spp., *Fascida* spp., *Dirofilaria* spp., *Wuchereria* spp., and *Onchocerea* spp.

Examples of protective antigens of parasitic pathogens include the circumsporozoite antigens of *Plasmodium* spp. (Sadoff et al., Science, 240:336-337; 1988), such as the circumsporozoite antigen of *P. bergerii* or the circumsporozoite antigen of *P. falciparum*; the merozoite surface antigen of *Plasmodium* spp. (Spetzler et al., Int. J. Pept. Prot. Res., 43:351-358; 1994); the galactose specific lectin of *Entamoeba histolytica* (Mann et al., Proc. Natl. Acad. Sci., USA, 88:3248-3252; 1991), gp63 of *Leishmania* spp. (Russell et al., J. Immunol., 140:1274-1278; 1988); (Xu and Liew, Immunol., 84: 173-176; 1995), gp46 of *Leishmania major* (Handman et al., Vaccine, 18:3011-3017; 2000) paramyosin of *Brugia malayi* (Li et al., Mol. Biochem. Parasitol., 49:315-323; 1991), the triose-phosphate isomerase of *Schistosoma mansoni* (Shoemaker et al., Proc. Natl. Acad. Sci., USA, 89:1842-1846; 1992); the secreted globin-like protein of *Trichostrongylus colubriformis* (Frenkel et al., Mol. Biochem. Parasitol., 50:27-36; 1992); the glutathione-S-transferase's of *Frasciola hepatica* (Hillyer et al., Exp. Parasitol., 75:176-186; 1992), *Schistosoma bovis* and *S. japonicum* (Bashir et al., Trop. Geog. Med., 46:255-258; 1994); and KLH of *Schistosoma bovis* and *S. japonicum* (Bashir et al., supra, 1994).

As mentioned earlier, the rdsRN vaccine may encode an endogenous immunogen, which may be any cellular protein, immunoregulatory agent, or therapeutic agent, or parts thereof, that may be expressed in the recipient cell, including but not limited to tumor, transplantation, and autoimmune immunogens, or fragments and derivatives of tumor, transplantation, and autoimmune immunogens thereof. Thus, in the present invention, dsRP may encode tumor, transplant, or autoimmune immunogens, or parts or derivatives thereof. Alternatively, the dsRP may encode synthetic genes (made as described above), which encode tumor-specific, transplant, or autoimmune antigens or parts thereof.

Examples of tumor specific antigens include prostate specific antigen (Gattuso et al., Human Pathol., 26:123-126; 1995), TAG-72 and CEA (Guadagni et al., Int. J. Biol. Markers, 9:53-60; 1994), MAGE-1 and tyrosinase (Coulie et al., J. Immunothera., 14:104-109; 1993). Recently it has been shown in mice that immunization with non-malignant cells expressing a tumor antigen provides a vaccine effect, and also helps the animal mount an immune response to clear malignant tumor cells displaying the same antigen (Koeppen et al., Anal. N.Y. Acad. Sci., 690:244-255; 1993).

Examples of transplant antigens include the CD3 molecule on T cells (Alegre et al., Digest. Dis. Sci., 40:58-64; 1995).

Treatment with an antibody to CD3 receptor has been shown to rapidly clear circulating T cells and reverse cell-mediated transplant rejection (Alegre et al., supra, 1995).

Examples of autoimmune antigens include IAS β chain (Topham et al., Proc. Natl. Acad. Sci., USA, 91:8005-8009; 1994). Vaccination of mice with an 18 amino acid peptide from IAS β chain has been demonstrated to provide protection and treatment to mice with experimental autoimmune encephalomyelitis (Topham et al., supra, 1994).

In addition, rdsRNA segments can be constructed that encode an adjuvant, and can be used to increase host immune responses to immunogens. The particular adjuvant encoded by the rdsRNA is not critical to the present invention and may be the A subunit of cholera toxin (i.e. CtxA; GenBank accession no. X00171, AF175708, D30053, D30052,), or parts and/or mutant derivatives thereof (e.g. the A1 domain of the A subunit of Ctx (i.e. CtxA1; GenBank accession no. K02679), from any classical *Vibrio cholerae* (e.g. *V. cholerae* strain 395, ATCC # 39541) or El Tor *V. cholerae* (E.g. *V. cholerae* strain 2125, ATCC # 39050) strain. Alternatively, any bacterial toxin that is a member of the family of bacterial adenosine diphosphate-ribosylating exotoxins (Krueger and Barbier, Clin. Microbiol. Rev., 8:34; 1995), may be used in place of CtxA; for example, the A subunit of heat-labile toxin (referred to herein as EltA) of enterotoxigenic *Escherichia coli* (GenBank accession # M35581), pertussis toxin S1 subunit (E.g. ptxS1, GenBank accession # AJ007364, AJ007363, AJ006159, AJ006157, etc.); as a further alternative, the adjuvant may be one of the adenylate cyclase-hemolysins of *Bordetella pertussis* (ATCC # 8467), *Bordetella bronchiseptica* (ATCC # 7773) or *Bordetella parapertussis* (ATCC # 15237), e.g. the cyaA genes of *B. pertussis* (GenBank accession no. X14199), *B. parapertussis* (GenBank accession no. AJ249835) or *B. bronchiseptica* (GenBank accession no. Z37112).

Cytokine encoding rdsRNA segments can also be constructed. The particular cytokine encoded by the rdsRNA is not critical to the present invention includes, but not limited to, interleukin-4 (herein referred to as "IL-4"; Genbank accession no. AF352783 (Murine IL-4) or NM_000589 (Human IL-4), IL-5 (Genbank accession no. NM_010558 (Murine IL-5) or NM_000879 (Human IL-5), IL-6 (Genbank accession no. M20572 (Murine IL-6) or M29150 (Human IL-6), IL-10 (Genbank accession no. NM_010548 (Murine IL-10) or AF418271 (Human IL-10), Il-12$_{p40}$ (Genbank accession no. NM_008352 (Murine IL-12 p40) or AY008847 (Human IL-12 p40), IL-12$_{p70}$ (Genbank accession no. NM_008351/NM_008352 (Murine IL-12 p35/40) or AF093065/AY008847 (Human IL-12 p35/40), TGFβ (Genbank accession no. NM_011577 (Murine TGFβ1) or M60316 (Human TGFβ1), and TNFα Genbank accession no. X02611 (Murine TNFα) or M26331 (Human TNFα).

Furthermore, small inhibitory RNA's or antisense RNA's may also be encoded in rdsRNA segments for regulation of protein expression in targeted tissues.

Recombinant DNA and RNA procedures for the introduction of functional expression cassettes to generate rdsRNA capable of expressing an immunoregulatory agent in eukaryotic cells or tissues are described above.

As exemplary vaccine constructs to be encoded in eukaryotic expression cassettes, virus-like particles (Herein "VLP") can be constructed to induce produce protective immune responses against viral pathogens. Influenza VLP's have been shown to self assemble following plasmid expression of gene sequences encoding the hemaglutinin (HA), neuramimidase (NA), and the matrix proteins (M1 and M2) (Latham et al., J. Virol, 75:6154-6165; 2001). VLP's so constructed are further capable of membrane fusion and budding to further potentiate antibody-producing immune responses and protective immunity in animal models (Pushko et al., Vaccine. 2005 Sep. 2; [Epub ahead of print]). HIV VLP's can be similarly assembled from minimal sequences encoding amino acids 146-231 of the capsid protein, a six amino acid myristylation sequence, the sequence encoding the P2 peptide, a GCN4 leucine zipper domain, and the gp160 envelope precursor (Accola et al., J. Virol, 74:5395-5402; 2000). The major protein LI of HPV has been shown to self-assemble into VLP's a variety of cell lines and produces humoral and cellular immunity, making the gene encoding this protein an attractive immunogen (Shi et al., J. Virol., 75(21): 10139-10148; 2001).

3. Construction of rdsRNA Segments that Carry Alphavirus Expression Cassettes

Figure 5:
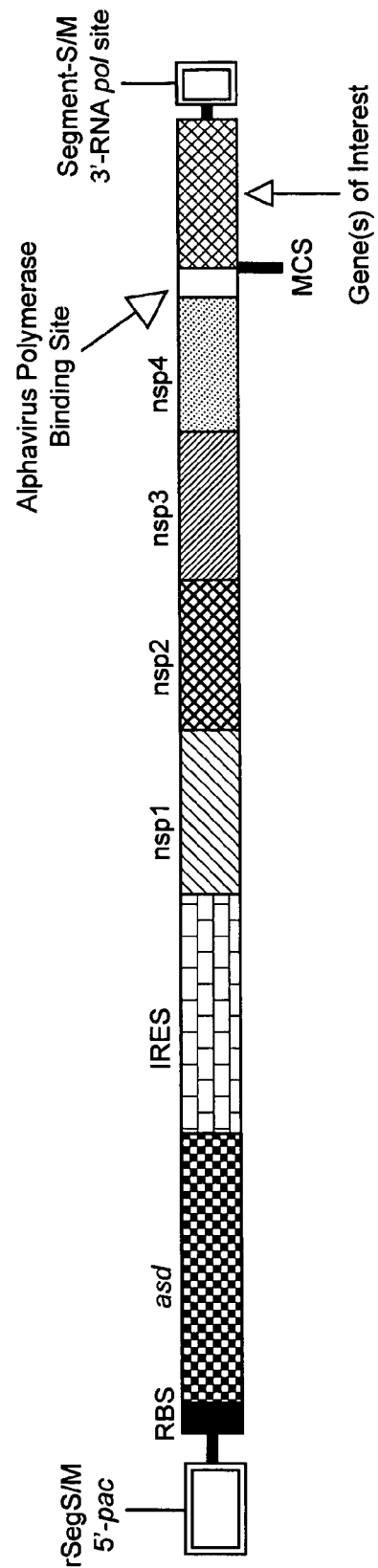
FIG. 5 shows an rS expression cassette that includes an alphavirus (Semliki Forest Virus) self-amplifying replicon (nsp1-4 and replicase binding sequence).

As noted above, rdsRNs can harbor a mammalian translation expression cassette comprised of the semliki forest virus (herein referred to as "SFV") self-amplifying replicon from plasmid pSFV1 (Invitrogen Inc., Carlsbad, Calif.) functionally linked to a gene of interest. Genes encoding SFV nonstructural protein 1-4 (herein referred to as "nsp1-4") and the replicase recognition site in pSFV1 are amplified by PCR and inserted by blunt-end ligation into the HpaI site immediately downstream and functionally linked to the IRES in rSeg-S resulting in rSeg-S::SFV1 (FIG. 5). A SmaI RE site in plasmid rSeg-S::SFV1 can serve as an insertion site for any foreign or endogenous gene of interest, such as those outlined above.

Note that in rdsRNs that harbor rdsRNA segment-S containing a positive selection allele and an alphavirus nsp1-4 and amplicon about 8100 bp, the uptake of segment-L will be impeded when the gene of interest exceeds 800 bp (i.e. the genome size is more than 10 percent greater that the wild-type genome). Note that in all circumstances, rdsRNs that harbor rdsRNA segment-S containing a positive selection allele and an alphavirus nsp1-4 and amplicon do not need a rdsRNA segment-M.

This limitation in capacity can be solved by generating packaging strains that express modified derivatives of segment-L that lack the 5-prime pac sequence. Such sequences will express the proteins necessary for procapsid production but will not be packaged in the nucleocapsid, thereby providing an additional 7000 bp of capacity in the rdsRN generated in said strain.

The modified segment-L in such constructs can be introduced into the packaging strain in an expression vector, such as pT7/T3-18 (Ambion, Austin, Tex., Cat. No. 7201) or integrated into the chromosome by allelic exchange using methods known to those skilled in the art (Hamilton et al., supra, 1989); (Blomfield et al., supra, 1991). The location of chromosomal integration is not important to the present invention, although in a preferred embodiment DNA encoding the segment-L expression cassette is integrated into the chromosome so as to inactivate a gene and generate a phenotype selectable under defined culture conditions, such as aroA (Genbank Accession No. X00557), aroC (Genbank Accession No. AY142231), leuD (Genbank Accession No. L06666) asd (Genbank Accession No. V00262), murI (Genbank Accession No. AY520970) kdsA (Genbank Accession No. AY174101), and htrB (Genbank Accession No. AF401529). Procedures for chromosomal integration and methods for culturing said mutants are well documented (Hamilton et al., J. Bacteriol. 171: 4617; 1989); (Blomfield et al., Mol. Microbiol. 5: 1447; 1991).

4. Methods to Generate rdsRNs De Novo

Figure 6:
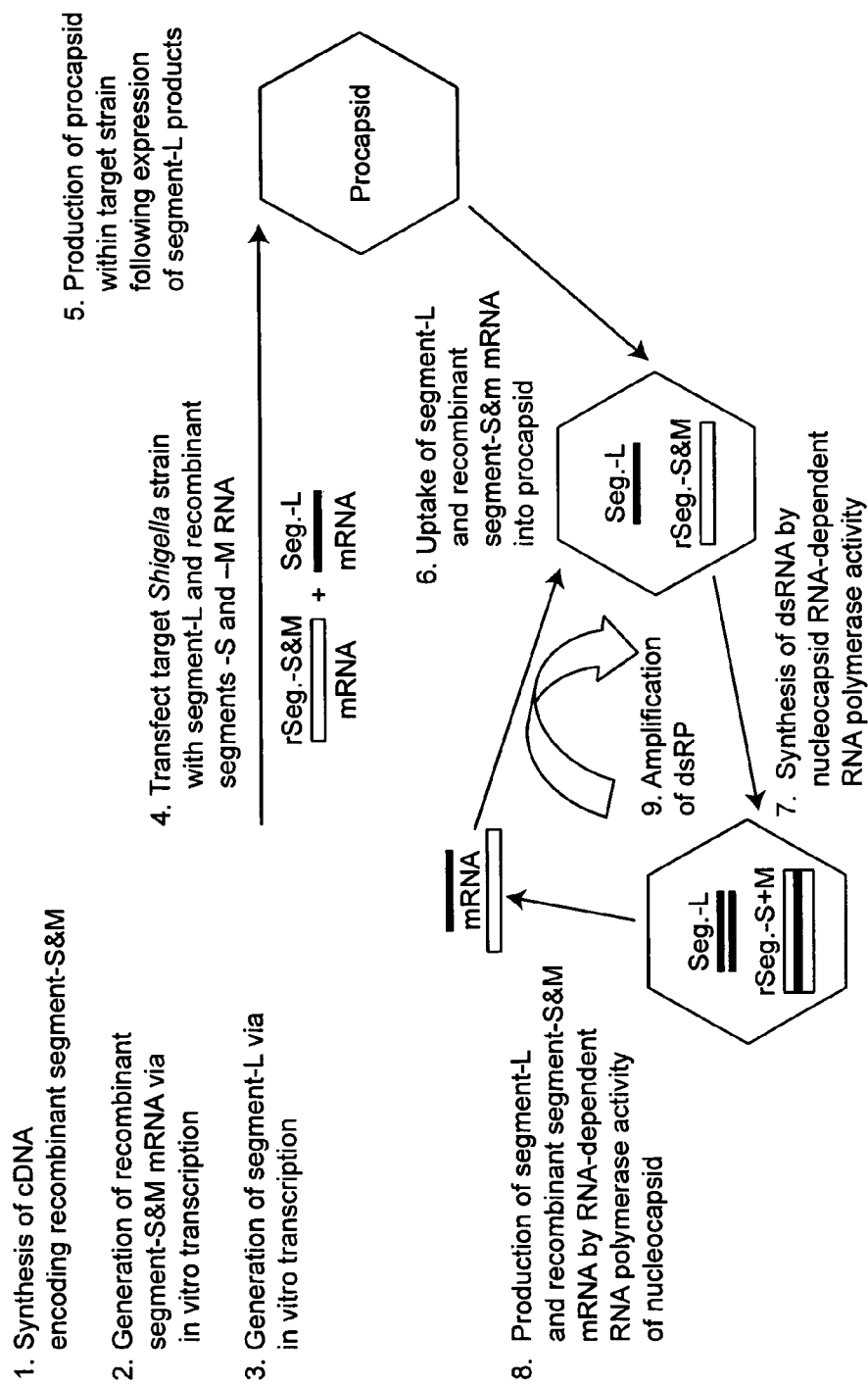
FIG. 6 is a schematic of the development and function of a bacterial packaging strain.

The rdsRNs are produced in packaging strains by introducing RNA encoding all of the information necessary to produce the rdsRNA following uptake into the procapsid. The rRNA may be directly introduced or may be encoded on non-replicating plasmids, which may be co-introduced into the packaging strain. The genes encoding segment-L and hence the procapsid may be present in the packaging strain on a plasmid or be integrated into the chromosome of the packaging strain. As a further option, the positive strand RNA encoding segment-L may be introduced into the packaging strain in concert with positive strand RNA encoding recombinant segments-S and -M. Once the procapsid incorporates the recombinant ssRNA's (herein referred to as ssRNA) of segments-S and -M, which must be of sufficient size and display the appropriate packaging sequences to produce a signal for the uptake of segment-L mRNA, the latter is then incorporated and all packaged ssRNA is converted to dsRNA, resulting in the generation of a rdsRN. At this point, the rdsRN is capable of generating recombinant segments-S and -M mRNA and segment-L mRNA; the latter expresses the proteins that constitute the procapsid, which uptake incorporate the recombinant segment and segment-L mRNA, then converted to dsRNA thereby generating additional rdsRNs (FIG. 6).

In vitro synthesized recombinant segment mRNA is introduced into packaging strains by electroporation. Preferably, the RNA is in vitro transcribed from linear DNA templates using fluorinated rNTP's (Durascribe, Epicentre, Madison, Wis.) to produce fluorinated RNA, which is nuclease-resistant RNA. Fluorinated dUTP and dCTP are incorporated into the reaction mixture at a final concentration of 5 mM each. While fNTP's are preferred, any modified rNTP, which imparts nuclease resistance, such as thiol or aminohexyl substituted rNTP's, is useful in the present invention. Thus, those skilled in the art will be able to substitute any modified NTP which imparts nuclease resistance in place of fluorinated NTP's.

The RNA or preferably the fluorinated RNA encodes at least a gene product that complements said at least one selectable phenotypic mutation and an RNA of interest operably linked to a eukaryotic translation initiation sequence. In a preferred embodiment, the fluorinated RNA encodes at least a gene product that complements said at least one selectable phenotypic mutation, gene-8 (SEQ ID 7) for stabilization of nucleocapsid production; and an RNA of interest operably linked to a eukaryotic translation initiation sequence.

To launch the rdsRN in said packaging strain, an electroporation medium is generated, composed of
  i) An electrocompetent bacterial strain, at a density of $10^8$-$10^{11}$ cfu/ml for packaging, launching and producing rdsRN, comprising
    a) genomic DNA comprising at least one non-reverting selectable phenotypic mutation;
    b) nucleic acid sequences encoding genes necessary for procapsid production; and
    c) one or more procapsids comprising proteins with RNA packaging and RNA polymerase activity.
  ii) 1 ng-1 mg, preferably 1 mcg-100 mcg, more preferably 5 mcg-40 mcg RNA encoding at least a gene product that complements said at least one selectable phenotypic mutation and an RNA of interest operably linked to a eukaryotic translation initiation sequence.

In a preferred embodiment, the rdsRN are launched in said packaging strain, using an electroporation medium composed of
  i) An electrocompetent bacterial strain, at a density of $10^8$-$10^{11}$ cfu/ml for packaging, launching and producing rdsRN, comprising
    a) genomic DNA comprising at least one non-reverting selectable phenotypic mutation;
    b) nucleic acid sequences encoding genes necessary for procapsid production; and
    c) one or more procapsids comprising proteins with RNA packaging and RNA polymerase activity.

ii) 1 ng-1 mg, preferably 1 mcg-100 mcg, more preferably 5 mcg-40 mcg RNA encoding at least a gene product that complements said at least one selectable phenotypic mutation, gene-8 (SEQ ID 7) for stabilization of nucleocapsid production; and an RNA of interest operably linked to a eukaryotic translation initiation sequence.

Alternatively, the rdsRN are launched in said packaging strain, using an electroporation medium composed of
i) An electrocompetent bacterial strain, at a density of $10^8$-$10^{11}$ cfu/ml for packaging, launching and producing rdsRN, comprising
   a) genomic DNA comprising at least one non-reverting selectable phenotypic mutation;
   1 ng-1 mg, preferably 1 mcg-100 mcg, more preferably 5 mcg-40 mcg RNA encoding at least a gene product that complements said at least one selectable phenotypic mutation, nucleic acid sequences encoding genes necessary for procapsid production, gene-8 (SEQ ID 7) for stabilization of nucleocapsid production; and an RNA of interest operably linked to a eukaryotic translation initiation sequence.

In a further preferred embodiment, the rdsRN are launched in said packaging strain, using an electroporation medium composed of
i) An electrocompetent bacterial strain, at a density of $10^8$-$10^{11}$ cfu/ml for packaging, launching and producing rdsRN, comprising
   a) genomic DNA comprising at least one non-reverting selectable phenotypic mutation;
   b) nucleic acid sequences encoding genes necessary for procapsid production; and
   c) one or more procapsids comprising proteins with RNA packaging and RNA polymerase activity.
ii) 1 ng-1 mg, preferably 1 mcg-100 mcg, more preferably 5 mcg-40 mcg fluorinated RNA encoding at least a gene product that complements said at least one selectable phenotypic mutation, gene-8 (SEQ ID 7) for stabilization of nucleocapsid production; and an RNA of interest operably linked to a eukaryotic translation initiation sequence.

In yet a further preferred embodiment, the rdsRN are launched in said packaging strain, using an electroporation medium composed of
i) An electrocompetent bacterial strain, at a density of $10^8$-$10^{11}$ cfu/ml for packaging, launching and producing rdsRN, comprising
   a) genomic DNA comprising at least one non-reverting selectable phenotypic mutation;
ii) 1 ng-1 mg, preferably 1 mcg-100 mcg, more preferably 5 mcg-40 mcg fluorinated RNA encoding at least a gene product that complements said at least one selectable phenotypic mutation, nucleic acid sequences encoding genes necessary for procapsid production, gene-8 (SEQ ID NO: 7) for stabilization of nucleocapsid production; and an RNA of interest operably linked to a eukaryotic translation initiation sequence.

The method used to electroporate said RNA or preferably, fluorinated RNA into said packaging strain is not important to the present invention and can be achieved using standard procedures well known to the art (Ausubel et al., supra, 1990; Sambrook, supra). Following electroporation the electroporation medium is admixed with recovery medium, as described (Ausubel et al., supra, 1990; Sambrook, supra) and incubated at 37° C. for 30 min-4 hr, preferably 2 hr.

Electrotransformants are isolated on solid media under conditions that only permit the growth of strains that harbor and express the positive selection allele in the recombinant segment (e.g. Trypticated Soy agar (herein referred to as TSA), Difco, Detroit, Mich.).

Bacterial isolates containing rdsRNs are cultured at temperatures that range from 25° C. to 44° C. for 16 to 96 hrs; however, it is preferable to culture the transformants at initially at 28° C. for 48 hr. Colonies that grow on the selective solid media are subsequently isolated and purified by standard methods (Ausubel et al., supra, 1990); (Sambrook, supra). To verify that the isolates selected are carrying the functional rdsRN of interest, individual isolates are screened by RT-PCR using primers designed to specifically amplify positive and negative (second) strand RNA sequences of, but not limited to, the strand-specific packaging sequences, the positive selection allele, the IRES, and the gene of interest. Methods of RNA preparation for analysis are well known to those skilled in the art, such as the following. Individual isolates may be cultured in liquid media (e.g. Trypticated Soy broth (herein referred to as "TSB"), Difco MO) and the resultant cultures harvested after reaching an optical density at 600 nm ($OD_{600}$) of 0.001 to 4.0, relative to the $OD_{600}$ of a sterile TSB control. The nucleocapsids are isolated from such cultures using methods reported elsewhere and well known to those skilled in the art (Gottlieb et al., J. Bacteriol 172:5774; 1990); (Sun et al., supra, 2003). The PCR primers for such an analysis are designed using Clone Manager® software version 4.1 (Scientific and Educational Software Inc., Durham, N.C.) or OLIGO 4.0 primer analysis software (copyright Wojciech Rychlik). This software enables the design of PCR primers that are compatible with the specific DNA fragments being manipulated. RT-PCRs are conducted in a Bio Rad iCycler, (Hercules, Calif.) and primer annealing, elongation and denaturation times in the RT-PCRs are set according to standard procedures (Ausubel et al., supra). The RT-PCR products are subsequently analyzed by agarose gel electrophoresis using standard procedures (Ausubel et al., supra, 1990); (Sambrook, supra). A positive clone is defined as one that displays the appropriate RT-PCR pattern that indicates that the rdsRNA segment has been stably maintained in the strain. The RT-PCR products can be further evaluated using standard DNA sequencing procedures, as described below.

Having identified the desired transformants, individual strains are stored in a storage media, which is TS containing 10-30% (v/v) glycerol. Bacterial isolates are harvested from solid media using a sterile cotton wool swab and suspended in storage media at a density of $10^8$-$10^9$ cfu/ml, and the suspensions are stored at −80° C.

Batches of purified rdsRNs are purified from said carrier strains using methods well known in the art and published extensively in detail elsewhere (Mindich, et al., J Virol 66, 2605-10; 1992); (Mindich, et al., Virology 212:213-217; 1995); (Mindich, et al, J Bacteriol 181:4505-4508; 1999); (Qiao, et al., Virology 275:218-224; 2000); (Qiao, et al., Virology 227:103-110; 1997); (Olkkonen, et al., Proc Natl Acad Sci USA 87:9173-9177; 1990); (Onodera, et al, J Virol 66, 190-196; 1992).

5. Use of rdsRNs to Induce to Cause a Biological Effect In Vivo

The specific method used to formulate the novel rdsRP expression systems described herein is not critical to the present invention and can be selected from a physiological buffer (Felgner et al., U.S. Pat. No. 5,589,466 (1996); aluminum phosphate or aluminum hydroxyphosphate (e.g. Ulmer et al., Vaccine, 18:18; 2000), monophosphoryl-lipid A (also referred to as MPL or MPLA; Schneerson et al., J. Immunol., 147: 2136-2140; 1991); (e.g. Sasaki et al., Inf. Immunol., 65: 3520-3528; 1997); (Lodmell et al., Vaccine, 18:1059-1066;

2000), QS-21 saponin (e.g. Sasaki, et al., J. Virol., 72:4931; 1998); dexamethasone (e.g. Malone, et al., J. Biol. Chem. 269:29903; 1994); CpG DNA sequences (Davis et al., J. Immunol., 15:870; 1998); or lipopolysaccharide (LPS) antagonist (Hone et al., supra 1997).

The rdsRN can be administered directly into eukaryotic cells, animal tissues, or human tissues by intravenous, intramuscular, intradermal, intraperitoneally, intranasal and oral inoculation routes. The specific method used to introduce the rdsRN constructs described herein into the target cell or tissue is not critical to the present invention and can be selected from previously described vaccination procedures (Wolff, et al., Biotechniques 11:474-85; 1991); (Johnston and Tang, Methods Cell Biol 43:353-365; 1994); (Yang and Sun, Nat Med 1:481-483; 1995); (Qiu, et al., Gene Ther. 3:262-8; 1996); (Larsen, et al., J. Virol. 72:1704-8; 1998); (Shata and Hone, J. Virol. 75:9665-9670; 2001); (Shata, et al., Vaccine 20:623-629; 2001); (Ogra, et al., J Virol 71:3031-3038; 1997); (Buge, et al., J. Virol. 71:8531-8541; 1997); (Belyakov, et al., Nat. Med. 7, 1320-1326; 2001); (Lambert, et al., Vaccine 19:3033-3042; 2001); (Kaneko, et al., Virology 267: 8-16; 2000); (Belyakov, et al., Proc Natl Acad Sci USA 96:4512-4517; 1999).

The specific biological effects covered by the invention described herein include, but are not limited to, protective or modulatory immune responses, therapeutic responses, and downregulation of expression (eg siRNA) or upregulation of expression (eg cytokine expression) of host proteins. Initially, the rdsRNs are administered at dose of $10^2$-$10^9$ nucleocapsid particles, and are administered by an appropriate route, such as orally, intranasally, subcutaneously, intramuscularly, or via invasive bacterial vectors (Sizemore et al, Science. 1995 Oct. 13; 270(5234):299-302). The number of doses varies depending on the potency of the individual rdsRNs and can be a single-, two- or three-dose regimen spaced by 2- to 4-week intervals. Each expression study includes a negative control rdsRN that does not contain the gene of interest, and a DNA vaccine vector that encodes the gene of interest can serve as a positive control.

Methods for measuring biological effects of rdsRN encoded gene expression in biological systems are well known to those skilled in the art. As an example, to measure serum IgG and IgA responses to gp120, sera are collected before and 10, 20, 30, 40, 50, 60, 70, and 80 days after vaccination. About 400-500 μl of blood is collected into individual tubes from the tail vein of each mouse and allowed to clot by incubating for 4 hr on ice. After centrifugation in a microfuge for 5 min, the sera are transferred to fresh tubes and stored at −80° C. Mucosal IgG and IgA responses to antigens expressed by the genes of interest are determined using fecal pellets and vaginal washes that will be harvested before and at regular intervals after vaccination (Srinivasan et al., Biol. Reprod. 53: 462; 1995); (Staats et al., J. Immunol. 157: 462; 1996). Standard ELISAs are used to quantitate the IgG and IgA responses to gp120 in the sera and mucosal samples (Abacioglu et al., AIDS Res. Hum. Retrovir. 10: 371; 1994); (Pincus et al., AIDS Res. Hum. Retrovir. 12: 1041; 1996). Ovalbumin can be included in each ELISA as a negative control antigen. In addition, each ELISA can include a positive control serum, fecal pellet or vaginal wash sample, as appropriate. The positive control samples are harvested from animals vaccinated intranasally with 10 μg of the antigen expressed by the gene of interest mixed with 10 μg cholera toxin, as described (Yamamoto et al., Proc. Natl. Acad. Sci. 94: 5267; 1997). The end-point titers are calculated by taking the inverse of the last serum dilution that produced an increase in the absorbance at 490 nm that is greater than the mean of the negative control row plus three standard error values.

To measure cellular immunity, cell suspensions of enriched $CD4^+$ and $CD8^+$ T cells from lymphoid tissues are used to measure antigen-specific T cell responses by cytokine-specific ELISPOT assay (Wu et al., AIDS Res. Hum. Retrovir. 13:1187; 1997). Such assays can assess the numbers of antigen-specific T cells that secrete IL-2, IL-4, IL-5, IL-6, IL-10 and IFN-γ. All ELISPOT assays are conducted using commercially-available capture and detection mAbs (R&D Systems and Pharmingen), as described (Wu et al., Infect. Immun. 63:4933; 1995) and used previously (Xu-Amano et al., J. Exp. Med. 178:1309; 1993); (Okahashi et al., Infect. Immun. 64: 1516; 1996). Each assay includes mitogen (Con A) and ovalbumin controls.

6. Use of Bacterial Vectors Carrying rdsRNs to Induce an Immune Response or to Cause a Biological Effect in Target Cells or Tissues.

Delivery of the rdsRN to and expression of the encoded sequences in a targeted eukaryotic cell, tissue, or organism may be accomplished by inoculation with rdsRNs carried in a non-pathogenic or attenuated bacterial vaccine vector. Biological responses of interest include, but are not limited to, protective or modulatory immune responses, therapeutic responses, and downregulation of expression (eg siRNA) or upregulation of expression (eg cytokine expression) of host proteins.

The bacterial species from which the bacterial vaccine vector is derived in the present invention is not critical thereto and include, but are not limited to: *Campylobacter* spp, *Neisseria* spp., *Haemophilus* spp, *Aeromonas* spp, *Francisella* spp, *Yersinia* spp, *Klebsiella* spp, *Bordetella* spp, *Legionella* spp, *Corynebacterium* spp, *Citrobacter* spp, *Chlamydia* spp, *Brucella* spp, *Pseudomonas* spp, *Helicobacter* spp, or *Vibrio* spp.

The particular *Campylobacter* strain employed is not critical to the present invention. Examples of *Campylobacter* strains that can be employed in the present invention include but are not limited to: *C. jejuni* (ATCC Nos. 43436, 43437, 43438), *C. hyointestinalis* (ATCC No. 35217), *C. fetus* (ATCC No. 19438) *C. fecalis* (ATCC No. 33709) *C. doylei* (ATCC No. 49349) and *C. coli* (ATCC Nos. 33559, 43133).

The particular *Yersinia* strain employed is not critical to the present invention. Examples of *Yersinia* strains which can be employed in the present invention include *Y. enterocolitica* (ATCC No. 9610) or *Y. pestis* (ATCC No. 19428), *Y. enterocolitica* Ye03-R2 (al-Hendy et al., Infect. Immun., 60:870; 1992) or *Y. enterocolitica* aroA (O'Gaora et al., Micro. Path., 9:105; 1990).

The particular *Klebsiella* strain employed is not critical to the present invention. Examples of *Klebsiella* strains that can be employed in the present invention include *K. pneumoniae* (ATCC No. 13884).

The particular *Bordetella* strain employed is not critical to the present invention. Examples of *Bordetella* strains that can be employed in the present invention include *B. pertussis* and *B. bronchiseptica* (ATCC No. 19395).

The particular *Neisseria* strain employed is not critical to the present invention. Examples of *Neisseria* strains that can be employed in the present invention include *N. meningitidis* (ATCC No. 13077) and *N. gonorrhoeae* (ATCC No. 19424), *N. gonorrhoeae* MS11 aro mutant (Chamberlain et al., Micro. Path., 15:51-63; 1993).

The particular *Aeromonas* strain employed is not critical to the present invention. Examples of *Aeromonas* strains that can be employed in the present invention include *A. salmi-* nocida (ATCC No. 33658), *A. schuberii* (ATCC No. 43700), *A. hydrophila, A. eucrenophila* (ATCC No. 23309).

The particular *Francisella* strain employed is not critical to the present invention. Examples of *Francisella* strains that can be employed in the present invention include *F. tularensis* (ATCC No. 15482).

The particular *Corynebacterium* strain employed is not critical to the present invention. Examples of *Corynebacterium* strains that can be employed in the present invention include *C. pseudotuberculosis* (ATCC No. 19410).

The particular *Citrobacter* strain employed is not critical to the present invention. Examples of *Citrobacter* strains that can be employed in the present invention include *C. freundii* (ATCC No. 8090).

The particular *Chlamydia* strain employed is not critical to the present invention. Examples of *Chlamydia* strains that can be employed in the present invention include *C. pneumoniae* (ATCC No. VR1310).

The particular *Haemophilus* strain employed is not critical to the present invention. Examples of *Haemophilus* strains that can be employed in the present invention include *H. influenzae* (Lee et al., supra), *H. somnus* (ATCC No. 43625).

The particular *Brucella* strain employed is not critical to the present invention. Examples of *Brucella* strains that can be employed in the present invention include *B. abortus* (ATCC No. 23448).

The particular *Legionella* strain employed is not critical to the present invention. Examples of *Legionella* strains that can be employed in the present invention include *L. pneumophila* (ATCC No. 33156), or a *L. pneumophila* mip mutant (Ott, FEMS Micro. Rev., 14:161; 1994).

The particular *Pseudomonas* strain employed is not critical to the present invention. Examples of *Pseudomonas* strains that can be employed in the present invention include *P. aeruginosa* (ATCC No. 23267).

The particular *Helicobacter* strain employed is not critical to the present invention. Examples of *Helicobacter* strains that can be employed in the present invention include pylori (ATCC No. 43504), *H. mustelae* (ATCC No. 43772).

The particular *Vibrio* strain employed is not critical to the present invention. Examples of *Vibrio* strains that can be employed in the present invention include *Vibrio cholerae* (ATCC No. 14035), *Vibrio cincinnatiensis* (ATCC No. 35912), *V. cholerae* RSI virulence mutant (Taylor et al., J. Infect. Dis., 170:1518-1523; 1994) and *V. cholerae* ctxA, ace, zot, cep mutant (Waldor et al., J. Infect. Dis., 170:278-283; 1994).

In a preferred embodiment, the bacterial species from which the bacterial vaccine vector is derived in the present invention includes attenuated derivatives of bacteria previously shown to possess the potential to serve as vaccine vectors, such as the Enterobacteriaceae, including but not limited to *Escherichia* spp, *Shigella* spp, and *Salmonella* spp. Gram-positive and acid-fast packaging and vector strains could similarly be constructed from *Listeria monocytogenes* or *Mycobacterium* spp.

The particular *Escherichia* strain employed is not critical to the present invention. Examples of *Escherichia* strains which can be employed in the present invention include *Escherichia coli* strains DH5α, HB 101, HS-4, 4608-58, 1184-68, 53638-C-17, 13-80, and 6-81 (Sambrook et al., supra, 2001); (Sansonetti et al., Ann. Microbiol. (Inst. Pasteur), 132A:351; 1982), enterotoxigenic *E. coli* (Evans et al., Infect. Immun., 12:656; 1975), enteropathogenic *E. coli* (Donnenberg et al., J. Infect. Dis., 169:831; 1994) and enterohemorrhagic *E. coli* (McKee and O'Brien, Infect. Immun., 63:2070; 1995).

The particular *Salmonella* strain employed is not critical to the present invention. Examples of *Salmonella* strains that can be employed in the present invention include *S. typhi* (ATCC No. 7251), *S. typhimurium* (ATCC No. 13311), *Salmonella galinarum* (ATCC No. 9184), *Salmonella enteriditis* (ATCC No. 4931) and *Salmonella typhimurium* (ATCC No. 6994). *S. typhi* aroC, aroD double mutant (Hone et al., Vacc., 9:810-816; 1991), *S. typhimurium* aroA mutant (Mastroeni et al., Micro. Pathol., 13:477-491; 1992).

The particular *Shigella* strain employed is not critical to the present invention. Examples of *Shigella* strains that can be employed in the present invention include *Shigella flexneri* (ATCC No. 29903), *Shigella flexneri* CVD1203 (Noriega et al., Infect Immun. 62:5168; 1994), *Shigella flexneri* 15D (Vecino et al., Immunol Lett 82:197; 2002), *Shigella sonnei* (ATCC No. 29930), and *Shigella dysenteriae* (ATCC No. 13313).

The particular *Mycobacterium* strain employed is not critical to the present invention. Examples of *Mycobacterium* strains that can be employed in the present invention include *M. tuberculosis* CDC1551 strain (Griffith et al., Am. J. Respir. Crit. Care Med. August; 152(2):808; 1995), *M. tuberculosis* Beijing strain (Soolingen et al., 1995) H37Rv strain (ATCC#: 25618), *M. tuberculosis* pantothenate auxotroph strain (Sambandamurthy, Nat. Med. 2002 8(10):1171; 2002), *M. tuberculosis* rpoV mutant strain (Collins et al., Proc Natl Acad Sci USA. 92(17):8036; 1995), *M. tuberculosis* leucine auxotroph strain (Hondalus et al., Infect. Immun. 68(5):2888; 2000), BCG Danish strain (ATCC # 35733), BCG Japanese strain (ATCC # 35737), BCG, Chicago strain (ATCC # 27289), BCG Copenhagen strain (ATCC #: 27290), BCG Pasteur strain (ATCC #: 35734), BCG Glaxo strain (ATCC #: 35741), BCG Connaught strain (ATCC # 35745), BCG Montreal (ATCC # 35746).

The particular *Listeria monocytogenes* strain employed is not critical to the present invention. Examples of *Listeria monocytogenes* strains which can be employed in the present invention include *L. monocytogenes* strain 10403S (e.g. Stevens et al., J Virol 78: 8210-8218; 2004) or mutant *L. monocytogenes* strains such as (i) actA plcB double mutant (Peters et al., FEMS Immunology and Medical Microbiology 35: 243-253; 2003); (Angelakopoulous et al., Infect and Immunity 70: 3592-3601; 2002); (ii) dal dat double mutant for alanine racemase gene and D-amino acid aminotransferase gene (Thompson et al., Infect and Immunity 66: 3552-3561; 1998).

Methods to attenuate *E. coli, Salmonella, Mycobacteria, Shigella*, and *Listeria* are not important to the present invention and are well known to those skilled in the art (Evans et al., supra, 1975); (Noriega et al., supra, 1994); (Hone et al., supra, 1991).

Once a non-pathogenic or attenuated bacterial vaccine vector strain has been selected, said strain is modified to serve as an rdsRN packaging strain. This is accomplished using the strategies described in detail above that entail introducing segment-L sequences that expresses dsRP procapsids in said strain and a mutation to enable selection and maintenance of the rdsRNs that express a functional gene that complements the deficiency created by the mutation in said strain.

To generate strains that package and stably maintain the desired rdsRN, in vitro synthesized recombinant segment RNA(s) are introduced into packaging strains by electroporation and transformants are isolated in solid media under conditions that only permit the growth of strains that harbor and express the positive selection allele in the recombinant segment (e.g. Trypticated Soy agar will only permit the growth of asd and murI mutants when the wild-type gene complements that genomic defect, Difco, Detroit, Mich., Cat. No. 244520). The methods for generating rdsRNA segments, in vitro mRNA synthesis and electroporation are all provided above. To verify that the isolates are carrying the rdsRN of interest, individual isolates are cultured in liquid media (e.g. TS, Difco, Detroit, Mich., Cat. No. 244620) and nucleocapsids are isolated from said cultures using methods reported elsewhere and well known to those skilled in the art (Gottlieb et al., supra, 1990); (Sun et al., supra, 2003). DsRNA is isolated from the nucleocapsids using commercially available RNA extraction kits and screened by RT-PCR using primers that amplify defined fragments within the recombinant segments, including but not limited to PCR primers that amplify the positive selection allele, the IRES and the gene of interest, as discussed in detail above. A positive clone is defined as one that displays the appropriate RT-PCR pattern that indicates that the rdsRNA segment has been stably maintained in the strain. The RT-PCR products can be further evaluated using standard DNA sequencing procedures, as described below.

The specific culture conditions for the growth of said bacterial vaccine vector strains that stably harbor rdsRNs are not critical to the present invention. For illustrative purposes, the said mutants can be grown in a liquid medium such a LB medium (Difco, Detroit, Mich., Cat. No. 244620), Nutrient broth (Difco, Detroit, Mich., Cat. No. 233000), or Tryptic Soy broth (Difco, Detroit, Mich., Cat. No. 211822), using conventional culture techniques that are appropriate for the bacterial strain being grown (Miller, supra, 1991). As an alternative the bacteria can be cultured on solid media such as Nutrient agar (Difco, Detroit, Mich., Cat. No. 212000), Tryptic Soy agar (Difco, Detroit, Mich., Cat. No. 236920), or M9 minimal agar (Difco, Detroit, Mich., Cat. No. 248510).

*Mycobacterium* vaccine vector strains are cultured in liquid media, such as Middlebrook 7H9 (Difco, Detroit, Mich., Cat. No. 271310) or Saulton Synthetic Medium, preferably at 37° C. The strains can be maintained as static or agitated cultures. In addition, the growth rate of *Mycobacterium* can be enhanced by the addition of oleic acid (0.06% v/v; Research Diagnostics Cat. No. 01257) and detergents such as Tyloxapol (0.05% v/v; Research Diagnostics Cat. No. 70400). The purity of *Mycobacterium* cultures can be evaluated by evenly spreading 100 µl aliquots of the *Mycobacterium* culture serially diluted (e.g. 10-fold steps from Neat—$10^{-8}$) in phosphate buffered saline (herein referred to PBS) onto 3.5 inch plates containing 25-30 ml of solid media, such as Middlebrook 7H10 (BD Microbiology, Cockeyesville, Md., Cat. No. 221174).

The amount of the bacterial vaccine vector to be administered with the rdsRN of the present invention will vary depending on the species of the subject, as well as the disease or condition that is being treated. Generally, the dosage employed will be about $10^3$ to $10^{11}$ viable organisms, preferably about $10^3$ to $10^9$ viable organisms.

The bacterial vector harboring the rdsRNs is generally administered along with a pharmaceutically acceptable carrier or diluent. The particular pharmaceutically acceptable carrier or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al., J. Clin. Invest., 79:888-902; 1987); (Black et al., J. Infect. Dis., 155:1260-1265; 1987), or bicarbonate buffer (pH 7.0) containing ascorbic acid, lactose, and optionally aspartame (Levine et al., Lancet, II: 467-470; 1988). Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10% (w/v).

The biological activity of vector strains is assessed in an appropriate animal model (e.g. BATS/cJ mice, rabbits, guinea pigs or *Rhesus macaques*). Initially, the rdsRN vector strains are administered at doses of $10^2$-$10^9$ cfu, and are administered by an appropriate route (e.g. *E. coli, Salmonella* and *Shigella* can be given intragastrically or intranasally, whereas rBCG vectors are injected subcutaneously). The number of doses will vary, depending on the potency of the individual vector strain, and the valency of the encoded recombinant product of interest.

Methods of measurement of immune and other biological responses to rdsRN encoded products are well known to those skilled in the art. To measure serum IgG and IgA responses to gp120, sera are collected before and 10, 20, 30, 40, 50, 60, 70, and 80 days after vaccination. About 400-500 µl of blood is collected into individual tubes from the tail vein of each mouse and allowed to clot by incubating for 4 hr on ice. After centrifugation in a microfuge for five minutes, the sera are transferred to fresh tubes and stored at −80° C. Mucosal IgG and IgA responses to antigens expressed by the genes of interest are determined using fecal pellets and vaginal washes that will be harvested before and at regular intervals after vaccination (Srinivasan et al., Biol. Reprod. 53: 462; 1995); (Staats et al., J. Immunol. 157: 462; 1996). Standard ELISAs are used to quantitate the IgG and IgA responses to gp120 in the sera and mucosal samples (Abacioglu et al., AIDS Res. Hum. Retrovir. 10: 371; 1994); (Pincus et al., AIDS Res. Hum. Retrovir. 12: 1041; 1996). Ovalbumin can be included in each ELISA as a negative control antigen. In addition, each ELISA can include a positive control serum, fecal pellet or vaginal wash sample, as appropriate. The positive control samples are harvested from animals vaccinated intranasally with 10 µg of the antigen expressed by the gene of interest mixed with 10 µg cholera toxin, as described (Yamamoto et al., Proc. Natl. Acad. Sci. 94: 5267; 1997). The end-point titers are calculated by taking the inverse of the last serum dilution that produced an increase in the absorbance at 490 nm that is greater than the mean of the negative control row plus three standard error values.

Cellular immunity may be measured by intracellular cytokine staining (also referred to as intracellular cytokine cytometry) or by ELISPOT (Letsch A. et al., Methods 31:143-49; 2003). Both methods allow the quantitation of antigen-specific immune responses, although ICS also adds the simultaneous capacity to phenotypically characterize antigen-specific CD4+ and CD8+ T-cells. Such assays can assess the numbers of antigen-specific T cells that secrete IL-2, IL-4, IL-5, IL-6, IL-10 and IFN- (Wu et al., AIDS Res. Hum. Retrovir. 13: 1187; 1997). ELISPOT assays are conducted using commercially-available capture and detection mAbs (R&D Systems and Pharmingen), as described (Wu et al., Infect. Immun. 63:4933; 1995) and used previously (Xu-Amano et al., J. Exp. Med. 178:1309; 1993); (Okahashi et al., Infect. Immun. 64: 1516; 1996). Each assay includes mitogen (Con A) and ovalbumin controls.

7. Recombinant DNA Techniques

The recombinant DNA procedures used in the construction of the packaging strains, bacterial vectors and rdsRNs, including, but not limited to, PCR, restriction endonuclease (herein referred to as "RE") digestions, DNA ligation, agarose gel electrophoresis, DNA purification, and dideoxynucleotide sequencing, are described elsewhere (Miller, *A Short Course in Bacterial Genetics*, Cold Spring Harbor Laboratory Press, Cold Spring Harbor, N.Y.; 1992); (Bothwell et al., supra); and (Ausubel et al., supra), bacteriophage-mediated transduction (de Boer, supra); (Miller, supra, 1992) and (Ausubel et al., supra), or chemical (Bothwell et al., supra); (Ausubel et al., supra); (Felgner et al., supra); and Farhood, supra), electroporation (Bothwell et al., supra); (Ausubel et al., supra); (Sambrook, *Molecular Cloning: A Laboratory Manual*, Cold Spring Harbor Laboratory Press, Cold Spring Harbor, N.Y.; 1992) and physical transformation techniques (Johnston et al., supra); (Bothwell et al., supra). The genes can be incorporated on phage (de Boer et al., *Cell,* 56:641-649; 1989), plasmids vectors (Curtiss et al., supra) or spliced into the chromosome (Hone et al., supra) of the target strain.

Gene sequences can be made synthetically using an Applied Biosystems ABI™ 3900 High-Throughput DNA Synthesizer (Foster City, Calif. 94404 U.S.A.) and procedures provided by the manufacturer. To synthesize large sequences i.e greater than 200 bp, a series of segments of the full-length sequence are generated by PCR and ligated together to form the full-length sequence using procedures well know in the art. However, smaller sequences, i.e. those smaller than 200 bp, can be made synthetically in a single round using an Applied Biosystems ABI™ 3900 High-Throughput DNA Synthesizer (Foster City, Calif.) and procedures provided by the manufacturer.

Recombinant plasmids are introduced into bacterial strains by electroporation using a BioRad Gene-Pulser® set at 200 Ω, 25 µF and 2.5 kV (BioRad Laboratories, Hercules, Calif.) [38]. Nucleotide sequencing to verify cDNA sequences is accomplished by standard automated sequencing techniques (Applied Biosystems automated sequencer, model 373A). DNA primers for DNA sequencing and polymerase chain reaction (herein referred to as "PCR") are synthesized using an Applied Biosystems ABI™ 3900 High-Throughput DNA Synthesizer (Foster City, Calif. 94404).

The following examples are provided for illustrative purposes only, and are in no way intended to limit the scope of the present invention.

EXAMPLES

Example 1

Recombinant DNA Procedures

Restriction endonucleases (herein "RE"); New England Biolabs, Beverly, Mass.), T4 DNA ligase (New England Biolabs, Beverly, Mass.) and Taq polymerase (Life Technologies, Gaithersburg, Md.) were used according to the manufacturers' protocols; Plasmid DNA was prepared using small-scale (Qiagen Miniprep® kit, Santa Clarita, Calif.) or large-scale (Qiagen Midiprep® kit, Santa Clarita, Calif.) plasmid DNA purification kits according to the manufacturer's protocols (Qiagen, Santa Clarita, Calif.); Nuclease-free, molecular biology grade deionized water, Tris-HCl (pH 7.5), EDTA pH 8.01M $MgCl_2$, 100% (v/v) ethanol, ultra-pure agarose, and agarose gel electrophoresis buffer were purchased from Life Technologies, Gaithersburg, Md. RE digestions, PCRs, DNA ligation reactions and agarose gel electrophoresis were conducted according to well-known procedures (Sambrook, et al., supra, 1989); (Ausubel, et al., supra, 1990). Nucleotide sequencing to verify the DNA sequence of each recombinant plasmid described in the following examples was accomplished by conventional automated DNA sequencing techniques using an Applied Biosystems automated sequencer, model 373A.

PCR primers were purchased from the Integrated DNA Technologies (Coralville, Iowa) or the University of Maryland Biopolymer Facility (Baltimore, Md.) and were synthesized using an Applied Biosystems DNA synthesizer (model 373A). PCR primers were used at a concentration of 200 µM and annealing temperatures for the PCR reactions were determined using Clone manager software version 4.1 (Scientific and Educational Software Inc., Durham, N.C.) or OLIGO primer analysis software version 4.0. PCRs were conducted in a Bio Rad iCycler, (Hercules, Calif.). The PCR primers for the amplifications are designed using Clone Manager® software version 4.1 (Scientific and Educational Software Inc., Durham, N.C.) OLIGO primer analysis software version 4.0. This software enables the design of PCR primers and identifies RE sites that are compatible with the specific DNA fragments being manipulated. PCRs were conducted in a Bio Rad iCycler, (Hercules, Calif.) and primer annealing, elongation and denaturation times in the PCRs were set according to standard procedures (Ausubel et al., supra). The RE digestions and the PCRs were subsequently analyzed by agarose gel electrophoresis using standard procedures (Ausubel et al., supra); (Sambrook, supra). A positive clone was defined as one that displays the appropriate RE pattern and/or PCR pattern. Plasmids identified through this procedure can be further evaluated using standard DNA sequencing procedures, as described above.

*Escherichia coli* strains Top10 and DH5α were purchased from Invitrogen (Carlsbad, Calif.) and strain SCS110 was purchased from Stratagene (La Jolla, Calif.) These served as hosts of the recombinant plasmids described in the examples below. Recombinant plasmids were introduced into *E. coli* by electroporation using a Gene Pulser (BioRad Laboratories, Hercules, Calif.) set at 200 Ω, 25 µF and 1.8 kV or chemical transformation, as described (Ausubel et al., supra).

Bacterial strains were grown on tryptic soy agar (Difco, Detroit, Mich.) or in tryptic soy broth (Difco, Detroit, Mich.), unless otherwise stated, at an appropriate temperature. Media were supplemented with 100 µg/ml ampicillin, 50 µg/ml kanamycin, and/or chloramphenicol 20 µg/ml (Sigma, St. Louis, Mo.) as needed. Bacterial strains were stored at −80° C. suspended in tryptic soy broth (Difco) containing 30% (v/v) glycerol (Sigma, St Louis, Mo.) at ca. $10^9$ colony-forming units (herein referred to as "cfu") per ml.

Reagent List

KpnI (New England Biolabs, Beverly, Mass., Cat. Nos. R0142S), PstI (New England Biolabs, Beverly, Mass., Cat. No. R0140S), Tryptic Soy broth (Difco, Detroit, Mich., Cat. No. 211822), Tryptic Soy agar (Difco, Detroit, Mich., Cat. No. 236920), Miniprep® plasmid DNA purification kit (Qiagen, Valencia, Calif., Cat. No. 27106), glycerol (Sigma, St. Louis, Mo., Cat. No. G5516), HpaI (New England Biolabs, Beverly, Mass., Cat. No. R0105S), Calf intestinal alkaline phosphatase (New England Biolabs, Beverly, Mass., Cat. No. M0290S), Vent$_R$® DNA polymerase (New England Biolabs, Cat. No. M0254S), QIAquick PCR purification kit (Qiagen, Cat. No. 28106, Valencia, Calif.), diaminopimelic acid (Sigma-Aldrich, St. Louis, Mo., Cat. No. D1377), BglII (New England Biolabs, Beverly, Mass., Cat No. R0144S), IPTG (Invitrogen, Carlsbad, Calif., Cat. No. 15529-019), Cell culture lysis reagent (Promega, Madison, Wis., Cat. No. E1531), lysozyme (Sigma, St. Louis, Mo., Cat. No. L6876), potassium phosphate (Sigma, St. Louis, Mo., Cat. No. P5379), magnesium chloride (Sigma, St. Louis, Mo., Cat. No. M1028) DraIII (New England Biolabs, Beverly, Mass., Cat. No. R0510S), PsiI (New England Biolabs, Beverly, Mass., Cat. No. V0279S), Proteinase K (Ambion, Austin, Tex., Cat. No. 2542-2548), Durascribe T7 transcription kit (Epicentre, Madison, Wis.), Durascribe SP6 transcription kit (Epicentre, Madison, Wis.), MEGAscript® T7 transcription kit (Ambion, Austin, Tex., Cat. No. 1334), MEGAscript® SP6 transcription kit (Ambion, Austin, Tex., Cat No. 1330), MEGAclear columns (Ambion, Austin, Tex., Cat No. 1908), BrightStar biotinylated RNA millennium marker (Ambion, Austin, Tex., Cat. No. 7170), BrightStar nylon membrane (Ambion, Austin, Tex., Cat. No. 10102), BrightStar Biodetect kit (Ambion, Austin, Tex., Cat. No. 1930), Tris-HCl buffer (Quality Biological, Gaithersburg, Md., Cat. No. 351-007-100), magnesium chloride (Sigma-Aldrich, St. Louis, Mo., Cat. No. M1787), ammonium acetate (Sigma-Aldrich, St. Louis, Mo., Cat. No. A2706), sodium chloride (Sigma-Aldrich, St. Louis, Mo., Cat. No. S7653), potassium chloride (Sigma-Aldrich, St. Louis, Mo., Cat. No. P3911), dithiothreitol (Sigma-Aldrich, St. Louis, Mo., Cat. No. D9779), EDTA (Sigma-Aldrich, St. Louis, Mo., Cat. No. E8008), polyethylene glycol 4000 (Fluka, Buchs, Switzerland, Cat. No. 95904), SUPERase RNase inhibitor (Ambion, Austin, Tex., cat. No 2694,), biotin-14-CTP (Invitrogen, Carlsbad, Calif., Cat. No. 19519-016), RNase ONE ribonuclease (Promega, Madison, Wis., Cat. No. M4261).

Example 2

Construction of rdsRNA Segments that Complement an Asd Mutation and Express Fluorescent Reporters and *Mycobacterium tuberculosis* Antigens and LCMV Antigens The goal of the study was to develop recombinant segments that can be incorporated into a prototype rdsRN based on the dsRNA genome of phi-8 (Mindich et al., J. Bacteriol, 181: 4505; 1999); (Mindich, Microbiol. Mol. Biol. Rev, 63: 149; 1999); (Hoogstraten et al., Virology, 272: 218; 2000); (Sun et al., Virology, 308: 354; 2003). As discussed above, the phi-8 genome consists of three segments: S, M, and L. A prototype rdsRN was constructed such that the RNA-dependent RNA polymerase encoded by wild-type segment-L (herein referred to as "wtL") expresses passenger genes cloned into recombinant segments-M and -S (herein referred to as "rM" and "rS", respectively). Both rM and rS encode a wild-type aspartic semialdehyde dehydrogenase gene (herein referred to as "asd," GenBank # V00262) linked to the bacterial ribosomal binding site of gene 10 and gene 8, respectively (see FIG. 4) and a gene of interest (i.e. the fluorescent protein HcRed and the mycobacterial antigen TBS) functionally linked to the IRES of hepatitis C virus. Notice that no phage structural genes on segments-M and -S were initially incorporated into rM or rS although the asd allele of rS was replaced with gene 8 of the wild type segment-S in a later incarnation of the invention to stabilize the rdsRN's. The asd allele and the IRES::HcRed and Mtb antigen encoding sequences are flanked by the 5-prime and 3-prime untranslated sequences that encode the pac and the negative-strand RNA synthesis initiation sequences, respectively. In other words, the reported genes on rM are flanked by the 5-prime pac sequence of segment-M and the 3-prime terminal sequence of segment-M. Similarly, rS consists of the reported genes flanked by the 5-prime pac sequence of segment-S and the 3-prime terminal sequence of segment-S genes (FIG. 5). Note that this configuration only permits the production of rdsRNs and that neither phage nor rdsRP particles are formed.

Construction of recombinant segments was accomplished using synthetic DNA and standard recombinant DNA techniques, such as PCR, RT-PCR, site-directed mutagenesis, restriction enzyme digests, gel electrophoresis, ligation, dideoxynucleotide sequencing, and bacterial transformation, as described in Example 1.

Recombinant segment-S (rS) was synthesized by Midland Certified Reagent Co., (Midland, Tex.). The 5- and 3-prime sequences were derived from a cDNA copy of phi-8 segment-S (kindly provided by Dr. Leonard Mindich, GenBank accession no. AF226853) with the modifications described below. In 5-prime to 3-prime orientation, rS (SEQ ID NO: 1) consists of the following fused components (FIG. 4):

(i) S pac sequence and ribosomal binding site (herein referred to as "RBS") of gene 8 is the first 187 nucleotides of segment-S (GenBank accession no. AF226853) and is required for uptake by procapsid (Hoogstraten et al., supra,; 2000). The RBS is required for initiation of translation in prokaryotic cells.

(ii) asd gene functionally linked to the RBS above for positive selection in Δasd *E. coli* strain X6212. The asd sequence was obtained from bases 240-1343 of GenBank accession no. V00262.

(iii) The hepatitis C virus internal ribosomal entry site for initiation of translation in eukaryotic cells. The sequence spans bases 36-341 of GenBank accession no. AJ242651.

(iv) Multiple cloning site (MCS) for insertion of passenger gene.

(v) Semliki Forest Virus 3' untranslated region for polyadenylation of rS mRNA; nucleotides 1-261 of GenBank accession no. V01398.

(vi) The phi-8 segment-S 3-prime terminal sequence, i.e. bases 3081-3192 of segment-S (GenBank accession no. AF226853), which is required for RNA stability and for phi-8 polymerase binding prior to initiation of negative strand RNA synthesis.

A synthetic DNA fragment comprised of the above components (SEQ ID NO:1) was joined to PstI-digested pT7/T3-18 DNA (Cat. No. 7201, Ambion, Austin, Tex.) using the T4 DNA ligase as described in Example 1. Following ligation, the DNA was introduced into *E. coli* strain DH5α-E (Invitrogen, Carlsbad, Calif., Cat. No. 11319-019) using electroporation (Example 1), and transformants were isolated by culturing on TSA supplemented with ampicillin (100 μg/ml) at 37° C. for 16-24 hr. Successful ligation products were identified by isolating super-coiled DNA from 2 ml cultures that were inoculated by stabbing the resulting single colonies with a sterile toothpick and placing the toothpick into sterile TSB supplemented with ampicillin (100 μg/ml); the cultures were incubated with agitation (200 opm) at 37° C. for 16-24 hr. After centrifugation the liquid supernatant was discarded and the bacterial pellets were resuspended in 100 μl of solution P1 of the Miniprep® plasmid DNA purification kit (Qiagen, Valencia, Calif., Cat. No. 27106). Plasmid DNA was then extracted and purified by following the instructions of the manufacturer (See Qiagen, Valencia, Calif., Cat. no. 27106 instruction manual). The purified plasmid DNA was digested with the restriction endonuclease PstI (New England Biolabs, Beverly, Mass., Cat no. R0140S) according to the manufacturer's instructions and using buffers provided by the manufacturer and incubated at 37° C. for 1 hr. The resulting DNA fragments were fractionated by agarose gel electrophoresis as described (See Example 1) and plasmids displaying the appropriate pattern were further characterized by dideoxynucleotide sequencing (Example 1). This procedure identified four independent isolates that carried plasmid pT7/T3-18 carrying DNA encoding rS. The plasmids in these isolates was designated AF1 and the four isolates harboring this plasmid were streaked onto TSA supplemented with ampicillin (100 μg/ml) and incubated at 37° C. for 16-24 hr. The bacteria were subsequently harvested using a sterile cotton wool swab (Puritan, Guilford, Me., Cat. No. 25-8061WC) and suspended in TSB containing 30% (v/v) glycerol (Sigma, St. Louis, Mo., Cat. No. G5516) at a density of about $10^9$ cfu/ml and stored in 1 ml aliquots at −80° C.

A second rS (rS2) was constructed by PCR amplification of bp 1-1294 of the phi-8 wt segment-S sequence (GenBank accession no. AF226853) linked by a BglII site by to the Hepatitis C IRES and downstream sequence of rS (bp1301-2020) as described above (rS2, SEQ ID NO:3). This construct was ligated into the PstI site of pT7T3-18 and transformed into E. coli Top10. Transformants were analyzed as described above and six correct isolates were designated pAF1S2.

Recombinant segment-M (rM, SEQ ID NO:2) is similar to rS, except that the 5-prime pac and 3-prime terminal sequences were derived from wt segment-M, nucleotides 1-262 and 4677-4741, respectively, of GenBank accession no. AF226852. Thus, like rS, rM consists of exogenous sequences flanked by phi-8 5-prime pac and 3-prime terminal sequence (see FIG. 4). The 2060 bp rM (SEQ ID NO: 2) was cloned into the KpnI and PstI sites (New England Biolabs, Beverly, Mass., Cat. Nos. R0142S and R0140S, respectively) of the plasmid pcDNA3.1$_{zeo}$(+) (Invitrogen, Cat. No. V860-20, Carlsbad, Calif.). Recombinant plasmids harboring the appropriate inserts were identified using the procedure employed for rS and the novel plasmid was designated pAF19.

To construct a eukaryotic expression cassette, pAF1 was digested with HpaI and NotI (New England Biolabs, Beverly, Mass., Cat. No. R0105S). This RE digest resulted in a directional cloning site within the MCS such that, once ligated, the Hc-Red gene and mycobacterial antigen package are immediately downstream of, and functionally linked to, the HCV IRES. Following digestion, the ends of the linearized plasmid were dephosphorylated with Calf intestinal alkaline phosphatase (New England Biolabs, Beverly, Mass., Cat. No. M0290S) to prevent recircularization. The dephosphorylated plasmid was then purified by electrophoresis in a 0.8% agarose gel followed by gel extraction.

The 2.0 kb mycobacterial antigen fusion sequence (TBS) was PCR amplified from the plasmid pAdApt35.Bsu.TB.S (Crucell) using Accuprime DNA polymerase (Invitrogen, Carlsbad, Calif.) and primers including HpaI and NotI RE sites. The size of the amplified sequence was verified by agarose gel electroporesis, and was purified using a QIAquick PCR purification kit by following manufacturer's instructions (Qiagen, Cat. No. 28106, Valencia, Calif.).

The fragment encoding TB.S was ligated into dephosphorylated pAF1 using T4 DNA ligase (New England Biolabs, Cat. No. M0202S) and the resulting plasmid was designated pSTB2.

The TBS antigen fusion sequence and HC-Red coding sequence were similarly inserted into the HpaI site in rM carried on pAF19 (FIG. 4) using recombinant DNA procedures as above. The resulting plasmids were designated pMTB7 and pMHc-Red.

Plasmids pSTB2 and pLM2775 (encoding the wild-type segment-S) were linearized with RE's SphI and PsiI and the resultant linearized fragments were purified by agarose gel electrophoresis and extraction. Plasmids pMTB7 and pMHc-Red were linearized similarly with SphI and PsiI. The linearized DNA sequences from each of the four RE digests were used as templates in Durascribe T7 (Epicentre, Madison, Wis.) in vitro transcription reactions according to the manufacturer's instructions to produce fluorinated RNA transcripts of wtS, rS encoding antigens TBS, rM encoding encoding antigens TBS, and rM encoding Hc-Red.

A third set of rdsRNA segments were similarly constructed to express the glycoprotein antigens GP-1 and GP-2 of lymphocytic choriomenengitis virus (herein "LCMV"). A 1511 bp fragment was PCR-amplified from plasmid pCMV-GP encoding the GP polyprotein precursor located on the large chromosome of the LCMV genome. The sequence was amplified using Accuprime DNA polymerase (Invitrogen, Carlsbad, Calif.) and primers including HpaI and NotI RE sites. The size of the amplified sequence was verified by agarose gel electroporesis, and was purified using a QIAquick PCR purification kit by following manufacturer's instructions (Qiagen, Cat. No. 28106, Valencia, Calif.). Plasmids pAF1S2 and pAF19 were linearizd with RE's HpaI and NotI (New England Biolabs, Beverly, Mass., Cat. No. R0105S) and dephosphorylated using calf intestinal phosphatase (New England Biolabs, Beverly, Mass., Cat. No. M0290S). The GP encoding sequence was similarly digested with HpaI and NotI and ligated into the linearized pAF1S2 and AF19 plasmids resulting in plasmids pSGP1 and pMGP2. These plasmids thus encode the GP polyprotein precursor gene functionally linked to the HCV IRES of rS2 and rM, respectively.

pSGP1 and pMGP2 were digested with RE's KpnI and PsiI, respectively, to serve as in vitro transcription templates. Fluorinated RNA transcripts were generated from each plasmid using the Durascribe T7 (Epicentre, Madison, Wis.) in vitro transcription kit according to the manufacturers instructions. The resultant transcripts thus encoded the GP-1 and GP-2 antigen sequences in both rS2 and rM.

Example 3

Construction of a Prototype Packaging and Delivery Strain

The objective of this study was to create a prototype bacterial packaging strain. Shigella flexneri 15D possesses a non-reverting chromosomal asd marker insertion deletion mutation resulting in a defect in the production of aspartate semialdehyde dehydrogenase (herein referred to as "ASD") and hence the lacks the ability to synthesize the cell wall component diaminopimelic acid (herein referred to as "DAP") (Sizemore et al, Vaccine. 1997 June; 15(8):804-7). Growth, in the absence of genetic complementation, requires the supplementation of culture media with 50 µg/ml DAP (Sigma-Aldrich, St. Louis, Mo., Cat. No. D1377).

While Shigella was chosen only as an example, its invasive characteristics and natural tropism for mucosal immune cells also make it an ideal delivery vector. As the asd mutation is to be complemented by an rdsRN encoded asd allele, it was also necessary to create a second chromosomal lesion to attenuate the strain so as to cause it to lyse after entry into a mammalian cell and release the rdsRN's. Approximately 1 kb regions upstream and downstream of the murI gene (encoding glutamate racemase) were amplified by PCR, joined by ligation of PCR primer encoded NheI sites and ligated into pCVD442 (ref X) at primer encoded SstI and XbaI sites. The resulting plasmid was transferred by conjugation to S. flexneri 15D. Cointegrates were identified by antibiotic resistance, sucrose sensitivity, and PCR analysis, and resolved by means well known to those skilled in the art to produce the asd, murI strain MPC51. The murI mutation renders the cell unable to synthesize the peptidoglycan component D-glutamate and requires supplementation of M9 minimal growth media with 50 µg/ml D-glutamate in order to attain normal growth. Further, HeLa cell invasion assays revealed the strain to be invasive but incapable of prolonged intracellular survival (FIG. 7).

To determine if this auxotrophic requirement can be complemented in trans through expression of asd encoded in an rdsRN, *S. flexneri* MPC51 was transformed with pLM2653, a plasmid that expresses wtL mRNA under the control of SP6 promoter and produces the phi-8 proteins necessary and sufficient to assemble a procapsid (Sun et al., Virology, 308: 354; 2003). Plasmid pLM2653 was introduced by electroporation and selected for by addition of 100 μg/ml ampicillin.

Procapsid assembly in MPC51pLM2653 was assessed by differential filtration of native and SDS-denatured cell lysates, which were analyzed by immunoblotting with antisera specific for procapsid proteins (FIG. 8). Briefly, as the expected MW of each procapsid is 15 MDa, it was shown that procapsid proteins (87 kDa and 34 Da,) failed to pass through a 100 kDa cutoff membrane unless the lysate was treated with 10% SDS, indicating assembly (FIG. 8). Furthermore, transmission electronmicrographs of thin-sectioned MPC51pLM2653 clearly revealed large numbers of approximately 60 nM procapsid particles (FIG. 9).

Example 4

Introduction of ssRNA Encoding rdsRNA Segments into a Prototype Packaging Strain and Launching Functional Self-replicating rdsRN's in Said Strain The goal of the studies in this example was to develop an approach to launching and maintaining rdsRNs in a bacterial packaging strain. The strategy selected involves transforming a packaging strain, *S. flexneri* MPC51pLM2653 (Example 3) with in vitro synthesized ssRNA (+) encoding rM and rS constructs described in Example 2. Following entry into MPC51pLM2653, the ssRNA(+) is packaged into the procapsid and negative-strand synthesis is completed, thereby creating the rdsRNs (FIG. 6). The rdsRN then synthesizes mRNA encoding wtL, rM, and rS mRNA (i.e. ssRNA(+) that is passively secreted from the rdsRN into the cytoplasm of the carrier strain (FIG. 6). These transcripts produce more procapsids via expression of wtL. rM and rS, which both carry a functional asd gene, complement the asd mutation in MPC51, thereby eliminating the DAP requirement for growth. The wtL, rM, and rS mRNA are also packaged into procapsids, thus forming additional rdsRNs.

Electrocompetent cells of MPC51pLM2653 were prepared using standard techniques (Ausubel et al., supra). Briefly, single clones were grown at 37° C. in M9 media supplemented with Ampicillin (100 μg/ml), Kanamycin (50 μg/ml) and 50 μg/ml DAP (Sigma-Aldrich, St. Louis, Mo., Cat. No. D1377). Fifty ml cultures were started at $OD_{600}$<0.1 and cells were harvested during exponential growth, between $OD_{600}$ 0.3 and 0.6. Cells were washed once with ice cold 5 mM EDTA, 10% glycerol (v/v) and then washed three times with ice-cold 10% (v/v) glycerol, each wash was followed by centrifugation at 4000×g. After the final wash and spin, the cells were resuspended in 10% (v/v) glycerol, dispensed into 200 μl aliquots, and stored at −80° C.

The ssRNA(+) of rS and rM employed in electroporating MPC51 pLM2653 were synthesized in vitro using linearized pSTB2 and pMTB7 as DNA templates, respectively, as described in Example 2. MPC51 pLM2653 cells were electroporated with 2 μg ssRNA(+) (1.0 μg rS+1.0 μg rM). Electroporation was conducted using a Gene-Pulser set at 200 Ω, 25 mcF and 1.8 kV (BioRad, Hercules, Calif.). The cells were allowed to recover for 2 hr at 28° C. in SOC medium (cat #15544-034, Invitrogen, Carlsbad, Calif.) supplemented with 50 μg/ml DAP and no antibiotic. Subsequently, the cells were spread on M9 agar with the appropriate antibiotics, supplemented with 50 μg/ml D-glutamate and 0.1 μg/ml DAP, which is below the minimum concentration of DAP required to support growth of MPC51 pLM2653. The cells were allowed to grow at 25-27° C., following which they were transferred to M9 Ap/Kn/D-glutamate and DAP was supplemented to 0.01 μg/ml or withdrawn. The cells were cultured at 22° C.-25° C., the resulting colonies were ampicillin resistant due to pLM2653 and were DAP-independent, due to expression of the asd genes on rS and rM.

In order to improve growth characteristics, MPC51pLM2653 was electroporated with in vitro transcribed ssRNA from pMTB7 and the wild-type segment-S encoding plasmid pLM2775 as a source of gene 8. This procedure and subsequent growth steps were performed as described above and resulted in a DAP-independent MPC51 strain bearing an rdsRN designated LSMtb4 (FIG. 10)

Similarly, MPC51pLM2653 was electroporated with in vitro transcribed ssRNA from the wild-type segment-S encoding plasmid pLM2775 as a source of gene 8 and from pMHc-Red, which encodes the Hc-Red protein functionally linked to the IRES of rM. This procedure and subsequent growth steps were performed as described above and resulted in a DAP-independent MPC51 strain bearing an rdsRP designated LSMHc-Red.

In a third example, ssRNA in vitro transcribed from the rS2 (includes gene-8) construct pSGP1 encoding the LCMV GP antigen was employed to alleviate the need for gene-8 sequence from the wtS. *S. flexneri* MPC51pLM2653 was electroporated with in vitro transcribed RNA from pSGP1 and pMGP2 as in the above described examples. Subsequent growth steps were carried out as described above, resulting in a DAP-independent MPC51 strain bearing an rdsRN designated LSgpMgp. The presence of the rdsRN was confirmed by immunoblotting of whole cell lysates with nucleocapsid-specific antisera and RT-PCR with primers specific for both (+) and (−) strands of rS2 and rM.

Figure 12:
Figure 13:

It is noteworthy that electroporation of MPC51 with any combination of rS and rM in vitro transcribed ssRNA's resulted in no transformants unless accompanied by wtL ssRNA or a plasmid encoding wtL, or the target strain was previously transformed with a plasmid encoding wtL. Furthermore, treatment of in vitro transcribed ssRNA's with RNAse A prior to electroporation of MPC51pLM2653 results in the recovery of no transformants. As an additional example demonstrating the efficiency and efficacy of RNA electroporation as a means of creating rdsRN's, in vitro transcripts of all three wild-type segments were electroporated into *Pseudomonas syringae* (the natural host of phi-8) by methods identical to those described above. This resulted in the recreation of wild-type lytic bacteriophage phi-8 as evidenced by plaque formation in bacterial lawns derived from the electroporation and transmission electron microscopy visualization of wild-type phage particles within *P. syringae* cells derived from the electroporation (FIG. 12).

Figure 11:

DAP-independence appears to result from amplification of the $asd^+$ genes on rS and/or rM RNA encoded by the respective rdsRN. Indeed, RT-PCR analysis of total RNA from strains carrying the above described rdsRN's using primers specific for the amplification of either minus or plus strand RNA results in recovery of cDNA's of rS and rM. Recall that minus strand synthesis in the phage occurs only after the uptake of all three genomic segments. *S. flexneri* MPC51 carrying rdsRN's LSMtb4 and LSMHc-Red have remained DAP-independent for over 3 months in continuous culture at the time of this submission. Finally, these constructs continue to produce capsid proteins detectable by immunoblotting and assembled nucleocapsids visible by transmission electron microscopy (FIG. 11).

In sum, therefore, these results demonstrate that the complementation of the asd deletion in MPC51pLM2653 is the result of RNA uptake and the packaging and self-replicating function of a rdsNC within the packaging strain. These findings further demonstrate that these procedures produce rdsRN's that are maintained in the resulting strains.

Example 5

Expression of rdsRN Encoded Sequences in a Mammalian Cell

While the scope of the invention does not limit delivery of rdsRN's to mammalian tissue or organisms by the use of a bacterial packaging strain, it was decided for purposes of illustration to utilize the attenuated invasive bacterium *Shigella flexneri* MPC51 for this purpose (Examples 3 and 4) as it is naturally invasive in many tissue culture cell lines and animal models. The strain was engineered as described in Example 3 to cause lysis of the bacterial cells after invasion of eukaryotic cells and escape of the endocytic vesicle in order to release the rdsRN's into the eukaryotic cell cytoplasm.

As a first line of evidence, MPC51 bearing rdsRN LSMtb4 was chosen. This rdsRN construct encodes a *M. tuberculosis* antigen package designated TBS. The precise composition of this package is unimportant to the invention described herein, however for explanatory purposes a component of this antigen package is a sequence encoding the protein antigen 85A. As described in Example 2, the antigen package was ligated to the HCV IRES sequence and is under the translational control of this sequence. The absence of expression of the TBS construct within the bacterial strain carrying this rdsRN (MPC51+LSMtb4) was confirmed by immunoblot of whole cell lysates probed for antigen 85A with a polyclonal antisera (Abcam, Cambridge, UK).

HeLa cells (Invitrogen, Carlsbad, Calif.) were grown in DMEM+10% Fetal Bovine Serum (FBS) (Invitrogen, Carlsbad, Calif.)+1% Antibiotic/Antimycotic solution (Invitrogen, Carlsbad, Calif.) to at least 60% confluency on cover slips in 6 well tissue culture flasks at 37° C., 5% $CO_2$. Concurrently, *S. flexneri* MPC51+LSMtb4 was grown in 50 ml M9 at 28° C. with shaking to an $OD_{600}$ of at least 0.6. Twenty-four hours prior to invasion assays, media was removed from HeLa cells and replaced with DMEM+10% FBS. Two hours prior to invasion HeLa cell media was replaced with DMEM and bacterial cultures were diluted and allowed to grow statically at 37° C. The $O_2$ concentration in the tissue culture incubator was then reduced to 1% with $N_2$, and a PBS washed suspension of MPC51+LSMtb4 in DMEM was added to HeLa cultures at a multiplicity of infection (MOI) of 100 and allowed to incubate for 1 hour. Simultaneously, bacterial suspensions of *S. flexneri* 15D (asd) and MPC51pLM2653 similarly prepared were added to wells of HeLa cells in the same manner.

After a one hour invasion incubation, HeLa cells were washed twice with PBS, and culture media (DMEM+FBS) was replaced and supplemented with 150 μg/ml gentamicin sulfate (Sigma, St. Louis, Mo.) for one hour to kill any remaining bacterial cells that had not invaded and hence were not protected by HeLa cells. Gentamicin is broadly antibacterial at this concentration, but does not cross eukaryotic cell membranes. After 1 hour, culture media was replaced with fresh DMEM+FBS and tissue culture cells were left to incubate at 37° C., 5% $CO_2$ for 14 hours.

Cover slips with HeLa cells were then removed, fixed with 2% paraformaldehyde in PBS (pH 7.4), permeabilized with 0.1% Triton X-100 in PBS (pH 7.4), blocked for 2 hours with 3% BSA, 5% Normal Goat Serum, 0.05% Sodium Azide in PBS (pH 7.4), and probed with antigen85A specific antisera (IgY) (Abcam, Cambridge, Mass.) at a dilution of 1:100 in 1% BSA, 3% NGS, 0.05% Sodium Azide in PBS (pH7.4). Cells were then counter-probed with a FITC-conjugated rabbit anti-IgY (Abcam, Cambridge, Mass.) at a dilution of 1:100 in 1% BSA, 3% NGS, 0.05% Sodium Azide in PBS (pH7.4) and examined by fluorescence microscopy. Control HeLa cell groups which were exposed to either no bacteria, *S. flexneri* 15D, or MPC51pLM2653 exhibited no fluorescence indicative of antigen 85A expression. HeLa cells exposed to invasive MPC51+LSMtb4 fluoresced brightly indicative of antigen 85A expression in the cell as part of the TBS antigen fusion protein (FIG. 13). It is important to note again that antigen85A expression was not detectable in the *Shigella* packaging/carrier strain and no live *Shigella* were recovered after the 14 hour incubation. This is clear evidence of mammalian translation of rdsRN produced recombinant segment mRNA.

In a manner similar to that described above, HeLa cell invasions were performed with MPC51+LSMHc-Red, which has the sequence of the directly fluorescent Hc-Red gene encoded on it's rM segments. Twelve hours after the invasion exposure, HeLa cell cover slips were fixed and observed by fluorecscence microscopy. *S. flexneri* 15D and MPC51pLM2653 control groups exhibited no Hc-Red fluorescence; while MPC51+LSMHc-Red exposed HeLa cells were directly fluorescent (FIG. 14). As further proof that this fluorescence was due to Hc-Red expression, HeLa cells were fixed and probed with an antibody specific for Hc-Red and counterprobed with a secondary antibody conjugate. Again, only cells exosed to MPC51+LSMHc-Red were fluorescent (FIG. 15). Further, Hc-Red expression could not be detected by immunoblot or direct fluorescent microscopic analysis of MPC51+LSMHc-Red alone. These combined results provide evidence by direct observation of fluorescence and immunodetection of proteins that rdsRN encoded RNA has been translated into protein in a mammalian cell. Finally, as no or only few live *Shigella* can be recovered at this time point, naked RNA has a finite half-life, and only (+) strand or mRNA can be translated into encoded proteins, it seems clear that the source of the translated message is mRNA produced by the rdsRN's after lysis of the packaging/delivery strain inside the HeLa cell.

Example 6

Exemplary Sequences for Recombinant Segment-S and Recombinant Segment-S2

In reference to FIG. 4, the following are exemplary sequences that have been used in the practice of the invention for construction of recombinant segment-S (rS).

PstI:

```
ctgcag
```

Bacteriophage Phi-8 Segment-S Pac and Ribosomal Binding Site of Gene-8 187 (Bases 1-187 of Segment-S, GenBank Accession no. AF226853):

```
                                        (SEQ ID NO: 1)
gaaattttca aatcttttga ctatttcgct ggcatagctc ttcggagtga agccttccct gaaaggcgcg aaggtcccca
```

-continued
```
ccagctcggg gtgattcgtg acatttcctg ggatctcgga gtcagctttg tctctaggag actgagcgtt cggtctcagg tttaaactga gattgaggat aaagaca
→ connect to the asd gene
```

*E. coli* asd (Bases 240-1343 of GenBank Accession no. V00262):

```
                                       (SEQ ID NO: 2)
atgaaaaatgt tggttttatc ggctggcgcg gtatggtcgg ctccgttctc atgcaacgca tggttgaaga gcgcgacttc gacgccattc gccctgtctt cttttctact tctcagcttg gccaggctgc gccgtctttt ggcggaacca ctggcacact tcaggatgcc tttgatctgg aggcgctaaa ggccctcgat atcattgtga cctgtcaggg cggcgattat accaacgaaa tctatccaaa gcttcgtgaa agcggatggc aaggttactg gattgacgca gcatcgtctc tgcgcatgaa agatgacgcc atcatcattc ttgaccccgt caatcaggac gtcattaccg acggattaaa taatggcatc aggacttttg ttggcggtaa ctgtaccgta agcctgatgt tgatgtcgtt gggtggttta ttcgccaatg atcttgttga ttgggtgtcc gttgcaacct accaggccgc ttccggcggt ggtgcgcgac atatgcgtga gttattaacc cagatgggcc atctgtatgg ccatgtggca gatgaactcg cgaccccgtc ctctgctatt ctcgatatcg aacgcaaagt cacaaccttc acccgtagcg gtgagctgcc ggtggataac tttggcgtgc cgctggcggg tagcctgatt ccgtggatcg acaaacagct cgataacggt cagagccgcg aagagtggaa agggcaggcg gaaaccaaca agatcctcaa cacatcttcc gtaattccgg tagatggttt atgtgtgcgt gtcggggcat tgcgctgcca cagccaggca ttcactatta aattgaaaaa agatgtgtct attccgaccg tggaagaact gctggctgcg cacaatccgt gggcgaaagt cgttccgaac gatcgggaaa tcactatgcg tgagctaacc ccagctgccg ttaccggcac gctgaccacg ccggtaggcc gcctgcgtaa gctgaatatg ggaccagagt tcctgtcagc ctttaccgtg ggcgaccagc tgctgtgggg ggccgcggag ccgctgcgtc ggatgcttcg tcaactggcg taa
→ connect to the IRES
```

```
                                       (SEQ ID NO: 3)
atcactcccc tgtgaggaac tactgtcttc acgcagaaag cgcctagcca tggcgttagt atgagtgtcg tgcagcctcc aggaccccc ctcccgggag agccatagtg gtctgcggaa ccggtgagta caccggaatt gccaggacga ccgggtcctt
```

```
tcttggatca acccgctcaatgcctggaga tttgggcgtg cccccgccag actgctagcc gagtagtgtt gggtcgcgaa aggccttgtg gtactgcctg atagggtgct tgcgagtgcc ccgggaggtc tcgtagaccgtgcacc
→ connect to multiple cloning site
```

Multiple Cloning Site and Termination Codons:

```
                                       (SEQ ID NO: 4)
atg gtt aac gcg gcc gct taa tta ata aat aaa taa
→ connect to SFV-3' untranslated
```

Semliki Forest Virus-3-Prime Untranslated Region (Bases 1-262 of GenBank Accession no. V01398):

```
                                       (SEQ ID NO: 5)
gttagggta ggcaatggca ttgatatagc aagaaaattg aaaacagaaa aagttagggt aagcaatggc atataaccat aactgtataa cttgtaacaa agcgcaacaa gacctgcgca attggccccg tggtccgcct cacggaaact cggggcaact catattgaca cattaattgg caataattgg aagcttacat aagcttaatt cgacgaataa ttggattttt attttatttt gcaattggtt tttaatattt cc
→ connect to φ8 segment-S 3' RNA pol binding-
  site
```

Phi-8 Segment-S 3-Prime Polymerase Binding Site (Bases 3081-3192 of GenBank Accession no. AF226853):

```
                                       (SEQ ID NO: 6)
gcttagcggc aatcgaaccc tccg xcataagg aggtttagca aatccgcggc tcttatgagc tgtccgaaag gacaacccga aaggggagc gaggacttcg gtcctccgct cc
```

PstI:

```
ctgcag
```

In reference to FIG. 4, the following are exemplary sequences that have been used in the practice of the invention for construction of recombinant segment-S2 encoding gene 8 of the wild-type phage phi-8 (rS2).

PstI:

```
ctgcag
```

Bacteriophage Phi-8 Segment-S Pac (Bp 1-187 GenBank Accession no. AF226853):

```
                                       (SEQ ID NO: 1)
gaaattttcaaatcttttgactatttcgctggcatagctcttcggagtga agccttccctgaaaggcgcgaaggtccccaccagctcggggtgattcgtg acatttcctgggatctcggagtcagctttgtctctaggagactgagcgtt cggtctcaggtttaaactgagattgaggataaagaca
```

Bacteriophage Phi-8 Gene 8 of Segment-S (Bp 188-1291 GenBank Accession no. AF226853):

(SEQ ID NO: 7)
atgggtagaatctttcaactgttgatgcgcttaggcgttaaacagggtgc agcaagtgttggtaaagccgggatcgatgctggtagcaagcgattgctcc agcagatcatgtccaaagacggtgctattcagctgtctaaggcactcggt ttcaccgctgtggagcagatgtcgagtgaagtgctcgaagcgtatctcta tgagatcgttgagcatcttctgctcgtcgacgaggccacgttggccgatg cgcttatggcgtgtatcaccgatgcaggtgatatcgccattgagcgtctg cttccttccgtagaggatgtcgacaaaggcgaggcgcttgccgccacgct gactgtcgtcttggctctcttctcgatgaacaaagaacaagctgaagagc ttaaacgttcgatggcatcgaaaggcttgagtccggaccgggttaccctc ggaggacagaccctgttgaccgtcaagtccactggtactggcctgacaga gtatgacgctcaaggcaagaatggcgtccctcgcgggatgtctgctaaca agcgtactgcattgttcttcgtgctgtacacagtgatcagtacttcctgg tccgtatacgatcactatggtgaggttaaagctggtctcgcacgaggcga gctacctcccagtgctgatcgtgttgaattgcgggccccggttcctccg taagtgcgatcgagcgtgagacacaacgcgcactgcaagaagaacagccg cgtgcattgccttcgggcagccgcaccgcggaacgggttgctgggccgac gcagggtgatgtccccgtgctcacacctccgccaggtcgattcaccttca ccggtgagggcgaccatcgtcccgatttcgcacaactcgctcgccagaac gacactgatggcgttgtgcggatcattgaactggatcgcattccagatgc aaggaaaatattagtcgatggtgaccatgactacttgctggacgccgctc aacagcgcgtcgctgccgatatcggggtatcgcccgagtcagtaggtcga ttcgctgctctggtagccagtatcatcaacgcgaaggagaagcgttcgtg atgc BglII:

agatct
→ connect to the IRES

→connect to the IRES
Hepatitis C Virus-IRES (Bases 36-341 of GenBank Accession no. AJ242651):

(SEQ ID NO: 3)
atcactcccc tgtgaggaac tactgtcttc acgcagaaag cgcctagcca tggcgttagtatgagtgtcg tgcagcctcc aggaccccc ctcccgggag agccatagtg gtctgcggaa ccggtgagta caccggaatt gccaggacga ccgggtcctt tcttggatca acccgctcaatgcctggaga tttgggcgtg ccccgccag actgctagcc gagtagtgtt gggtcgcgaaaggccttgtg gtactgcctg ataggggtgct tgcgagtgcc ccgggaggtc tcgtagaccgtgcaccatg
→ connect to multiple cloning site Multiple Cloning Site and Termination Codons:

(SEQ ID NO: 4)
atg gtt aac gcg gcc gct taa tta ata aat aaa taa
→ connect to SFV-3' untranslated Semliki Forest Virus-3-Prime Untranslated Region (Bases 1-262 of GenBank Accession No. V01398):

(SEQ ID NO: 5)
gttagggta ggcaatggca ttgatatagc aagaaaattg aaaacagaaa aagttagggt aagcaatggc atataaccat aactgtataa cttgtaacaa agcgcaacaa gacctgcgca attggccccg tggtccgcct cacggaaact cggggcaact catattgaca cattaattgg caataattgg aagcttacat aagcttaatt cgacgaataa ttggattttt attttatttt gcaattggtt tttaatattt cc
→ connect to φ8 segment-S 3' RNA pol binding site Phi-8 Segment-S 3-Prime Polymerase Binding Site (Bases 3081-3192 of GenBank Accession no. AF226853):

(SEQ ID NO: 6)
gcttagcggc aatcgaaccc tccg xcataagg aggtttagca aatccgcggc tcttatgagc tgtccgaaag gacaacccga aaggggagc gaggacttcg gtcctccgct cc PstI:

ctgcag

Example 7

Exemplary Sequences for Recombinant Segment-M

With reference to FIG. 4, the following are exemplary sequences that may be used in the practice of the invention for construction of Recombinant segment-M.

KpnI:

ggtacc
→ connect to segment M pac

Segment M Pac Sequence and Ribosomal Binding Site of Gene 10 (Bases 1-262 of GenBank Accession no. AF226852)

(SEQ ID NO: 8)
gaaattttcaaagtctttcggcaataagggtggaaatttcaaagagggtc gagccgacgaacctctgtagaaccgggaagtgcctgtctttacttgcgag agcaattgaactagggcagcaccgggggtcgataagcgcagaagtgaggc gcggggattgaagcaaatcacctaagcgtaaacgacggacctcgagggtg gcggagtctacataggatcccctagctactagacagaaac cattcctaacaaggagatgcac
→ connect to Bgl II BglII:

```
agatct
→ connect to the asd gene
```

*E. coli* Asd (Bases 240-1343 of GenBank Accession no. V00262):

```
                                                                    (SEQ ID NO: 9)
atgaaaaatgt tggttttatc ggctggcgcg gtatggtcgg ctccgttctc atgcaacgca tggttgaaga gcgcgacttc gacgccattc gccctgtctt cttttctact tctcagcttg gccaggctgc gccgtctttt ggcggaacca ctggcacact tcaggatgcc tttgatctgg aggcgctaaa ggccctcgat atcattgtga cctgtcaggg cggcgattat accaacgaaa tctatccaaa gcttcgtgaa agcggatggc aaggttactg gattgacgca gcatcgtctc tgcgcatgaa agatgacgcc atcatcattc ttgaccccgt caatcaggac gtcattaccg acggattaaa taatggcatc aggacttttg ttggcggtaa ctgtaccgta agcctgatgt tgatgtcgtt gggtggttta ttcgccaatg atcttgttga ttgggtgtcc gttgcaacct accaggccgc ttccggcggt ggtgcgcgac atatgcgtga gttattaacc cagatgggcc atctgtatgg ccatgtggca gatgaactcg cgaccccgtc ctctgctatt ctcgatatcg aacgcaaagt cacaacctta acccgtagcg gtgagctgcc ggtggataac tttggcgtgc cgctggcggg tagcctgatt ccgtggatcg acaaacagct cgataacggt cagagccgcg aagagtggaa agggcaggcg gaaaccaaca agatcctcaa cacatcttcc gtaattccgg tagatggttt atgtgtgcgt gtcggggcat tgcgctgcca cagccaggca ttcactatta aattgaaaaa agatgtgtct attccgaccg tggaagaact gctggctgcg cacaatccgt gggcgaaagt cgttccgaac gatcgggaaa tcactatgcg tgagctaacc ccagctgccg ttaccggcac gctgaccacg ccggtaggcc gcctgcgtaa gctgaatatg ggaccagagt tcctgtcagc ctttaccgtg ggcgaccagc tgctgtgggg ggccgcggag ccgctgcgtc ggatgcttcg tcaactggcg taa
→ connect to the AscI
```

AscI:

```
ggcgcgcc
→ connect to HCV-IRES
```

Hepatitis C Virus-IRES (Bases 36-341 of GenBank Accession no. AJ242651):

```
                                            (SEQ ID NO: 10)
atcactcccc tgtgaggaac tactgtcttc acgcagaaag cgcctagcca tggcgttagt atgagtgtcg tgcagcctcc aggacccccc ctcccgggag agccatagtg gtctgcggaa ccggtgagta caccggaatt gccaggacga ccgggtcctt tcttggatca acccgctcaa tgcctggaga tttgggcgtg cccccgccag actgctagcc gagtagtgtt gggtcgcgaa aggccttgtg gtactgcctg atagggtgct tgcgagtgcc ccgggaggtc tcgtagaccg tgcacc
→ connect to multiple cloning site
```

Multiple Cloning Site:

```
                                            (SEQ ID NO: 11)
atg gtt aac gcg gcc gct taa tta ata aat aaa taa
→ connect to SFV 3-prime untranslated sequence
```

Semliki Forest Virus-3-Prime Untranslated Region (Bases 1-262 of GenBank Accession no. V01398):

```
                                            (SEQ ID NO: 12)
gttagggta ggcaatggca ttgatatagc aagaaaattg aaaacagaaa aagttagggt aagcaatggc atataaccat
```

-continued

```
aactgtataa cttgtaacaa agcgcaacaa gacctgcgca attggccccg tggtccgcct cacggaaact cggggcaact catattgaca cattaattgg caataattgg aagcttacat aagcttaatt cgacgaataa ttggattttt attttatttt gcaattggtt tttaatattt cc
→ connect to Phi-8 3-prime polymerase binding site
```

Phi-8 Segment M 3-Prime Polymerase Binding Site (Bases 4677-4741 of GenBank Accession no. AF226852):

```
                                            (SEQ ID NO: 13)
actgttgataaacaggacccggaagggtaacccgagagggggagtgaggc ttcggcctccacttc
→ connect to PstI
```

PstI:

```
ctgcag
```

Example 8

Extraction and Purification of rdsRNs

To demonstrate that strain MPC51 LSMtb4 produces nucleocapsids, single clones were grown at 28° C. in M9 medium supplemented with ampicillin (100 μg/ml), kanamycin (50 μg/ml) and D-Glutamate (50 μg/ml). Cultures were started at $OD_{600}$<0.1 and cells were harvested during exponential growth, between $OD_{600}$ 0.6 and 0.8. Cells were harvested by centrifugation at 8000 rpm for 5 min. To lyse cells, the bacteria were resuspended in 5 ml PBS and lysed at 20,000 psi in a French pressure cell (Thermo Electron). The lysates were subjected to centrifugation at 8,000×g for 5 min and the supernatants were applied to 10-30% (w/v) sucrose gradients containing 10 mM potassium phosphate (pH 7.3; Sigma, St. Louis, Mo., Cat. No. P5379) and 1 mM magnesium chloride (Sigma, St. Louis, Mo., Cat. No. M1028). The gradients were placed in a JS24.15 rotor in an Avanti J-30i centrifuge (Beckman Coulter, Fullerton, Calif., Cat. No. 363118). After centrifugation at 23,000 rpm and 23° C. for 90 min, the nucleocapsids formed a sharp band that was collected and stored separately at −80° C. The remaining contents of the tubes were fractionated in 1 ml aliquots and stored at −80° C. The presence of rdsRN's in these aliquots was verified by immunoblotting with capsid-specific antisera and by RT-PCR using primers designed to amplify (+) and (−) strand LSMtb4 RNA.

An improved rdsRN purification procedure has been designed as follows. A 500 ml culture of S. flexneri MPC51 bearing rdsRN LSMtb4 will be grown at 28° C. to an OD600=0.8, and the cells pelleted. The rdsRN's will be purified using a multi-step filtration and centrifugation process. The cell pellet will first be lysed using an Invensys APV Microfluidyzer (Lake Wills, Wis.) and clarified by centrifugation. The clarified supernatant will then be processed by tangential-flow filtration (TFF) using a Pellicon system (Millipore Inc., Billerica, Mass.) with a 0.45 µm pore size element (Millipore #P2HV MPC 05, or equivalent). Free nucleic acids will then be digested with Benzonase (for 30 minutes at 25° C.).

A second filtration step will then be used to concentrate the rdsRN's and wash out medium components, digested nucleic acids, and the nucleases. Tangential flow filtration using a 100 kDa spiral wound ultrafiltration module (Millipore #CDUF 006 LH, or equivalent) will be used to concentrate the product and exchange the buffer into phosphate-buffered saline or other client-specified buffer of choice. Following tangential flow filtration, one-half of the partially purified rdsRN's will then be precipitated by the addition of NaCl and PEG, and then resuspended in a small volume of a phosphate buffer (Hoogstraten et al., Virology, 272:218-224, 2000). Two small analytical scale gradient purifications will then be implemented using a portion (10-25%) of the PEG precipitated and resuspended material. Resuspended rdsRN's will be layered onto both preformed sucrose and opti-prep gradients and centrifuged overnight. The rdsRN band (identified by immunoblot and RT-PCR analysis) will be collected and the gradient material removed by dialysis against a buffer specified by the contracting laboratory. Purified material (both pre- and post-gradient) will then be processed to remove residual Endotoxin (if needed) using Q-ion exchange chromatography and/or Acticlean Etox™ (Sterogene, Carlsbad, Calif.). Final purified rdsRN's will be aliquoted and stored at 4° C.

Aliquots will be taken at each stage of the purification process and analyzed by immunoblot and RT-PCR.

Example 9

Immunogenicity of rdsRNs in Mice

Given that this invention is based on the RNA-dependent RNA polymerase of a bacteriophage, it is pertinent to determine whether phi-8 polymerase is functional in eukaryotes. The ability of purified nucleocapsids to elicit an antibody response against the mycobacterial antigen package TBS encoded on rS and rM will be tested by vaccinating 6-8 week old BALB/c mice (The Jackson Laboratory, Bar Harbor, Me., Cat. No. 000651) with purified nucleocapsids. Five groups, each consisting of five mice, will be vaccinated as follows: 10 µg empty procapsid, 10 ng nucleocapsid, 100 ng nucleocapsid, 1 µg nucleocapsid, and 10 µg nucleocapsid. The mice will receive a priming vaccination on day 0 and receive two booster vaccinations on days 14 and 42. All vaccinations will be intramuscular by injecting nucleocapsids into the hind legs of each mouse.

To measure humoral responses to the TBS antigens, sera will be collected before and at 10-day intervals after each vaccination. About 100 µl of blood per mouse will be collected into individual tubes from each mouse-tail vein and allowed to clot by incubating for 4 hr on ice. After centrifugation in a microfuge for 5 min, the sera will be transferred to fresh tubes and stored at −20° C.

Solid phase ELISA will be utilized to quantitate IgG responses to the TBS antigens. Purified soluble mycobacterial antigens are suspended in PBS at a concentration of 2 µg/ml and is used to coat 96-well microtiter ELISA plates. The plates are incubated overnight at 4° C. followed by four washes with 0.05% (v/v) TBS-Tween solution. The plates are then blocked at room temperature for 1 hr with blotto (5% (w/v) non-fat dried milk in TBS). Plates are then washed with TBS-Tween solution, as above. Sera are diluted in blotto and threefold serial dilutions, beginning at 1:30, are added in duplicates to the plates so that volume per well is 100 µl. Pre-immunization serum is included in each ELISA as a negative control. Plates are incubated for 2 hr at room temperature followed by four washes with TBS-Tween solution. For detection, the secondary antibody is alkaline phosphatase labeled affinity-purified goat anti-mouse IgG (heavy chain specific) (Accurate Chemical and Scientific Corporation, Westbury, N.Y., Cat. No. SBA103004). The secondary antibody is diluted 1:2000 in TBS, 2% (w/v) non-fat dry milk, and 5% (v/v) lamb serum, 100 µl of which is added to each well and incubated at room temperature for 1 hr. Color is developed by sequential 15 min incubations in 100 µl of substrate followed by 100 µl amplifier of Invitrogen's ELISA amplification system (Cat No. 19589-019). Absorbance is determined at 490 nm using a SpectraMax microplate spectrophotometer (Molecular Devices, Sunnyvale, Calif.). End-point titers are calculated by taking the inverse of the last serum dilution that produced an increase in absorbance at 490 nm that is greater than the mean of the negative control row plus three standard error values.

Cellular immunity may be measured by intracellular cytokine staining (also referred to as intracellular cytokine cytometry) or by ELISPOT (Letsch A. et al., Methods 31:143-49; 2003). Both methods allow the quantitation of antigen-specific immune responses, although ICS also adds the simultaneous capacity to phenotypically characterize antigen-specific CD4+ and CD8+ T-cells. Such assays can assess the numbers of antigen-specific T cells that secrete IL-2, IL-4, IL-5, IL-6, IL-10 and IFN- (Wu et al., AIDS Res. Hum. Retrovir. 13: 1187; 1997). ELISPOT assays are conducted using commercially-available capture and detection mAbs (R&D Systems and Pharmingen), as described (Wu et al., Infect. Immun. 63:4933; 1995) and used previously (Xu-Amano et al., J. Exp. Med. 178:1309; 1993); (Okahashi et al., Infect. Immun. 64: 1516; 1996). Each assay includes mitogen (Con A) and ovalbumin controls.

Example 10

Segment-L Expression

As described in Examples 3 and 4 above, segment-wtL is introduced into the bacterial packaging strain as an extrachromosomally replicating plasmid. Clearly, a more stable method of expressing wtL is by integration into the bacterial chromosome. A truncated copy of wtL that lacks the pac sequence may be integrated into the chromosome to create a procapsid producing strain, in which case, full-length wild-type or recombinant segment-L RNA must subsequently be electroporated into integrates along with rM and rS RNA to complete packaging of all three segments. Alternatively, full-length wtL is integrated into the chromosome, thereby eliminating the need to subsequently introduce wtL RNA by electroporation.

Chromosomal integration may be achieved by homologous recombination using a temperature sensitive plasmid (herein referred to as "TS"), plasmids that can replicate only at a permissive temperature (30° C.), but not at non-permissive temperatures (42° C. and above) (Kretschmer et al., J. Bacteriol. 124:225; 1975); (Hashimoto and Sekiguchi, J. Bacteriol. 127:1561; 1976). Examples of TS plasmids include pMAK705, pTSA29, pTSC29, pTSK29, all of which are pSC101 derivatives (Hamilton et al., J. Bacteriol. 171: 4617; 1989); (Phillips, Plasmid 41:78; 1999).

The use of TS plasmids in allelic exchange has been described in detail elsewhere (Hashimoto and Sekiguchi, J. Bacteriol. 127:1561; 1976); (Hamilton et al., J. Bacteriol. 171:4617; 1989); (Phillips, Plasmid 41:78; 1999). Briefly, the wtL sequence is cloned into a TS plasmid such that it is flanked by sequences of the gene to be deleted. The plasmid carrying the cloned gene is then electroporated into the target bacteria and the cells are grown at 42° C. to allow cointegrate formation, that is, the intial recombination event between homologous sequences of the chromosome and the plasmid. Cointegrates are selected by growing the cells on media that is supplemented with the antibiotic marker that is carried on the plasmid. Given that the plasmid does not replicate at 42° C., only cointegrates will be antibiotic resistant. Cointegrates carry the plasmid origin of replication in the chromosome, replication from which is deleterious to the cell when cointegrates are subsequently grown at 30° C. in the presence of antibiotic. Thus, at 30° C. a second recombination event (resolution) occurs resulting in plasmid regeneration. Single colonies are then tested for antibiotic resistance at 42° C., so that antibiotic sensitive colonies no longer have plasmid integrated into the chromosome. To cure the cells of the plasmid generated by the second recombination, the cells are grown at 42° C. without antibiotic.

In yet another approach, a TS plasmid may be used to express wtL, much like in Example 3, however, the bacteria are initially grown at permissive temperature only. The wtL is cloned under the control of a bacterial promoter, such as T7, from which it is expressed at 30° C. Following the introduction of rM and rS RNA by electroporation, the procapsids encoded by wtL package and replicate both RNAs. The cells may then be cured of the plasmid by growing at 42° C. and no antibiotic. The resulting plasmid-free cells will continue to replicate RNA and may be used as bacterial vaccine vectors that do not carry regulatory concerns associated with plasmids, such as introduction of antibiotic resistance.

While the invention has been described in detail, and with reference to specific embodiments thereof, it will be apparent to one of ordinary skill in the art that various changes and modifications can be made therein without departing from the spirit and scope thereof.

We claim:

1. A recombinant double-stranded RNA nucleocapsid (rdsRN), comprising
   a) proteins with RNA packaging activity, and
   b) RNA sequences comprising at least:
      i) RNA encoding a product, and
      ii) an RNA of interest operably linked to a eukaryotic translation initiation sequence.

2. The rdsRN of claim 1, further comprising nucleic acid sequences encoding segment-L of an RNA phage.

3. The rdsRN of claim 1, wherein said RNA sequences comprise at least a portion of segment-S of an RNA phage or segment-M of an RNA phage, or both.

4. The rdsRN of claim 3, wherein said portion of segment-S is a segment-S pac sequence, gene 8, or the wild-type segment-S.

5. The rdsRN of claim 3, wherein said portion of segment-S is a segment-S RNA dependent polymerase recognition sequence.

6. The rdsRN of claim 3, wherein said portion of segment-M is a segment-M pac sequence.

7. The rdsRN of claim 3, wherein said portion of segment-M is a segment-M RNA dependent polymerase recognition sequence.

8. The rdsRN of claim 1, wherein said product complements a selectable phenotypic mutation in a host cell.

9. The rdsRN of claim 8, wherein said phenotypic mutation is selected from the group consisting of aroA, aroC, and leuD.

10. The rdsRN of claim 8, wherein said phenotypic mutation is a cell wall synthesis mutation.

11. The rdsRN of claim 10, wherein said cell wall synthesis mutation is selected from the group consisting of asd and murI.

12. The rdsRN of claim 8, wherein said phenotypic mutation is a mutation that prevents growth at temperatures above 32° C.

13. The rdsRN of claim 12, wherein said phenotypic mutation is htrB.

14. The rdsRN of claim 1, wherein said proteins with RNA packaging activity are derived from a phage selected from the group consisting of Phi-6, Phi-8 and Phi-13.

15. The rdsRN of claim 1, wherein said RNA of interest encodes a protein selected from the group consisting of a viral antigen, a bacterial antigen, a parasitic antigen, a tumor antigen, a transplant antigen, an autoimmune antigen, an adjuvant and a cytokine.

16. The rdsRN of claim 1, wherein one or more of said RNA sequences are fluorinated.

17. The rdsRN of claim 10, wherein said cell wall synthesis mutation is asd.

18. The rdsRN of claim 14, wherein said proteins with RNA packaging activity are derived from phage Phi-8 and include gene 8 of phage Phi-8.

19. The rdsRN of claim 15, wherein said protein is a bacterial antigen.

20. The rdsRN of claim 19, wherein said bacterial antigen is a tuberculosis antigen.

21. The rdsRN of claim 1, wherein said RNA of interest encodes an apoptosis enhancing protein.

22. The rdsRN of claim 1, wherein said RNA of interest encodes a tolerance inducing protein, wherein said tolerance inducing protein is Caspase 9.

23. The rdsRN of claim 1, wherein said RNA sequences comprises nuclease resistant RNA.

24. The rdsRN of claim 23, wherein said nuclease resistant RNA is fluorinated RNA.

25. The rdsRN of claim 8, wherein said selectable phenotypic mutation is a non-reverting selectable phenotypic mutation.

* * * * *

SEQUENCE LISTING

```
<160> NUMBER OF SEQ ID NOS: 13

<210> SEQ ID NO 1
<211> LENGTH: 187
<212> TYPE: DNA
<213> ORGANISM: Bacteriophage phi 7-9

<400> SEQUENCE: 1
gaaattttca aatcttttga ctatttcgct ggcatagctc ttcggagtga agccttccct      60
gaaaggcgcg aaggtcccca ccagctcggg gtgattcgtg acatttcctg ggatctcgga     120
gtcagctttg tctctaggag actgagcgtt cggtctcagg tttaaactga gattgaggat     180
aaagaca                                                               187

<210> SEQ ID NO 2
<211> LENGTH: 1104
<212> TYPE: DNA
<213> ORGANISM: Escherichia coli

<400> SEQUENCE: 2
atgaaaaatg ttggttttat cggctggcgc ggtatggtcg gctccgttct catgcaacgc      60
atggttgaag agcgcgactt cgacgccatt cgccctgtct tcttttctac ttctcagctt     120
ggccaggctg cgccgtcttt tggcggaacc actggcacac ttcaggatgc ctttgatctg     180
gaggcgctaa aggccctcga tatcattgtg acctgtcagg gcggcgatta taccaacgaa     240
atctatccaa agcttcgtga aagcggatgg caaggttact ggattgacgc agcatcgtct     300
ctgcgcatga aagatgacgc catcatcatt cttgaccccg tcaatcagga cgtcattacc     360
```

```
gacggattaa ataatggcat caggactttt gttggcggta actgtaccgt aagcctgatg    420
ttgatgtcgt tgggtggttt attcgccaat gatcttgttg attgggtgtc cgttgcaacc    480
taccaggccg cttccggcgg tggtgcgcga catatgcgtg agttattaac ccagatgggc    540
catctgtatg gccatgtggc agatgaactc gcgaccccgt cctctgctat tctcgatatc    600
gaacgcaaag tcacaacctt aacccgtagc ggtgagctgc cggtggataa ctttggcgtg    660
ccgctggcgg gtagcctgat tccgtggatc gacaaacagc tcgataacgg tcagagccgc    720
gaagagtgga agggcaggc ggaaaccaac aagatcctca acacatcttc cgtaattccg    780
gtagatggtt tatgtgtgcg tgtcggggca ttgcgctgcc acagccaggc attcactatt    840
aaattgaaaa aagatgtgtc tattccgacc gtggaagaac tgctggctgc gcacaatccg    900
tgggcgaaag tcgttccgaa cgatcgggaa atcactatgc gtgagctaac cccagctgcc    960
gttaccggca cgctgaccac gccggtaggc cgcctgcgta agctgaatat gggaccagag   1020
ttcctgtcag ccttttaccgt gggcgaccag ctgctgtggg gggccgcgga gccgctgcgt   1080
cggatgcttc gtcaactggc gtaa                                          1104

<210> SEQ ID NO 3
<211> LENGTH: 306
<212> TYPE: DNA
<213> ORGANISM: Hepatitis C virus

<400> SEQUENCE: 3
atcactcccc tgtgaggaac tactgtcttc acgcagaaag cgcctagcca tggcgttagt     60
atgagtgtcg tgcagcctcc aggaccccccc ctcccgggag agccatagtg gtctgcggaa    120
ccggtgagta caccggaatt gccaggacga ccgggtcctt tcttggatca acccgctcaa    180
tgcctggaga tttgggcgtg ccccccgcag actgctagcc gagtagtgtt gggtcgcgaa    240
aggccttgtg gtactgcctg atagggtgct tgcgagtgcc ccgggaggtc tcgtagaccg    300
tgcacc                                                                306

<210> SEQ ID NO 4
<211> LENGTH: 36
<212> TYPE: DNA
<213> ORGANISM: Artificial
<220> FEATURE:
<223> OTHER INFORMATION: multiple cloning site

<400> SEQUENCE: 4
atggttaacg cggccgctta attaataaat aaataa                               36

<210> SEQ ID NO 5
<211> LENGTH: 261
<212> TYPE: DNA
<213> ORGANISM: Semliki Forest virus

<400> SEQUENCE: 5
gttagggtag gcaatggcat tgatatagca agaaaattga aaacagaaaa agttagggta     60
agcaatggca tataaccata actgtataac ttgtaacaaa gcgcaacaag acctgcgcaa    120
ttggccccgt ggtccgcctc acggaaactc ggggcaactc atattgacac attaattggc    180
aataattgga agcttacata agcttaattc gacgaataat tggattttta ttttatttg    240 caattggttt ttaatatttc c                                              261

<210> SEQ ID NO 6
<211> LENGTH: 112
<212> TYPE: DNA
```

<213> ORGANISM: Bacteriophage phi 7-9

<400> SEQUENCE: 6

```
gcttagcggc aatcgaaccc tccgataagg aggtttagca aatccgcggc tcttatgagc    60
tgtccgaaag gacaacccga aaggggagc gaggacttcg gtcctccgct cc            112
```

<210> SEQ ID NO 7
<211> LENGTH: 1104
<212> TYPE: DNA
<213> ORGANISM: Bacteriophage phi 7-9

<400> SEQUENCE: 7

```
atgggtagaa tctttcaact gttgatgcgc ttaggcgtta acagggtgc agcaagtgtt     60
ggtaaagccg ggatcgatgc tggtagcaag cgattgctcc agcagatcat gtccaaagac   120
ggtgctattc agctgtctaa ggcactcggt ttcaccgctg tggagcagat gtcgagtgaa   180
gtgctcgaag cgtatctcta tgagatcgtt gagcatcttc tgctcgtcga cgaggccacg   240
ttggccgatg cgcttatggc gtgtatcacc gatgcaggtg atatcgccat tgagcgtctg   300
cttccttccg tagaggatgt cgacaaaggc gaggcgcttg ccgccacgct gactgtcgtc   360
ttggctctct tctcgatgaa caaagaacaa gctgaagagc ttaaacgttc gatggcatcg   420
aaaggcttga gtccggaccg ggttaccctc ggaggacaga ccctgttgac cgtcaagtcc   480
actggtactg gcctgacaga gtatgacgct caaggcaaga atggcgtccc tcgcgggatg   540
tctgctaaca gcgtactgc attgttcttc gtgctgtaca cagtgatcag tacttcctgg    600
tccgtatacg atcactatgg tgaggttaaa gctggtctcg cacgaggcga gctacctccc   660
agtgctgatc gtgttgaatt gcgggccccc ggttcctccg taagtgcgat cgagcgtgag   720
acacaacgcg cactgcaaga agaacagccg cgtgcattgc cttcgggcag ccgcaccgcg   780
gaacgggttg ctgggccgac gcagggtgat gtccccgtgc tcacacctcc gccaggtcga   840
ttcaccttca ccgtgaggg cgaccatcgt cccgatttcg cacaactcgc tcgccagaac   900
gacactgatg cgttgtgcg gatcattgaa ctggatcgca ttccagatgc aaggaaaata   960
ttagtcgatg gtgaccatga ctacttgctg gacgccgctc aacagcgcgt cgctgccgat  1020
atcggggtat cgcccgagtc agtaggtcga ttcgctgctc tggtagccag tatcatcaac  1080
gcgaaggaga agcgttcgtg atgc                                         1104
```

<210> SEQ ID NO 8
<211> LENGTH: 262
<212> TYPE: DNA
<213> ORGANISM: Bacteriophage phi 7-9

<400> SEQUENCE: 8

```
gaaattttca agtctttcg gcaataaggg tggaaatttc aaagagggtc gagccgacga     60
acctctgtag aaccgggaag tgcctgtctt tacttgcgag agcaattgaa ctagggcagc   120
accgggggtc gataagcgca gaagtgaggc gcggggattg aagcaaatca cctaagcgta   180
aacgacggac ctcgagggtg gcggagtcta cataggatcc cctagctact agacagaaac   240
cattcctaac aaggagatgc ac                                            262
```

<210> SEQ ID NO 9
<211> LENGTH: 1104
<212> TYPE: DNA
<213> ORGANISM: Escherichia coli

<400> SEQUENCE: 9

```
atgaaaaatg ttggttttat cggctggcgc ggtatggtcg gctccgttct catgcaacgc    60
atggttgaag agcgcgactt cgacgccatt cgccctgtct tcttttctac ttctcagctt   120
ggccaggctg cgccgtcttt tggcggaacc actggcacac ttcaggatgc ctttgatctg   180
gaggcgctaa aggccctcga tatcattgtg acctgtcagg cggcgatta taccaacgaa    240 atctatccaa agcttcgtga agcggatgg caaggttact ggattgacgc agcatcgtct    300
ctgcgcatga agatgacgc catcatcatt cttgaccccg tcaatcagga cgtcattacc    360
gacggattaa ataatggcat caggactttt gttggcggta actgtaccgt aagcctgatg   420
ttgatgtcgt tgggtggttt attcgccaat gatcttgttg attgggtgtc cgttgcaacc   480
taccaggccg cttccggcgg tggtgcgcga catatgcgtg agttattaac ccagatgggc   540
catctgtatg gccatgtggc agatgaactc gcgaccccgt cctctgctat tctcgatatc   600
gaacgcaaag tcacaacctt aacccgtagc ggtgagctgc cggtggataa cttggcgtg    660 ccgctggcgg gtagcctgat tccgtggatc gacaaacagc tcgataacgg tcagagccgc   720
gaagagtgga agggcaggc ggaaaccaac aagatcctca acacatcttc cgtaattccg    780
gtagatggtt tatgtgtgcg tgtcggggca ttgcgctgcc acagccaggc attcactatt    840
aaattgaaaa aagatgtgtc tattccgacc gtggaagaac tgctggctgc gcacaatccg   900
tgggcgaaag tcgttccgaa cgatcgggaa atcactatgc gtgagctaac cccagctgcc   960
gttaccggca cgctgaccac gccggtaggc cgcctgcgta agctgaatat gggaccagag  1020
ttcctgtcag cctttaccgt gggcgaccag ctgctgtggg gggccgcgga gccgctgcgt  1080
cggatgcttc gtcaactggc gtaa                                        1104

<210> SEQ ID NO 10
<211> LENGTH: 306
<212> TYPE: DNA
<213> ORGANISM: Hepatitis C virus

<400> SEQUENCE: 10
atcactcccc tgtgaggaac tactgtcttc acgcagaaag cgcctagcca tggcgttagt    60
atgagtgtcg tgcagcctcc aggacccccc ctcccgggag agccatagtg gtctgcggaa   120
ccggtgagta caccggaatt gccaggacga ccgggtcctt tcttggatca acccgctcaa   180
tgcctggaga tttgggcgtg cccccgccag actgctagcc gagtagtgtt gggtcgcgaa   240
aggccttgtg gtactgcctg atagggtgct tgcgagtgcc ccgggaggtc tcgtagaccg    300
tgcacc                                                              306

<210> SEQ ID NO 11
<211> LENGTH: 36
<212> TYPE: DNA
<213> ORGANISM: Artificial
<220> FEATURE:
<223> OTHER INFORMATION: multiple cloning site

<400> SEQUENCE: 11
atggttaacg cggccgctta attaataaat aaataa                              36

<210> SEQ ID NO 12
<211> LENGTH: 261
<212> TYPE: DNA
<213> ORGANISM: Semliki Forest virus

<400> SEQUENCE: 12
gttagggtag gcaatggcat tgatatagca agaaaattga aaacagaaaa agttagggta    60
```

```
agcaatggca tataaccata actgtataac ttgtaacaaa gcgcaacaag acctgcgcaa    120
ttggccccgt ggtccgcctc acggaaactc ggggcaactc atattgacac attaattggc    180
aataattgga agcttacata agcttaattc gacgaataat tggatttta tttatttg      240 caattggttt ttaatatttc c                                              261

<210> SEQ ID NO 13
<211> LENGTH: 65
<212> TYPE: DNA
<213> ORGANISM: Bacteriophage phi 7-9

<400> SEQUENCE: 13
actgttgata aacaggaccc ggaagggtaa cccgagaggg ggagtgaggc ttcggcctcc    60
acttc                                                                65
```